United States Patent
Kupper et al.

(10) Patent No.: US 9,629,910 B2
(45) Date of Patent: Apr. 25, 2017

(54) USE OF TH9 CELLS AND IL-9 FOR THE TREATMENT OF MELANOMA

(75) Inventors: Thomas S. Kupper, Belmont, MA (US); Rahul Purwar, Arlington, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 261 days.

(21) Appl. No.: 14/004,438

(22) PCT Filed: Mar. 22, 2012

(86) PCT No.: PCT/US2012/030104
§ 371 (c)(1),
(2), (4) Date: Oct. 30, 2013

(87) PCT Pub. No.: WO2012/129394
PCT Pub. Date: Sep. 27, 2012

(65) Prior Publication Data
US 2014/0186295 A1    Jul. 3, 2014

Related U.S. Application Data

(60) Provisional application No. 61/466,182, filed on Mar. 22, 2011.

(51) Int. Cl.
| | | |
|---|---|---|
| A61K 45/00 | (2006.01) |
| A61K 38/00 | (2006.01) |
| A61K 38/16 | (2006.01) |
| A61K 39/395 | (2006.01) |
| A61K 38/20 | (2006.01) |
| A61K 35/17 | (2015.01) |
| A61K 31/7088 | (2006.01) |
| A61K 31/7105 | (2006.01) |
| A61K 31/145 | (2006.01) |
| A61K 31/19 | (2006.01) |
| A61K 31/426 | (2006.01) |
| A61K 31/704 | (2006.01) |
| A61K 35/12 | (2015.01) |

(52) U.S. Cl.
CPC ........ *A61K 39/3955* (2013.01); *A61K 31/145* (2013.01); *A61K 31/19* (2013.01); *A61K 31/426* (2013.01); *A61K 31/704* (2013.01); *A61K 31/7088* (2013.01); *A61K 31/7105* (2013.01); *A61K 35/12* (2013.01); *A61K 35/17* (2013.01); *A61K 38/206* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. | 424/450 |
| 5,830,454 A | 11/1998 | Renauld et al. | |
| 5,872,103 A | 2/1999 | Belletti | |
| 7,691,377 B2 | 4/2010 | Goydos et al. | |
| 2003/0035790 A1 | 2/2003 | Chen et al. | |
| 2008/0220006 A1 | 9/2008 | Noelle et al. | |
| 2008/0299134 A1 | 12/2008 | Reed et al. | |
| 2009/0047277 A1 | 2/2009 | Reed et al. | |
| 2009/0148403 A1 | 6/2009 | Bosivert et al. | |
| 2010/0247547 A1 | 9/2010 | Dong et al. | |

FOREIGN PATENT DOCUMENTS

| | | |
|---|---|---|
| WO | 01/54714 | 8/2001 |
| WO | 2007044450 A2 | 4/2007 |

OTHER PUBLICATIONS

Lu et al. Utilizing Th9 cells as a novel therapeutic strategy for malignancies. Oncoimmunology. 2:3, e23084, Mar. 2013.*
Glimelius et al. IL-9 expression contributes to the cellular composition in Hodgkin lymphoma. Journal of Haematology. 2006; 76: 278-283.*
Heppner et al. Tumor heterogeneity: biological implications and therapeutic consequences. Cancer Metastasis Review 2:5-23; 1983.*
Jain RK. Barriers to drug delivery in solid tumors. Scientific American, Jul. 1994, 58-65.*
Glimelius et al., Eur. J. Haematol., 76:278-283 (2006). "IL-9 Expression Contributes to the Cellular Composition in Hodgkin Lymphoma."
Nagato et al., Clin. Cancer Res., 11(23):8250-8257 (2005). "Expression of Interleukin-9 in Nasal Killer/T-Cell Lymphoma Cell Lines and Patients."
Neto, C.C., Chapter 2 from the book "Berries and Cancer Prevention" by Stoner, G.D. and Seeram, N.P., pp. 41-50 (2011). "Ursolic Acid and Other Pentacyclic Triterpenoids: Anticancer Activities and Occurrence in Berries."
Renauld et al., Cancer Investigation, 11(5):635-640 (1993). "Interleukin-9: A T-Cell Growth Factor with a Potential Oncogenic Activity."
Arteaga, "Inhibition of TGFbeta signaling in cancer therapy", Curr. Opin. Genet. Dev. 16:30-37 (2006).
Miyazawa et al., "Recombinant Human Interleukin-9 Induces Protein Tyrosine Phosphorylation and Synergizes With Steel Factor to Stimulate Proliferation of the Human Factor-Dependent Cell Line, M07e", Blood 80(7):1685-1692 (1992).
Xu et al., "Ursolic Acid Suppresses Interleukin-17 (IL-17) Production by Selectively Antagonizing the Function of RORgamma t Protein", J. Biol. Chem. 286(26):22707-22710 (2011).

* cited by examiner

*Primary Examiner* — Vanessa L Ford
*Assistant Examiner* — Sandra Dillahunt
(74) *Attorney, Agent, or Firm* — Nixon Peabody LLP; David S. Resnick; Candace M. Summerford

(57) ABSTRACT

Described herein are methods for the treatment of cancer (e.g. melanoma, lung cancer, or other cancers). The methods involve administrating to a subject in need thereof an agonist of the IL-9 receptor (e.g. IL-9), e.g. an agent that binds and activates the IL-9 receptor, or an agent that increases IL-9 expression in the subject (e.g. administration of TH9 cells that express IL-9, or administration of an inhibitor of ROR).

4 Claims, 24 Drawing Sheets

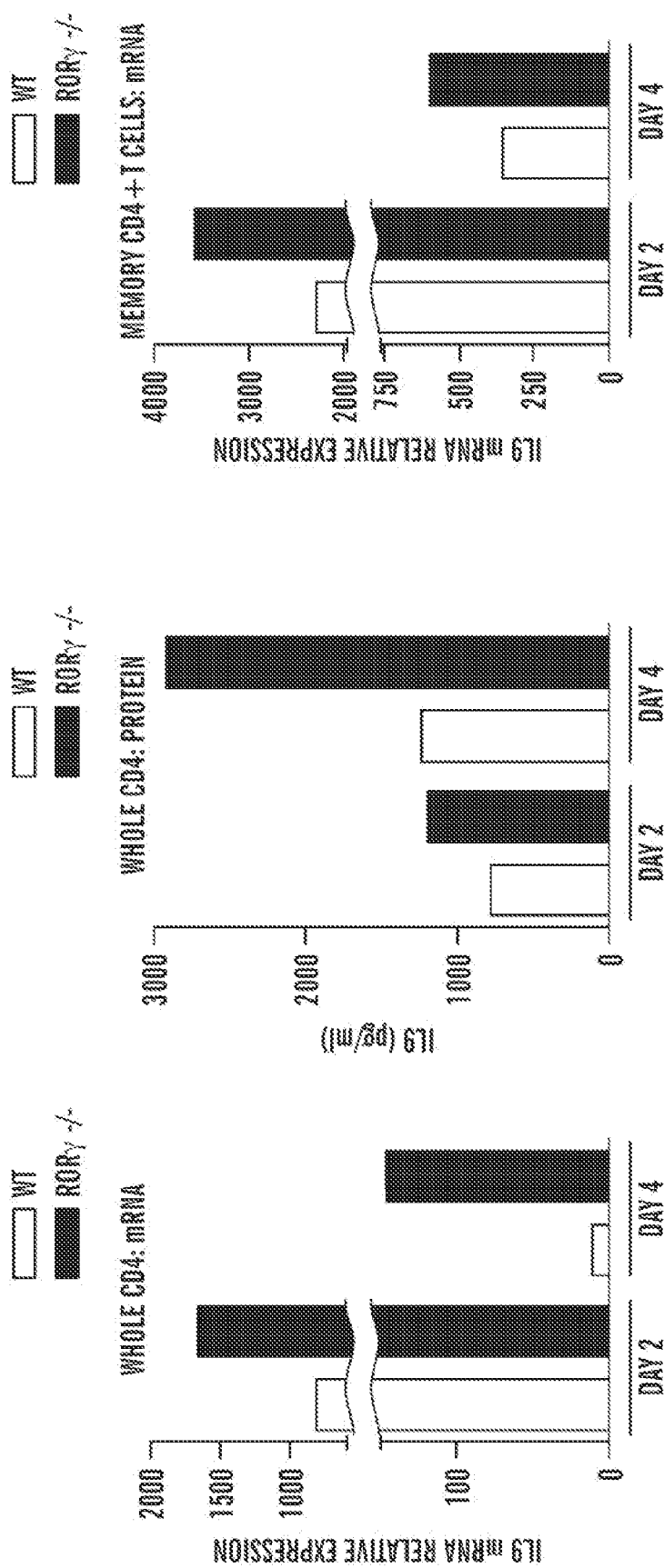

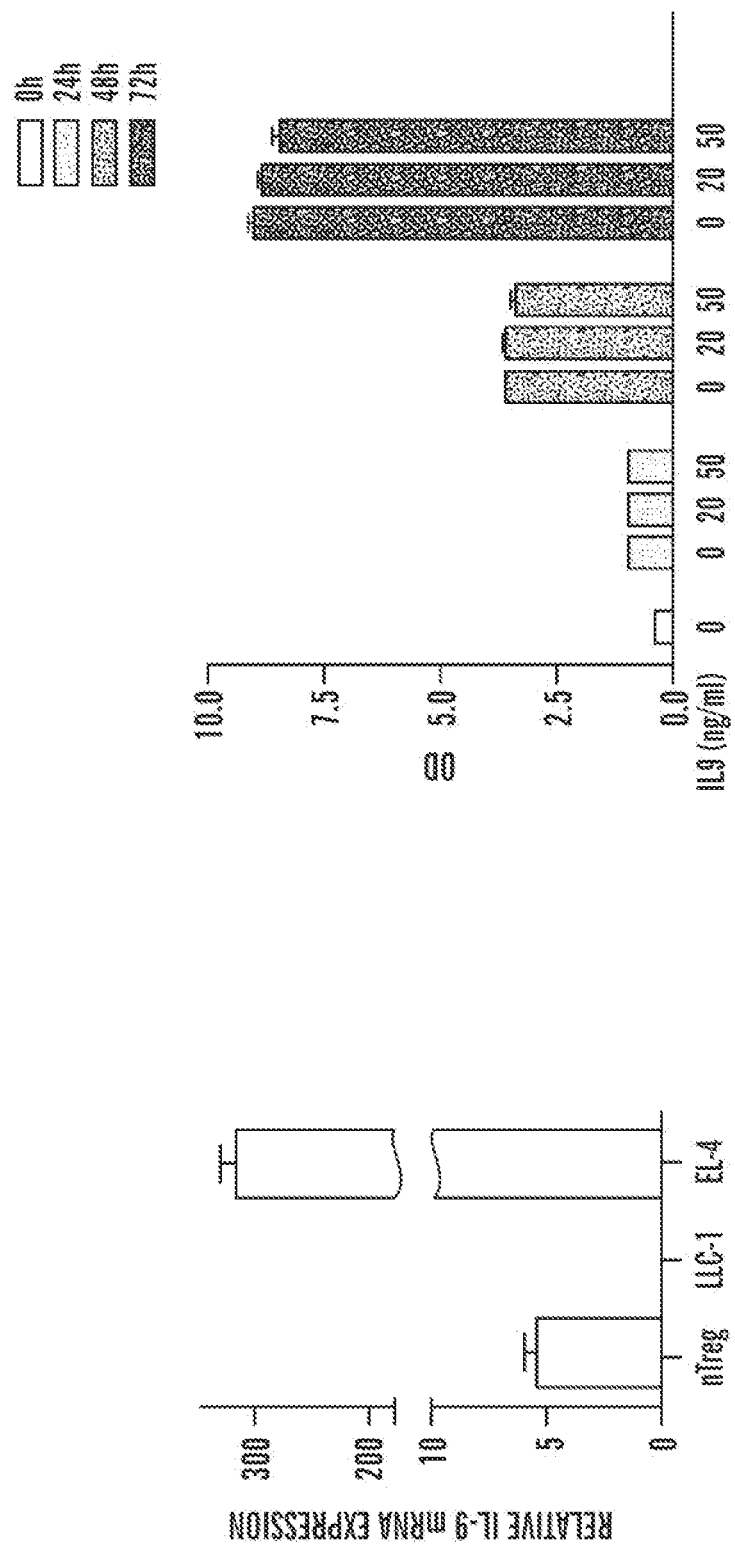

ID  # USE OF TH9 CELLS AND IL-9 FOR THE TREATMENT OF MELANOMA

CROSS REFERENCE TO RELATED APPLICATIONS

This Application is a 35 U.S.C. §371 National Phase Entry Application of International Application No. PCT/US2012/030104 filed Mar. 22, 2012, which designates the U.S., and which claims the benefit under 35 U.S.C. §119(e) of U.S. Provisional Application No. 61/466,182, filed Mar. 22, 2011, the contents of each of which are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Sep. 10, 2013, is named 043214-070052_SL.txt and is 53,716 bytes in size.

FIELD OF INVENTION

The present disclosure relates to compositions and methods for the treatment of cancer (e.g. melanoma, lung cancer, or other cancers). The methods involve administrating to a subject in need thereof an agonist of the IL-9 receptor (e.g. IL-9), e.g. an agent that binds and activates the IL-9 receptor, or an agent that increases IL-9 expression in the subject (e.g. administration of IL-9 producing T cells such as tumor specific TH9 cells that express IL-9, or administration of an inhibitor of RORγ).

BACKGROUND OF THE INVENTION

Even though tumors originate from normal cells, the immune system often reacts relatively strongly against tumor cellular components. However, because the tumors closely resemble the original cells, the immune system tolerates many tumor types to a variable degree. Thus, the very nature of tumor immunity poses enormous challenges to harnessing the immune system for the therapy of cancers. Recent studies have indicated that immunologic targeting of cancer is a promising strategy (Hodi, F. S., et al. *N Engl J Med* 363, 711-723 (2010)); however, how best to achieve this goal is incompletely understood.

The use of mouse melanoma models is a convenient way to study tumor immunity. Melanoma is a malignant tumor of melanocytes. Primarily melanoma is a skin tumor, but it is also seen, though less frequently, in the melanocytes of the eye (uveal melanoma). Even though melanoma represents one of the rarer forms of skin cancer, it underlies the majority of skin cancer-related deaths. Yet despite many years of intensive laboratory and clinical research, there are still limited treatments for melanoma, and the treatments exhibit resistance and multiple unwanted side effects including back pain, constipation, cough, diarrhea, dizziness, dry skin, hair loss, headaches, joint or muscle pain, loss of appetite; nausea, taste changes, thickening of the skin, tiredness, vomiting, weakness, and severe allergic reaction (e.g. Zelboraf™ (Vemurafenb or PLX4032: Hoffman-La-Roche (Madison Wis.)/Daiichi Sankyo (Parsippany, N.J.)).

Thus, there is a need for a better understanding of tumor immunity in order to facilitate efficient harnessing of this aspect of immune system as an effective therapy for the treatment of cancer.

SUMMARY

Embodiments of the disclosure are based on the discovery that IL-9 promotes tumor immunity and inhibits cancer growth. We have evaluated the role of Th17 transcription factor retinoid-related orphan receptor-gamma (RORγ) in tumor immunity and determined that RORγ−/− and IL-23R−/− mice exhibit significant growth inhibition of B16F10 melanoma, with evidence for increased anti-melanoma immune responses (tumor lymphocyte infiltration and increased cytokine expression). In parallel, transcriptional profiling experiments revealed the expected severely impaired IL-23R and IL-17A expression in RORγ−/− CD4+T cells differentiated under Th17 polarizing conditions. Unexpected, however, was a dramatic increase in the expression of IL-9 in these CD4+T cells.

Our studies demonstrate that it is IL-9 that has an inhibitory effect on tumor growth in both normal and RORγ−/− or IL-23R−/− mice. Neutralizing IL-9 antibody abrogated the growth inhibition observed in both RORγ−/− and IL-23R−/− mice. In addition, melanoma growth accelerated in normal mice treated with neutralizing antibodies to IL-9, and this effect was further enhanced in mice lacking the receptor for IL-9 (IL-9R−/−). Adoptive transfer of polarized IL-9 producing CD4$^+$ T cells (i.e. Th-9 cells) inhibited melanoma growth in both normal and lymphopenic hosts; an effect that was also blocked significantly by anti-IL-9 neutralizing Ab. Furthermore, treatment of melanoma bearing mice with exogenous recombinant IL-9 (rIL-9) inhibited tumor growth and exogenous rIL-9 similarly inhibited the growth an unrelated syngeneic tumor (Lewis lung carcinoma) in normal mice. Thus, IL-9 effects tumor growth of multiple cancers through enhancing tumor immunity.

Accordingly, provided herein are methods for treating or preventing cancer comprising administrating to a subject in need thereof (i.e. diagnosed with, or at risk of having cancer), a therapeutically effective amount of an agonist of the interleukin-9 receptor (IL-9R), (e.g. IL-9). The agonist of the IL-9 receptor (IL-9R) may be a small molecule, a nucleic acid RNA, a nucleic acid DNA, a protein, a peptide, a cell, and an antibody.

In one aspect, the agonist comprises an agent that binds the IL-9 receptor. Any agent that binds and activates the IL-9R may be used in the methods described herein.

In one embodiment, the agent that binds the IL-9 receptor comprises the cytokine interleukin 9 (IL-9), or fragment thereof, e.g. human recombinant interleukin-9 (rIL-9); KP-20 peptide, or KP-89 peptide. In some embodiments, the agent that binds the IL-9 receptor may be an activating monoclonal antibody, or small molecule compound.

In another aspect, the agonist comprises an agent that increases expression of IL-9 in the subject as compared to IL-9 expression in the absence of the agonist. For example, in one embodiment, the agonist comprises a population of cells that express IL-9, such as a population of cells that comprises Th9 cells, or comprises other cells that express IL-9.

In an alternative embodiment, the agent that increases expression of IL-9 in the subject as compared to IL-9 expression in the absence of the agonist comprises an inhibitor of RORγ. Any inhibitor of RORγ may be used in the methods described herein. In one embodiment, the inhibitor of RORγ comprises siRNA. In an alternative embodiment, the inhibitor of RORγ is selected from the group consisting of: ursolic acid, digoxin, SR1001, and TO901317.

The agonist of the IL-9R used in the methods described herein may further comprise a pharmaceutically acceptable carrier and may be administered using any suitable means of administration known to those of skill in the art. In one embodiment, the agonist may be administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, adoptive cell transfer, and parenteral administration.

Any cancer may be treated using the methods described herein. In one embodiment, the cancer is selected from the group consisting of gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer.

The methods described herein can be used either alone, or in conjunction with other treatment methods known to those of skill in the art. For example, such methods may include, but are not limited to, chemotherapy, radiation therapy, or surgery.

In one embodiment, the subject may be at risk for developing cancer and the IL9-R agonist is administered prophylactically. The risk can be determined genetically. Alternatively, the risk can be determined by measuring levels of biomarker proteins in the biological fluids (i.e. blood, urine) of a patient.

In one embodiment, the methods of treatment described herein further comprises the step of selecting a subject in need thereof of treatment, e.g. selecting a subject diagnosed with cancer, or a subject at increased risk of cancer (e.g. potential cancer relapse).

In some embodiments of the methods described herein, wherein the subject is administered an agonist of the IL-9R, the subject is not additionally administered a co-stimulatory molecule activating agent, e.g. an agent that increases the concentration of a cytokine in a subject, is not administered to the subject in addition to the agonist of the IL-9R.

In another aspect, methods for the prognosis of cancer (e.g. melanoma or other cancers) in a subject are provided. The methods comprise assaying a tumor for the presence of IL-9 producing T cells, wherein the presence of reduced levels of IL-9 producing T-cells (e.g. Th9 cells) within the tumor as compared to the level of IL-9 producing T-cells (e.g. Th9 cells) in normal skin is indicative of increased metastatic potential and a poor prognosis. In one embodiment, the reduced level of IL-9 producing T-cells indicates a treatment protocol for the subject comprising administrating to the subject in need thereof an agonist of the IL-9 receptor (e.g. IL-9), e.g. an agent that binds and activates the IL-9 receptor, or an agent that increases IL-9 expression in the subject (e.g. administration of IL-9 producing T cells, such as tumor specific TH9 cells that express IL-9, or administration of an inhibitor of RORγ). In certain embodiments, an increased level of RORγ expression in T cells present within a tumor serves as an indicator that the cancer may be treatment with an inhibitor of RORγ.

BRIEF DESCRIPTION OF FIGURES

FIG. 1C demonstrates that tumor infiltrating lymphocytes (TILs) were recovered and counted as described in methods. FIG. 1D demonstrates that tumor draining LNs were isolated and restimulated with PMA plus ionomycin for 6 h in presence of golgistop. Expression of IL-17A, IFN-γ, and TNF-α by CD4+ and CD8+T cells was analyzed by flow cytometry. Data is represented as Mean±SEM in a, b (n=8 mice per group (p<0.005: *), in c (TILs from 4 mice were pooled and analyzed) and in d (n=8 mice per group, p<0.005: *, p<0.025: **). Two-three additional independent experiments provided similar results.

FIG. 3A demonstrates that B16F10 melanoma cells were injected subcutaneously into RORγ−/− ch, and control mice (RORγ+/+ch). Anti-IL-9 neutralizing antibody was administered (i.p.) to RORγ−/− ch mice. FIG. 3B depicts the results when sorted naive Th cells (CD4+ CD25-CD62Lhigh) from IL-23R+/+ and IL-23R−/− mice were differentiated under Th17 polarizing conditions. After 4 days, cells were harvested and restimulated with plate bound anti-CD3/CD28 for 48 h. IL-9 and IL-17A were estimated by ELISA in cell free supernatants. FIG. 3C depicts the results when B16F10 melanoma cells were injected subcutaneously into IL-23R−/− and their controls. Anti-IL-9 neutralizing antibody was administered (i.p.) to both IL-23R+/+ and IL-23R−/− mice. Melanoma growth was monitored over time. FIG. 3D depicts the results when tumor draining lymph node cells (LNCs) from IL-23R+/+ (WT) and IL-23R−/− mice were isolated and stimulated with plate bound anti-CD3 (2 μg/ml)/anti-CD28 mAbs (1 μg/ml). After 48 h, culture supernatant was collected and IL-9 and IL-17 were estimated by ELISA. Data is represented as Mean±SEM and statistically significant differences were observed compared to controls (p<0.005: *, p<0.025: , p<0.05: *). Two additional independent experiments produced similar results.

(FIG. 4A) or Rag1−/− C57BL/6 mice (FIG. 4B-4C). On the same day, B16F10-ova cells were injected subcutaneously. Melanoma growth was monitored over time (FIGS. 4A-4C). Neutralizing anti-IL-9 mAb or isotype was given (IP) to OT2-Th9 treated mice (FIG. 4B). Data is represented as Mean±SEM (FIGS. 4A-4C) and statistically significant differences were observed compared to no-T cells group (FIG. 4A), and as depicted (FIGS. 4B-4C) (p<0.005: *, p<0.025: , p<0.05: *).

In FIGS. 5A, 5B, 5D, and 5E B16F10 melanoma cells were injected subcutaneously into IL-9R−/− and controls (IL-9R−/+) mice (FIG. 5A), normal WT mice (FIG. 5B) and Rag1−/− mice (FIG. 5D) and Kit W-sh (mast cell deficient) mice (FIG. 5E). In FIGS. 5C and 5F, Lewis lung carcinoma cells were injected subcutaneously into normal WT mice (FIG. 5C) and Kit W-sh (mast cell deficient) mice (FIG. 5F). Where indicated, rIL-9 was administered (i.p.). Control mice received PBS. Tumor growth was monitored over time. Data is represented as Mean±SEM (n=4 mice per group, 2-4 additional independent experiment produced similar results, and statistically significant differences were observed compared to controls (p<0.025: **, p<0.05: *, ns: not significant).

In FIGS. 6A-6B, memory T cells (CD4+CD45RO+) from peripheral blood after stimulation with anti-CD3/CD28 mAbs plus TGF-β and skin-resident T cells isolated by skin-explant culture of healthy donors were stained for IL-9, IFNγ, IL-17 and IL-4 and analyzed by flow cytometry. In FIG. 6C, memory T cells (CD4+CD45RO+) from peripheral blood of healthy donors, skin T cells from healthy donors and tumor-infiltrating lymphocytes of metastatic melanoma were extracted and stimulated for 2 days with anti-CD3/CD2/CD28 beads in the presence of IL-2 plus TGF-β. IL-9 production was measured in cell free supernatants by luminex assay. Data is represented as Mean±SEM (skin: n=8, PBMCs: n=3, MM: n=8).

FIG. 8C depicts FACS analysis of these cells.

FIGS. 9A-9H depict IL9 expression in RORγ−/− Th2 and Th9 cells. Sorted CD4+T cells (FIGS. 9A and 9B), sorted CD4+CD25-CD62Llow cells (memory CD4+T cells, FIGS. 9C-9E), and sorted CD4+CD25-CD62Lhigh+ cells (naïve CD4+T cells, FIG. 9F) from spleen of WT and RORγ−/− mice were stimulated with plate bound anti-CD3 (2 µg/ml) and anti-CD28 Abs (1 µg/ml). After 2 and 4 days, cells were analyzed for IL9 mRNA expression by real-time RT-PCR (FIGS. 9A, 9C) and supernatant was estimated for IL9 secretion by CBA (FIGS. 9B, 9E and 9F). In FIG. 9D, memory CD4+T cells were re-stimulated with PMA plus ionomycin in presence of golgi-stop for 6 h. IL9 was stained and analyzed by flow cytometry. A representative data set is depicted. Two to three additional experiments provided similar results. In FIGS. 9G-9H, sorted naïve CD4+T cells from WT and RORγ−/− mice were differentiated under Th2 and Th9 polarizing condition. After 2 and 4 days, supernatant was collected and IL9 was quantified by CBA (FIGS. 9G and 9H).

FIGS. 10A-10E depict antitumor effects of IL-9 in vaccinated mice, IL-9R expression on tumor cells and effect of rIL9 on tumor cell growth. In FIG. 10A, B16F10 melanoma cells were injected subcutaneously into vaccinated normal WT mice. Mice were treated with IL-9 or PBS. Tumor growth was monitored over time. (FIGS. 10B-10C) IL-9R expression was quantified using Taqman real-time RT PCR. Data is represented as Mean±SEM. In FIG. 10D, rIL-9 was added at different concentrations into the B16F10 tumor cell culture and tumor cell growth was measured at indicated time points as described in methods. In FIG. 10E, TILs were isolated from tumor growing in WT mice. IL-9 was stained and quantified by flow cytometry.

FIG. 11A depicts the results of an experiment in which sorted CD4+CD25-CD62Lhigh (naive CD4+T cells) from OT2 mice were polarized towards Th0, Th1, Th2, Th9 and Th17 as described in method section. Intracellular cytokine expression was analyzed by flow cytometry before adoptive transfer into mice. In FIG. 11B, IL-9, IFNg, GranzymeB and IL-10 was quantified at mRNA level in differentiated Th9 cells using quantitative RT-PCR (qPCR).

FIG. 12A depicts the results of an experiment in which OT2-Th0, OT2-Th9 c, or OT2-Th17 cells were incubated with B16F10-ova cells for 24 h. B16F10-ova cell lysis was quantified by 7AAD staining FIG. 12B depicts the results of an experiment in which OT2-Th9 cells were pre-incubated (30 min) with granzyme-B inhibitor or control (DMSO) before co-culture with B16F10 ova cells. After 24 h, B16F10-ova cell lysis was quantified by 7AAD staining. Data is represented as percentage inhibition. Th9 cell cytotoxicity was considered as 100%. FIG. 12C depicts the results of an experiment in which CFSE labeled B16F10-ova cells (5 µM) and EL-4 cells (0.5 µM) were incubated with different effector/target ratio (E/T ratio: as indicated) with or without OT2-Th0, and OT2-Th9 cells for 36 h. Tumor cell lysis was measure as described in methods.

DETAILED DESCRIPTION

Figure 1A:
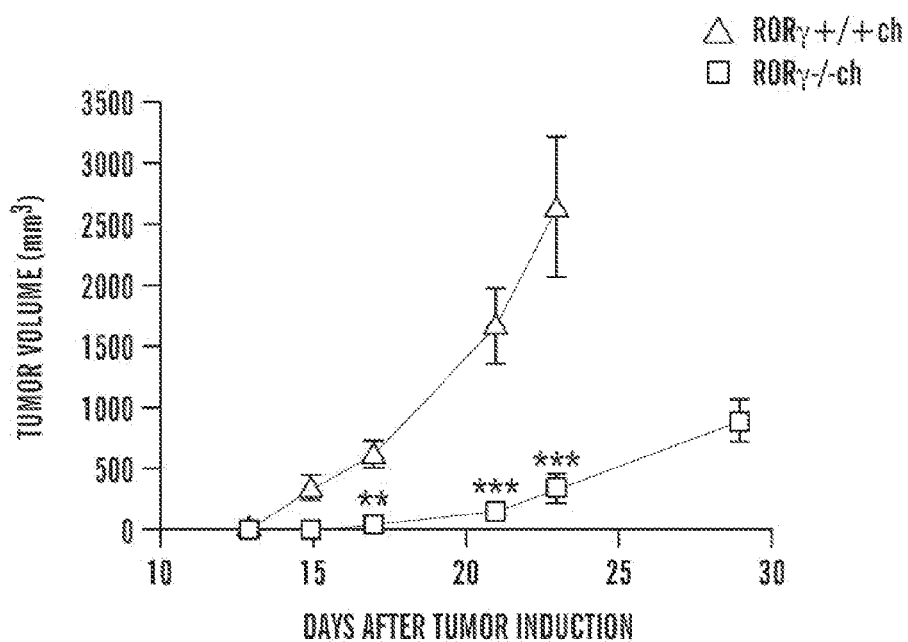
FIGS. 1A-1D depict the results of experiments in which B16F10 melanoma cells were injected subcutaneously into RORγ−/− ch and RORγ+/+ ch mice. Tumor growth (FIG. 1A) and mice survival (FIG. 1B) was monitored over time.

Described herein are methods for treating cancer in a subject that has, or at risk of having, cancer. The methods comprise administration to a subject a therapeutically effective amount of an agent that is an agonist of the IL-9 receptor (IL-9R).

As used herein, the term "IL-9 receptor" or "IL-9R" refers to the transmembrane protein that is the cell surface receptor for interleukin 9 (IL-9). The IL9-R is a two subunit receptor. The first subunit is the common gamma chain or IL2RG (e.g. NCBI Gene ID: 3561; SEQ ID NO: 6 (*Homo Sapiens*)), which is a shared component of the receptor complexes for at least IL-2, IL-4, IL-7, IL-13, and IL-15. The human IL2RG polypeptide is e.g. encoded by the cDNA of SEQ ID NO: 5. The second subunit of the IL-9 receptor is e.g. the IL-9R protein (NCBI Gene ID: 3581; SEQ ID NO: 4 (*Homo Sapiens*)) which provides specificity for IL-9. The extracellular domains of human and murine IL-9R have 67% homology, while the cytoplasmic regions are less conserved. The IL9-R is 522 amino acids. The IL-9R polypeptide is e.g. encoded by the cDNA of SEQ ID NO: 3 (*Homo Sapiens*). IL-9R mediated signal transduction is initiated when the IL-9 polypeptide is recognized by the IL-9 receptor expressed on the surface of a target cell. Embodiments of the invention encompass homologs and variants of the IL-9 receptor described herein.

IL9-R Agonists

As used herein, the term "agonist" refers to any agent that activates or increases activity mediated by the IL-9 receptor (IL-9R). Thus, the term "IL-9R agonist" includes any agent that activates the IL-9R or increases IL-9R activity in comparison to IL-9R activity in the absence of the agonist. An IL-9R agonist may be an agent that binds to the IL-9R thereby inducing signal transduction mediated by the receptor (e.g. the cytokine interleukin 9 (IL-9), or an agent that mimics IL-9), also known as a direct agonist. Alternatively, the IL-9R agonist may be an agent that increases IL-9 expression in a subject, also known as an indirect agonist (e.g. Th9 cells administered by adoptive transfer express IL-9, or administration of transforming growth factor beta (TGFβ) and interleukin-4 (IL-4)). In certain embodiments, the IL-9R agonist is an agent that induces the activity of a downstream signaling molecule that is activated by the IL-9R.

As used herein, the terms "activity mediated by the IL-9 receptor" and "IL-9R activity" refers to IL-9 receptor (IL-9R) mediated signal transduction. An agent that "activates the IL-9R" is an agent that stimulates IL-9 receptor (IL-9R) mediated signal transduction. Signal transduction mediated by the IL-9R is known to involve, for example, tyrosine phosphorylation of STAT3 which is unique to the IL-9 pathway, and expression of IL-9 specific marker genes including but not limited to TH2AF1 (SEQ ID NOs: 7-8 and described in US Patent Publication US 2008/009%981, which is incorporated by reference herein in its entirety) and ICACC (also CLCA2, SEQ ID NOs: 9-10; described in U.S. Pat. No. 6,716,603, which is incorporated by reference herein in its entirety). Means for assaying IL-9R activity are well known to those of skill in the art. For example, an increase in expression of TH2AF1 or ICACC, at either the mRNA or protein level can indicate activation of IL-9 signaling in a cell. Reporter gene constructs can be useful in such assays. For example, the promoter of TH2AF1 can be coupled to the protein coding sequence of a detectable reporter gene (e.g. GFP) and the expression of the reporter gene detected by, e.g. a fluorescence detector. IL-9 receptor signal transduction activates STAT 1, STAT3 and STAT5 transcription factors. Guidance for assays for IL-9R activity may also found in Goswami and Kaplan (2011), A brief history of IL-9 *Journal of Immunology* vol. 186 no. 6 3283-3288.

As used herein, the term "IL-9R selective agonist" refers to an IL-9R agonist that activates the IL-9R to a significantly greater degree than it stimulates any other receptor, e.g. cytokine receptor. In one embodiment, the agent acts as an agonist of the IL-9R and for no other cytokine receptor. In one embodiment, the IL-9R agonist acts primarily as an agonist of IL9-R, but also induces minor levels of activity mediated by another cytokine receptor.

Any agent that acts as an agonist of the IL-9R can be used in the methods described herein, e.g. administered to a subject for the treatment of cancer.

As used herein, the terms "compound" or "agent" are used interchangeably and refer any organic or inorganic molecule, including modified and unmodified nucleic acids such as antisense nucleic acids, RNAi, such as siRNA or shRNA, peptides, small molecules peptidomimetics, receptors, ligands, and antibodies. The agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies, or fragments thereof. The agent may activate the IL-9 receptor directly (e.g. the cytokine IL-9), or may activate the IL-9 receptor indirectly, e.g. by inhibition of ROR gamma activity, by modulating a downstream signaling molecule of the IL-9R, or by increasing expression of IL-9 in a subject.

An agonist agent can be a nucleic acid RNA or DNA, and can be either single or double stranded. Example nucleic acid agents include, but are not limited to, a nucleic acid encoding a protein inhibitor (e.g. transcriptional inhibitors), oligonucleotides, nucleic acid analogues (e.g. peptide-nucleic acid (PNA), pseudo-complementary PNA (pc-PNA), locked nucleic acid (LNA) etc.), antisense molecules, ribozymes, small inhibitory or activating nucleic acid sequences (e.g. RNAi, shRNAi, siRNA, micro RNAi (mRNAi), antisense oligonucleotides etc.).

An agonist protein and/or peptide agent can be any protein that increases IL-9R activity as compared to IL-9R activity in the absence of the agonist, and may be for example a protein or peptide that modulates gene expression or a protein/peptide that modulates protein activity. Non-limiting examples include mutated proteins; therapeutic proteins and truncated proteins, e.g. wherein the protein is normally absent or expressed at lower levels in the target cell. Proteins can also be selected from genetically engineered proteins, peptides, synthetic peptides, recombinant proteins, chimeric proteins, or antibodies.

Any agonist of IL-9R can be used in methods described herein. The agonists may be direct or indirect agonists.

In one embodiment, the agent is a direct agonist of IL-9R, i.e. the agonist binds to the IL-9R and activates the receptor. For example, in one embodiment, the agonist comprises the cytokine interleukin-9 (IL-9), or fragment thereof, such as natural or recombinant interleukin 9 (rIL-9). Example direct agonist, include but are not limited to: IL-9; the IL-9 peptide KP-20 (SEQ ID NO:15) or KP-89 (SEQ ID NO: 16) (described in International Patent Publication WO/1998/027997; which is incorporated herein by reference in its entirety).

As used herein, "IL-9" refers to a 4-helix bundle cytokine that is produced by T-cells, specifically by CD4+ helper cells (e.g. activated Th2 cells, or Th9 cells). Alternative names for IL-9 include, but are not limited to, P40, HP40, T-cell growth factor p40, interleukin-9, or P40 cytokine IL-9 acts as a regulator of a variety of hematopoietic cells and is known to stimulate cell proliferation and prevent apoptosis. IL-9 functions through the interleukin-9 receptor (IL-9R), which activates different signal transducer and activator (STAT) proteins. Both human (e.g. Gene ID: 3578; SEQ ID NO: 2, Gene bank Accession NP_000581.1) and murine IL-9 protein sequences contain 144 residues with a signal peptide of 18 amino acids. The IL-9 protein is encoded e.g. by the cDNA of SEQ ID NO: 1, Gene bank Accession NM_000590.1. IL-9 is expressed by activated T cells and mast cells and can function as a T cell growth factor. Further, IL-9 mediates the growth of erythroid progenitors, B cells, mast cells, eosinophils, and fetal thymocytes, and acts synergistically with interleukin-3 ("IL-3") to induce mast cell activation and proliferation. IL-9 further promotes the production of mucin by lung epithelium. In addition, IL-9 potentiates the IL-4 induced production of IgE, IgG, and IgM by normal human B lymphocytes, and the IL4 induced release of IgE and IgG by murine B lymphocytes. Embodiments of the invention encompass use of homologs and variants of the IL-9 cytokine described herein.

In some embodiments, IL-9R activity may be increased in a subject by administering an IL-9 polypeptide agonist to the subject. An IL-9 polypeptide administered to a subject according to the methods described herein can be human IL-9 or a homologue, variant, conservative substitution, or functional fragment thereof. By way of non-limiting example, the IL-9 amino acid sequences are known for at least mouse, rat, and chimpanzee. One of ordinary skill in the art is familiar with how to align homologous peptide sequences to determine which amino acid residues are particularly conserved. IL-9 variants can include the mature version of IL-9 lacking the signal peptide, i.e. an IL-9 variant can be amino acids 19-144 of SEQ ID NO: 2.

In some embodiments, the IL-9 polypeptide may be recombinant, i.e. expressed in an organism which does not naturally produce IL-9, or variant of IL-9. Means for making recombinant IL-9 (rIL-9) are well known to those of skill in the art, e.g. as described in U.S. Pat. No. 5,581,753, herein incorporated by reference in its entirety, e.g. U.S. Pat. No. 5,581,753 describes DNA encoding the human cytokine interleukin-9 as well as means for expressing and purifying recombinant IL-9. Alternatively, recombinant IL-9 can be obtained from commercial sources (e.g. recombinant human or mouse IL-9 may be obtained from PRO SPEC protein specialists of Ness-Ziona, Israel; or Cell Sciences of Canton, Mass.). In one embodiment, the IL-9 is isolated from culture conditioned medium of mitogen- or antigen-stimulated T-helper cells. In cultures of primary lymphocytes, IL-9 is produced predominantly by cells expressing CD4. The synthesis of IL-9 can be induced by Phorbol esters and Calcium ionophore.

In some embodiments, IL-9R activity may be increased in a subject by administering an agonist cDNA or nucleic acid analog that encodes a IL-9 polypeptide (e.g. a nucleic acid of SEQ ID NO: 1). The nucleic acid encoding an IL-9 polypeptide may comprise a vector. In some embodiments, the nucleic acid encoding an IL-9 polypeptide further comprises an expression vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

In some embodiments, the agonist of IL-9R comprises an antibody. The antibody agonist may be a direct or indirect agonist. As used herein the term "antibody" refers to immunoglobulin molecules and immunologically active determinants of immunoglobulin molecules, e.g., molecules that contain an antigen binding site which binds, e.g. specifically binds, (immunoreacts with) a protein to be activated or inhibited in order to increase the activity of the IL-9R, (e.g. immunoreacts with the IL-9R). The term "antibody" encompasses whole antibodies, e.g., of any isotype (IgG, IgA, IgM, IgE, etc), and includes fragments thereof which are also reactive with IL-9R protein. Antibodies can be fragmented using conventional techniques, e.g. proteolytically-cleaved or recombinantly-prepared portions of an antibody molecule that are capable of reacting with the particular protein of interest. Non limiting examples of such proteolytic and/or recombinant fragments include Fab, F(ab')2, Fab', Fv, dAbs, diabodies, and single chain antibodies (scFv) containing a VL and VH domain joined by a peptide linker. The scFv's may be covalently or non-covalently linked to form antibodies having two or more binding sites, e.g. divalent, trivalent, tetravalent etc. The antibodies may be polyclonal or monoclonal, or other purified preparations of antibodies and recombinant antibodies, e.g. humanized antibodies, bispecific antibodies, and chimeric molecules having at least one antigen binding determinant derived from an antibody molecule.

In an alternative embodiment, the agonist comprises an agent that is an indirect agonist of the IL-9 receptor, i.e. the agent does not directly bind to the IL-9R and increases the activity of the receptor indirectly (e.g. by modulating downstream IL-9R signal transduction molecules, by increasing expression of IL-9 in the subject, or by inhibiting antagonists of IL-9R signal transduction).

In some embodiments, the indirect agonist increases the amount of IL-9 in the subject, which in turn activates the IL-9R. We have discovered a role for Th17 transcription factor retinoid related orphan receptor-gamma (ROR-γ) in the increase in production of IL-9 (See Examples). Thus, in one embodiment the agonist used herein comprises an agent that comprises an inhibitor of RORγ. As used herein "Th17 transcription factor retinoid related orphan receptor-gamma (ROR-γ)", or "RORγ" refers to a DNA-binding transcription factor that is a member of the NR1 subfamily of nuclear receptors. The transcription factor plays an important regulatory role in thymopoiesis, e.g. by reducing apoptosis of thymocytes and promoting thymocyte differentiation into pro-inflammatory T helper 17 (Th17) cells. The RORγt isoform of RORγ is specific for T cells and promotes development of TH17 cells. The RORγ isoform (SEQ ID NO: 12) is e.g. encoded by the cDNA of SEQ ID NO: 11 while the RORγt isoform (SEQ ID NO: 14) is e.g. encoded by the cDNA of SEQ ID NO: 13. Embodiments of the invention encompass use of homologs and variants of "RORγ" described herein.

As used herein, the phrase "inhibitor of RORγ" refers to an agent that inhibits the biological activity of RORγ, an antagonist. The biological activity of RORγ may be inhibited using an agent that inhibits the transcription regulatory activity of RORγ, or an agent that down regulates expression or availability of RORγ in a cell or organism (e.g. siRNA, shRNA). RORγ biological activity may be assessed using in vitro assays well known to those of skill in the art. In one embodiment, inhibition of RORγ activity is monitored by assaying for inhibition of IL-17 and/or IL-22 production in Th17 cells as an indicator of inhibition of RORγ activity (e.g. by ELISA assay). In alternative embodiments, RORγ activity assayed using cell lines with RORγ reporter constructs that are commercially available, for example Cat Nos. K1883 and K1882 from Invitrogen (Grand Island, N.Y.) (e.g. See and Xu et al. (2011), J. Biol. Chem. 286(26): 22707-22710).

Any inhibitor of RORγ may be used in the methods and compositions described herein. For example, various inhibitors of RORγ are described in Solt et al. (2011) Nature, 472: 491-496, and Xu et al. (2011), J. Biol. Chem. 286(26): 22707-22710, which are herein incorporated by reference in their entirety.

Example RORγ inhibitors include, but are not limited to: antisense RNAs specific for RORγ and/or RORγt; digoxin; Ursolic acid; SR1001 (Structure 1 below)(see Solt et al. Nature 2011 472:491-6); and TO901317 (Structure 2 below).

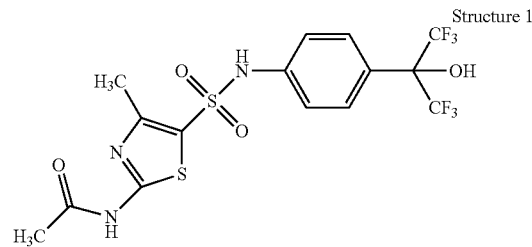

Structure 1

Structure 2

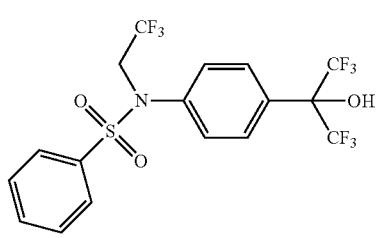

In some embodiments, the indirect agonist that increases expression of IL-9 comprises HTLV-1 Tax a 351 amino acid protein produced by Human T-lymphotropic virus 1 (HTLV-1) (SEQ ID NO: 17) (or comprises a nucleic acid that encodes the protein). HTLV-1 Tax-1 is known to induce expression of IL-9, as described in Chen et al. Blood 2008 111:5163-5172, which is incorporated herein by reference in its entirety.

In an alternative embodiment, the indirect agonist that increases expression of IL-9 in the subject is cellular agent that expresses IL-9, e.g. Th9 cells, or cells genetically engineered to express IL-9.

In some embodiments, IL-9R activity may be increased in a subject by administering cells which produce IL-9, e.g. Th9 cells, to the subject. As used herein, "Th9 cells" are CD4+ T cells which express IL-9 but not IFN-γ, IL-4, IL-5, IL-13 or IL-17. In humans, Th9 cells also do not express IL-10. The differentiation of T cells into Th9 cells can be accomplished in vitro by contacting naïve CD4+ T cells with the combination of TGF-β and IL-4 and activating the cells, or by contacting Th2 T-helper cells with TGF-β. In some embodiments, IL-9 signaling can be increased in a subject by adoptive cell transfer of Th9 cells.

In certain embodiments, a subject in need thereof is administered autologous tumor specific IL-9 producing T-cells (such as, Th9 cells); e.g. cancer specific IL-9 producing cells that are isolated from the subject and expanded in vitro, prior to administration back to patient. In certain embodiments, the autologous cancer specific T cells are isolated from the subject and transformed into IL-9 producing cells, e.g. by overexpression of IL-9, by differentiation using a cytokine cocktails that produce IL-9 producing cells, or by differentiation using other polarizing/differentiation agents.

As used herein, "adoptive cell transfer" is the process of passively transferring cells, particularly immune-derived cells, into a new host with the goal of transferring the immunologic functionality and characteristics into the new host. In some embodiments, IL-9 producing cells are used in adoptive cell transfer according to the methods described herein. In some embodiments, cells comprising a nucleic acid encoding an IL-9 polypeptide are used in adoptive cell transfer according to the methods described herein. In some embodiments, Th9 cells are used in adoptive cell transfer according to the methods described herein.

In some embodiments, the cells administered to the subject are autologous cells. For example, a blood sample can be obtained from a subject and Th2 T-helper cells isolated from the sample. The Th2 T-helper cells can be contacted with TGF-β to convert them to Th9 cells and then administered to the same subject. In one embodiment the Th9 cells are further treated with IL-25 prior to administration to the subject (Angkasekwinai et al. (2010) Regulation of IL-9 expression by interleukin 25 (IL-25) signaling, Nature Immunology 3: 250-257). Methods of isolating Th2 T-helper cells are known to those of skill in the art and include FACS sorting of CD4+ cells. Th2 cells can be differentiated from other CD4+ cells by the expression of CCR4 and Crth2 and the lack of CSCR3, CCR6, CXCR5, or CD25 expression on the cell surface.

In some embodiments, the indirect agonist that increases expression of IL-9 in the subject may be a cytokine or growth factor known to enhance expression of IL-9. In one embodiment, a combination of agonist agents is administered to a subject, e.g. a combination of transforming growth factor beta (TGFβ) and interleukin-4 (IL-4). In one embodiment, the agonist agent is IL-25 (Angkasekwinai et al. (2010) Regulation of IL-9 expression by interleukin 25 (IL-25) signaling, Nature Immunology 3: 250-257, herein incorporated by reference in its entirety).

In addition, agonists for use in the methods described herein may be identified using screening assays. Candidate agonists of the IL-9R can be screened for the ability to activate IL-9R signaling by contacting a cell expressing the IL-9 receptor with the test agent and detecting modulation of IL-9 signaling activity. For example, an increase in expression of TH2AF1 or ICACC, at either the mRNA or protein level can indicate activation of IL-9R signaling in the cell. Reporter gene constructs can be useful in such assays. For example, the promoter of TH2AF1 can be coupled to the protein coding sequence of a detectable reporter gene (e.g. GFP) and the expression of the reporter gene detected by, e.g. a fluorescence detector.

Candidate agents may also be screened for the ability to inhibit RORγ by contacting a cell expressing the RORγ with the test agent and detecting the modulation of the expression of genes which are transcriptionally regulated by RORγ. Cell lines with RORγ reporter constructs are commercially available, for example Cat Nos. K1883 and K1882 from Invitrogen (Grand Island, N.Y.).

As used herein, the terms "test compound" or "test agent" are used interchangeably and refers to compounds and/or compositions that are to be screened for their ability to inhibit the number of neural crest progenitors. The test agents can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; antibodies, nucleic acid analogs and derivatives; an extract made from biological materials such as bacteria, plants, fungi, or animal cells; animal tissues; naturally occurring or synthetic compositions; and any combinations thereof. In some embodiments, the test agent is a small molecule.

As used herein, the term "small molecule" refers to in organic or organic compounds. However, small molecules typically are characterized in that they contain several carbon-carbon bonds, and have a molecular weight of less than 5000 Daltons (5 kD), preferably less than 3 kD, still more preferably less than 2 kD, and most preferably less than 1 kD. In some cases it is preferred that a small molecule has a molecular weight equal to or less than 700 Daltons.

The number of possible test agents runs into millions. Methods for developing small molecule, polymeric and genome based libraries are described, for example, in Ding, et al. J. Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. Compound libraries are well known and readily available in the art. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

In the methods of the invention, the test agents are typically provided free in solution, however the agent may be in complex with solid forms.

In some embodiments, the test agent increases activation of the IL-9 receptor by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control, e.g. as measured by increase in expression of TH2AF1 or ICACC, at either the mRNA or protein level.

In some embodiments, the test agent inhibits RORγ by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control, e.g. as measured with RORγ reporter constructs are commercially available, for example Cat Nos. K1883 and K1882 from Invitrogen (Grand Island, N.Y.).

Methods of Treatment

Provided herein are methods for treating or preventing cancer in a subject. The methods comprise administering to a subject in need thereof a therapeutically effective amount of an agent that is an agonist of the interleukin-9 receptor (IL-9R).

As used herein, "treatment", "treating", "prevention" or "amelioration" of cancer refers to inhibition of growth of a tumor, inhibiting metastasis of cancer, delaying or preventing the onset of cancer, or reversing, alleviating, ameliorating, inhibiting, slowing down, or stopping the progression of cancer. The term "treatment" or "treating", as used herein, does not encompass 100% cure of cancer. However, in one embodiment, the therapeutic methods described herein may result in 100% reversal of disease.

As used herein, the term "subject" or "patient" or refers to any mammal. The patient is preferably a human, but can also be a mammal in need of veterinary treatment.

The methods described herein are useful for the treatment of any type of cancer in a subject. As used herein, the term "cancer" includes any type of cancer. A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. In some circumstances, cancer cells will be in the form of a tumor; such cells may exist locally within an subject, or circulate in the blood stream as independent cells, for example, leukemic cells. In one embodiment, the cancer may be tumorogenic cancer, i.e. a cancer associated with a tumor, or a skin lesion such as in melanoma.

Examples of cancer include, but are not limited to, breast cancer, melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

In certain embodiments, prior to treatment, the patients are selected for having a particular cancer, or for being at risk of a particular cancer. The presence of cancer can be determined by means well known to clinicians. Initial assessment of cancer is based on symptoms presented by the patient. In addition, there are follow-up diagnostic procedures, including, but not limited to PET scans, CAT scans, biopsies, and bio-marker assessments.

Symptoms of cancer will vary dependent upon the type of cancer that is present. However, symptomatic signs of cancer, may include fatigue, weight loss or gain, or pale skin color.

In one embodiment of the methods described herein, at least one symptom of cancer is alleviated by at least 5%, at least 10%, at least 20%, at least 30%, at least 40%, at least 50%, at least 60%, at least 70%, at least 80%, or at least 90%. In such an embodiment, the clinical signs and/or the symptoms associated with the cancer are lessened as a result of the administration of the agonist/s. The signs or symptoms to be monitored are characteristic of a particular cancer and are known to the skilled clinician, as well as the methods for monitoring the signs and conditions.

In one embodiment of the methods described herein, the cancer is a tumor and the size is reduced by at least 5%, at least 10%, at least 20%, at least 30%, at least 40%, at least 50%, at least 60%, at least 70%, at least 80%, or at least 90%.

In one embodiment of the methods described herein, the cancer is a lesion (e.g. melanoma lesion or lung cancer lesion) and the size is reduced by at least 5%, at least 10%, at least 20%, at least 30%, at least 40%, at least 50%, at least 60%, at least 70%, at least 80%, or at least 90%.

In one embodiment of the methods describe herein, cancer cell proliferation, or cancer growth, is inhibited by at least 5%, at least 10%, at least 20%, at least 30%, at least 40%, at least 50%, at least 60%, at least 70%, at least 80%, or at least 90%. The skilled clinician may monitor the size or rate of growth of a tumor using a diagnostic imaging method typically used for the particular tumor (e.g., using ultrasound or magnetic resonance image (MRI) to monitor a tumor).

In some embodiments, the methods described herein may be used to treat melanoma. The term "melanoma" as used herein includes all types of melanoma, including, for example, melanoma skin cancer, ocular melanoma, and mucosal melanoma. Melanoma is caused by changes melanocytes that produce melanin. There are four major types of melanoma: 1) superficial spreading melanoma, which is usually flat and irregular in shape and color, with different shades of black and brown and is most common in Caucasians, 2) nodular melanoma, which usually starts as a raised area that is dark blackish-blue or bluish-red, but can be colorless, 3) Lentigo maligna melanoma, which usually occurs in the elderly and is most common in sun-damaged skin on the face, neck, and arms. The abnormal skin areas are usually large, flat, and tan with areas of brown, 4) Acral lentiginous melanoma, which is the least common form and usually occurs on the palms, soles, or under the nails and is more common in African Americans. Melanomas may also appear in the mouth, iris of the eye, or retina at the back of the eye and can be found during dental or eye examinations. Although very rare, melanoma can also develop in the vagina, esophagus, anus, urinary tract, and small intestine.

The presence of melanoma can be determined by means well known to those of skill in the art, e.g. tissue biopsies and in situ assays in which malignant melanoma (malignant melanocytes scattered in all epidermal layers) show atrophic epidermis, prominent dermal solar elastosis and almost always lymphocytic infiltration. Invasion of the dermis by melanocytes may occur in lentigo maligna melanoma. In addition, melanoma may be detected by methods that include, but are not limited, immunohistochemistry using the melanoma specific antibody HMB-45, or RT-PCR with different melanoma associated antigens (MAA) including, but not limited to tyrosinase, MART-1/Melan A, Pmel-17, TRP-1, and TRP-2 (see, e.g., Hatta N., et al., *J Clin Pathol.* 1998 August; 51(8):597-601). Biomarkers for melanoma are also known and can be used for example to assess subjects at risk of melanoma. Non-limiting example biomarkers for melanoma are described in PCT Publications WO 2008/141275, WO 2009/073513, or in U.S. Pat. No. 7,442,507, which are herein incorporated by reference in their entirety.

Symptoms of melanoma include, but are not limited to, a mole, sore, lump, or growth on the skin that may bleed, or exhibit change in skin coloring. Often patients are told of an ABCDE system the can help them remember possible symptoms of melanoma to watch out for: Asymmetry: a mole where one half of the abnormal area is different from the other half; Borders, the edges of the growth are irregular; Color, the color changes from one area to another, with shades of tan, brown, or black, and sometimes white, red, or blue, e.g. a mixture of colors may appear within one sore; Diameter, the spot is usually (but not always) larger than 6 mm in diameter, about the size of a pencil eraser; and Evolution, the mole keeps changing appearance.

In one embodiment of the methods described herein, at least one symptom of melanoma is alleviated by at least 5%, at least 10%, at least 20%, at least 30%, at least 40%, at least 50%, at least 60%, at least 70%, at least 80%, or at least 90%. In such an embodiment, the clinical signs and/or the symptoms associated with the melanoma are lessened as a result of the administration of the inhibitor/s. The signs or symptoms to be monitored are characteristic of a particular melanoma and are known to the skilled clinician, as well as the methods for monitoring the signs and conditions.

In another embodiment, the practice of the method in conjunction with other therapies is contemplated such as conventional chemotherapy, radiation therapy or surgery directed against solid tumors and for control of establishment of metastases. The administration of angiogenesis-inhibiting amounts of combination therapy may be conducted before, during or after chemotherapy, radiation therapy or surgery.

Pharmaceutical Compositions and Administration

Embodiments of the method described herein comprises administering to a subject an agonist of the IL-6 receptor for the treatment of cancer (e.g. melanoma and other cancers). The administration of the agonist may be for either "prophylactic" or "therapeutic" purpose. When provided prophylactically, therapy is provided in advance of any symptom. The prophylactic administration of the therapy serves to prevent formation of cancer. Prophylactic administration may be given to a patient with, for example, a family history of cancer, or a patient that has had a cancer removed surgically. Alternatively, administration of the combination therapy may be given to a patient with rising cancer marker protein levels. Multiple biomarkers for particular cancers are known in the art, for example cancer biomarkers are reviewed in Henry N L, Hayes D F (2012) Cancer biomarkers. *Mol. Oncol.* available online February 6, in press. Example melanoma markers described in PCT Publications WO 2008/141275, WO 2009/073513, or in U.S. Pat. No. 7,442,507.

When provided therapeutically, the administration of the composition comprising the agonist agent may be provided at (or after) the onset of a symptom of cancer, or upon indication of tumor.

For any combination therapy used herein, e.g. multiple agonist such as IL-4 and TGFβ, the agonists can be present in the same or different pharmaceutical composition. When administrated at different times, the can be administered within 5 minutes, 10 minutes, 20 minutes, 60 minutes, 2 hours, 3 hours, 4, hours, 8 hours, 12 hours, 24 hours of administration of the other. When the agonist are administered in different pharmaceutical compositions, routes of administration can be different.

The effective dosage range for the administration of the agonists depends upon the form of the agonist and its potency. It is an amount large enough to produce the desired effect in which symptoms of cancer are ameliorated (e.g. inhibition of tumor growth). The phrase "therapeutically-effective amount" as used herein means that amount of agonist agent or composition comprising the agonist/s which is effective for producing the desired therapeutic effect, in at least a sub-population of cells, in a subject at a reasonable benefit/risk ratio applicable to any medical treatment. For example, an amount of an agent administered to a subject that is sufficient to produce a statistically significant, measurable change in at least one symptom of cancer. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. There are preclinical melanoma models that are well known to those of skill in the art which can be used to determine therapeutically effective amounts of the agents and to optimize administration regimes. See for example Yang et al. (2010) RG7204 (PLX4032), A selective BRAFV600E inhibitor, displays potent antitumor activity in preclinical melanoma models, *Cancer Research,* 70:5518-5527, which is herein incorporated by reference its entirety.

In one embodiment, a therapeutically effective amount of agonist, inhibits tumor volume in a preclinical model by at least 5%, at least 10%, at least 20%, at least 30%, at least 40%, at least 50%, at least 60%, at least 70%, at least 80%, at least 90% and reduces at least one symptom of melanoma by at least 5%, at least 10%, at least 20%, at least 30%, at least 40%, at least 50%, at least 60%, at least 70%, at least 80%, or at least 90%. For example, tumor volumes in xenograft mice can be calculated using the following ellipsoid formula: $[D \times (d2)]/2$, in which D represents the large diameter of the tumor, and d represents the small diameter. Tumor volumes of treated groups are presented as percentages of tumor volumes of the control groups (% T/C) using the following formula: $100 \times [(T-T_0)/(C-C_0)]$, in which T represents mean tumor volume of a treated group on a specific day during the experiment, $T_0$ represents mean tumor volume of the same treated group on the first day of treatment, C represents mean tumor volume of a control group on the specific day during the experiment, and $C_0$ represents mean tumor volume of the same treated group on the first day of treatment. Percent tumor growth inhibition can be calculated as 100–% T/C, with >100% tumor growth inhibition representing regression. Survival can be calculated using a predefined cutoff volume of 2,000 mm$^3$ as a surrogate for mortality (See e.g. Yang et al. (2010), Supra).

In one embodiment a therapeutically effective amount of agonist of the IL-9R increases the activity of the IL-9R by at least 5%, at least 10%, at least 20%, at least 30%, at least 40%, at least 50%, at least 60%, at least 70%, at least 80%, or at least 90% and reduces at least one symptom of cancer by at least 5%, at least 10%, at least 20%, at least 30%, at least 40%, at least 50%, at least 60%, at least 70%, at least 80%, or at least 90%.

In one embodiment a therapeutically effective amount of the agonist of the IL9-R inhibits cellular proliferation in a preclinical model by at least 5%, at least 10%, at least 20%, at least 30%, at least 40%, at least 50%, at least 60%, at least 70%, at least 80%, or at least 90% and reduces at least one symptom of cancer by at least 5%, at least 10%, at least 20%, at least 30%, at least 40%, at least 50%, at least 60%, at least 70%, at least 80%, or at least 90%. Inhibition of cellular proliferation may be evaluated by 3-(4,5-dimethylthiazole-2-yl)-2,5-diphenyl-2H-tetrazolium bromide (MTT; Sigma) assay. For example cells can be plated in 96-well microtiter plates at a density of 1,000 to 5,000 cells per well in a volume of 180 pt. Twenty-four hours after cell plating, 20 μL of an appropriate agent dilution can be added to plates in duplicate. The plates may then be assayed for proliferation 6 days after the cells were plated according to the procedure originally described by Mosmann, Rapid colomeric assay for cellular growth and survival: application to proliferation and cytotoxicity assays. *J. Immunol. Methods* 1883:65:55-63). Percent inhibition can then be calculated and the IC50 determined from the regression of a plot of the logarithm of the concentration versus percent inhibition by XLfit (version 4.2; IDBS) using a Dose-Response One-Site Model (#205) (see e.g. Yang et al. Supra)

The therapeutically effective dose can be estimated initially from a suitable cell culture or transcription assays (e.g. cancer cell growth assays, or e.g. transcription assays for inhibition of RORgamma activity, or assays to monitor activation of the IL-9R), then a dose of each agent and treatment regime may be formulated in animal models to achieve a circulating plasma concentration range that includes the IC50 as determined in cell culture.

For administration to a subject, the agents can be provided in pharmaceutically acceptable compositions. These pharmaceutically acceptable compositions comprise a therapeutically-effective amount of one or more agonists of IL-9R, formulated together with one or more pharmaceutically acceptable carriers (additives) and/or diluents. The pharmaceutical compositions can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally (e.g. as a nasal spray or suppository); or (9) nasally. Additionally, agents can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Guidance for formulations can be found in e.g. Remington: The Science and Practice of Pharmacy by Alfonso R. Gelmaro (Ed.) 20$^{th}$ edition: Dec. 15, 2000, Lippincott, Williams $ Wilkins, ISBN: 0683306472, and are briefly described below.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The amount of agent which can be combined with a carrier material to produce a single dosage form will generally be that amount of the agent which produces a therapeutic effect. Generally out of one hundred percent, this amount will range from about 0.1% to 99% of agent, preferably from about 5% to about 70%, most preferably from 10% to about 30%.

Formulations suitable for parenteral administration conveniently include sterile aqueous preparation of the active agent which is preferably isotonic with the blood of the recipient. Thus, such formulations may conveniently contain distilled water, 5% dextrose in distilled water or saline. Useful formulations also include concentrated solutions or solids containing the agent which upon dilution with an appropriate solvent give a solution suitable for parental administration above.

For enteral administration, an agent can be incorporated into an inert carrier in discrete units such as capsules, cachets, tablets or lozenges, each containing a predetermined amount of the active agent; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active agent in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active agent with any suitable carrier.

A syrup or suspension may be made by adding the active agent to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N,N-bis(3-D-gluconamidopropyl)-cholamide), chlorobutanol, octoxynol-9, benzyl alcohol, phenols, cresols, and alkyl alcohols. In one embodiment, the oral absorption enhancer may be sodium lauryl sulfate.

As used herein, the term "administer" or "administering" refers to the placement of a composition into a subject by a method or route which results in at least partial localization of the composition at a desired site such that desired effect is produced. A agent or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, cells that express IL-9 are administered to a subject by adoptive cell transfer. Methods for administering cells are well known to those of skill in the art e.g. as provided in WO 2004/048557; WO 2008/033403; U.S. 2008/0279813 WO2008/033403; U.S. Pat. No. 7,572, 631; and WO 2009/131712, which are herein incorporated by reference in their entirety. The amount of IL-9 producing cells (e.g. Th9 cells or $T^{reg}$. cells, among others) which will be effective in the treatment and/or suppression of cancer may be determined by standard clinical techniques. The dosage will depend on the type of cancer to be treated, the severity and course of the cancer, previous therapy the recipient has undertaken, the recipient's clinical history, and the discretion of the attending physician. The IL-9 producing cell population may be administered in various treatment regimes, e.g., a single or a few doses over one to several days to ameliorate symptoms or periodic doses over an extended time to inhibit cancer progression or to prevent cancer recurrence. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Exemplary, non-limiting doses that could be used in the treatment of human subjects range from at least $3.8\times10^4$, at least $3.8\times10^5$, at least $3.8\times10^6$, at least $3.8\times10^7$, at least $3.8\times10^8$, at least $3.8\times10^9$, or at least $3.8\times10^{10}$ IL-9 producing cells/m2. In certain embodiments, the dose used in the treatment of human subjects ranges from about $3.8\times10^9$ to about $3.8\times10^{10}$ IL-9 producing cells/m2. Cells may be administered systemically, or locally at the site of the cancer.

In some embodiments, the agonists of the IL-9R are nucleic acids, e.g. e.g. including, but not limited to, DNA, antisense, ribozyme or RNAi (e.g. siRNA, shRNA). Methods of delivering RNAi interfering (RNAi) agents, other nucleic acid agents (e.g. nucleic acids that encode IL-9, or other agonist nucleic acids or peptides), or vectors containing agonist nucleic acids, to the target cells (e.g., cancer or tumor cells) can include, for example directly contacting the cell with a composition comprising a modulatory nucleic acid, or local or systemic injection of a composition containing the agonist nucleic acid. In one embodiment, nucleic acid agents (e.g. RNAi, siRNA, or other nucleic acid, expression vectors that encode agonists (including viral vectors) are injected directly into a tumor or lymph system. In some embodiments agonist nucleic may be delivered by systemic administration, wherein the nucleic acid is complexed with, or alternatively contained within a carrier. Example carriers for modulatory nucleic acid agents include, but are not limited to, peptide carriers, viral vectors, gene therapy reagents, and/or liposome carrier complexes and the like.

Alternatively, the agent may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979) also U.S. Pat. Nos. 4,906,474, 4,925,673 and 3,625,214, and Jein, TIPS 19:155-157 (1998), the contents of which are hereby incorporated by reference.

In some embodiments, the agents described herein for treatment of cancer may be administered to a subject in combination with additional pharmaceutically active agents. Exemplary pharmaceutically active compounds/agents include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such agents lies within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. . . . It is to be further understood that the ranges intermediate to the given above are also within the scope for use in methods and pharmaceutical compositions described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity.

The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The pharmaceutical compositions can be administered during infancy (between 0 to about 1 year of life), childhood (the period of life between infancy and puberty) and during puberty (between about 8 years of life to 18 years of life). The pharmaceutical compositions can also be administered to treat adults (greater than about 18 years of life). A dose administered at least once, may be provided as a bolus, a continuous administration or sustained release. Multiple administration over a period of weeks or months may be preferable. It may also be preferable to administer the dose at least once/week and even more frequent administrations (e.g. daily). Subsequent doses may be administered as indicated.

In one embodiment, the agonist may be administered to a subject using an administration regime that results in a steady state concentration of 70 µg/mL, or 60 µg/mL, or 50 µg/mL, 40 µg/mL, 30 mcg/ml, or 20 µg/mL (Rozman, B. (2002) Clinical pharmacokinetics of leflunomide, *Clin. Pharmacokinetic*, 41:421-430). In one embodiment, the steady state concentration is 60 µg/mL or less, 50 µg/mL or less, 40 µg/mL or less, 30 µg/ml or less, or 20 µg/mL or less.

In one embodiment, the agonist may be administered at a high concentration (e.g. 100 to 1000 mg) daily for 3 days, followed by lower daily doses of 20 to 100 mg/ml. for a steady state concentration. In one embodiment, agonist may be administered at a dosage of 960 mg twice a day, at a dosage less than 900 mg twice a day, less than 850 mg twice a day, less than 800 mg twice a day, or less than 700 mg twice per day.

The efficacy of a given treatment regime for cancer can be determined by the skilled clinician, for example by assessing physical indicators of cancer, such as e.g., tumor size or lesion size, metastasis, tumor growth rate, etc. However, a treatment is considered "effective treatment," as the term is used herein, if any one or all of the signs or symptoms of the cancer are altered in a beneficial manner, e.g. improved or ameliorated by at least 10% following treatment with an agent that is an agonist of the IL-9R. Efficacy can also be measured by a failure of an individual to worsen as assessed by stabilization of tumor growth, hospitalization or need for medical interventions (i.e., progression of the melanoma is halted or at least slowed). Methods of measuring these indicators are known to those of skill in the art and/or described herein. Treatment includes in an individual includes: (1) inhibiting the disease, e.g., arresting, or slowing tumor or lesion growth; or (2) relieving the disease, e.g., causing regression of symptoms, reducing tumor or lesion size; and (3) preventing or reducing the likelihood of the development of cancer, or preventing metastasis of the cancer.

Also provided are methods for the prognosis of cancer (e.g. melanoma or other cancers) in a subject. The methods comprise determining the level of IL-9 producing T cells in a tumor, wherein the presence of reduced levels of IL-9 producing T-cells (e.g. Th9 cells) within the tumor as compared to the level of IL-9 producing T-cells (e.g. Th9 cells) in normal skin or normal blood is indicative of increased metastatic potential and a poor prognosis. The level of IL-9 producing T cells may be determined by means well known to those of skilled in the art, e.g. as described in Example 1 herein. In one specific embodiment, the cancer is melanoma, however any cancer may be prognosed using the methods described herein.

In certain embodiments, the reduced level of IL-9 producing T-cells indicates a treatment protocol for the that comprises administrating to the subject in need thereof an agonist of the IL-9 receptor, e.g. an agent that binds and activates the IL-9 receptor such as IL-9 or other agonist; or an agent that increases IL-9 expression in the subject (e.g. administration of IL-9 producing T cells, such as tumor specific TH9 cells that express IL-9, or administration of an inhibitor of RORγ).

Methods for directing treatment in a subject are also provided. In one embodiment, the method comprises determining the level of RORγ expression in T cells present within a tumor, wherein an an increased expression of RORγ in T cells of the tumor as compared to T cells in normal human blood or skin, indicates that the cancer may be treated with an inhibitor of RORγ. The level of RORγ may be determined by means well known to those of skilled in the art, e.g. as described herein and as described in Example 1; kits are available for RORγ detection.

DEFINITIONS

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The abbreviation, "e.g." is derived from the Latin exempli gratia, and is used herein to indicate a non-limiting example. Thus, the abbreviation "e.g." is synonymous with the term "for example."

The terms "polypeptide," "peptide" and "protein" refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acids.

As used herein, "variant polypeptides" may comprise conservatively substituted sequences, meaning that one or more amino acid residues (such as a native IL-9 polypeptide, or other polypeptide, or cytokine etc.) is replaced by different residues, and that the conservatively substituted polypeptide retains a desired biological activity, that is essentially equivalent to that of the native polypeptide. Examples of conservative substitutions include substitution of amino acids that do not alter the secondary and/or tertiary structure of the polypeptide. Other examples involve substitution of amino acids that have not been evolutionarily conserved. One or more polypeptide sequences from non-human species can be aligned with, for example, human using methods well known to one of ordinary skill in the art to determine which residues are conserved and which tolerate more variability. Advantageously, in some embodiments, these conserved amino acids are not altered when generating conservatively substituted sequences.

Any given amino acid may be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. For example, IL-9 polypeptides comprising conservative amino acid substitutions can be tested in any one of the assays described herein to confirm that a desired apoptotic activity of a native IL-9 is retained.

Amino acids may be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (O); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Conservative substitutions may include, for example: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any cysteine residue not involved in maintaining the proper conformation of the polypeptide also can be substituted, generally with serine, to improve the oxidative stability of the molecule and prevent aberrant crosslinking Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%. In one embodiment, there is a 100% decrease (e.g. absent level as compared to a reference sample).

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the term "IC50" refers to the concentration of an agent that produces 50% of the maximal inhibition of activity or expression measurable using the same assay in the absence of the inhibitor. The IC50 can be as measured in vitro or in vivo. The IC50 can be determined by measuring activity using a conventional in vitro assay (e.g. protein activity assay, or gene expression assay e.g. RORγ activity, or inhibition of proliferation, migration, or tumor/lesion size).

As used herein, the term "co-stimulatory molecule-activating agents" refers to any compound well-known to one of skill in the art that immunospecifically binds to or associates with a co-stimulatory molecule expressed by an immune cell (preferably, an activated immune cell) and induces the activation of a signal transduction pathway associated with the co-stimulatory molecule. For example, a compound that immunospecifically binds to or associates with a co-stimulatory molecule selectively expressed by an activated immune cell (e.g., an activated T-cell) and induces the activation of a signal transduction pathway associated with the co-stimulatory molecule. Co-stimulatory molecule-activating agents include, but are not limited to, proteinaneous agents (e.g., cytokines, peptide mimetics, and antibodies), small molecules, organic compounds, inorganic compounds, and nucleic acid molecules comprising nucleotide sequences encoding proteins, polypeptides, or peptides (e.g., cytokines, peptide mimetics, and antibodies) that immunospecifically bind to or associate with a co-stimulatory molecule expressed by an activated immune cell and induce the activation of a signal transduction pathway associated with the co-stimulatory molecule. For example, ligands that immunospecifcally bind to a co-stimulatory molecule selectively expressed by activated T-Cells increase the expression and/or release of cytokines by immune cells in an in vitro or in vivo assay. "Co-stimulatory molecules" include, for example: 1) B7/CD28 family molecules such as B7-1/CD80 CD28, B7-2/CD86 CTLA-4, B7-H1/PD-L1 Gi24/Dies1/VISTA, B7-H2 ICOS, B7-H3 PD-1, B7-H4 PD-L2/B7-DC, B7-H6 PDCD6 and BTLA; TNF superfamily molecules, 4-1BB/TNFRSF9/CD137 CD40 Ligand/TNFSF5, 4-1BB Ligand/TNFSF9 GITR/TNFRSF18, BAFF/BLyS/TNFSF13B GITR Ligand/TNFSF18, BAFF R/TNFRSF13C HVEM/TNFRSF14, CD27/TNFRSF7 LIGHT/TNFSF14, CD27 Ligand/TNFSF7 OX40/TNFRSF4, CD30/TNFRSF8 OX40 Ligand/TNFSF4, CD30 Ligand/TNFSF8 TACI/TNFRSF13B, CD40/TNFRSF5; SLAM family 2B4/CD244/SLAMF4 CD84/SLAMF5, BLAME/SLAMF8 CD229/SLAMF3, CD2 CRACC/SLAMF7, CD2F-10/SLAMF9 NTB-A/SLAMF6, CD48/SLAMF2 SLAM/CD150, CD58/LFA-3; and other co-stimulatory molecules CD2 Ikaros, CD53 Integrin alpha 4/CD49d, CD82/Kai-1 Integrin alpha 4 beta 1, CD90/Thy1 Integrin alpha 4 beta 7/LPAM-1, CD96 LAG-3, CD160 LMIR1/CD300A, CRTAM TCL1A, DAP12 TCL1B, Dectin-1/CLEC7A TIM-1/KIM-1/HAVCR, DPPIV/CD26 TIM-4, EphB6 TSLP, HLA Class I TSLP R, HLA-DR.

It should be understood that the methods and compositions described herewith are not limited to the particular methodology, protocols, and reagents, etc., described herein and as such may vary. The terminology used herein is for the purpose of describing particular embodiments only, and is not intended to limit the scope of the present invention, which is defined by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains.

Certain embodiments of the invention may be as defined in any one of the following numbered paragraphs, i.e. paragraphs 1-32.

Paragraph 1. A method for treating cancer in a subject comprising administering to a subject in need thereof a therapeutically effective amount of an agonist of an interleukin-9 receptor (IL-9R).

Paragraph 2. The method of paragraph 1, wherein the agonist of the IL-9 receptor (IL-9) is selected from the group consisting of: a small molecule, a nucleic acid RNA, a nucleic acid DNA, a protein, a peptide, a cell, and an antibody.

Paragraph 3. The method of any of paragraphs 1-2, wherein the agonist comprises an agent that binds the IL-9 receptor.

Paragraph 4. The method of paragraph 3, wherein the agent that binds the IL-9 receptor comprises the cytokine interleukin 9 (IL-9), or fragment thereof.

Paragraph 5. The method of paragraph 4, wherein the cytokine interleukin 9 (IL-9) comprises human recombinant interleukin-9 (rIL-9).

Paragraph 6. The method of any of paragraphs 1-3, wherein the agonist is a monoclonal antibody.

Paragraph 7. The method of any of paragraphs 1-2, wherein the agonist comprises an agent that increases expression of IL-9 in the subject as compared to IL-9 expression in the absence of the agonist.

Paragraph 8. The method of paragraph 7, wherein the agonist comprises a population of cells that express IL-9.

Paragraph 9. The method of paragraph 8, wherein the population of cells comprises Th9 cells.

Paragraph 10. The method of paragraph 7, wherein the agonist comprises an inhibitor of RORγ.

Paragraph 11. The method of paragraph 10, wherein the inhibitor of RORγ comprises siRNA.

Paragraph 12. The method of paragraph 10, wherein the inhibitor of RORγ is selected from the group consisting of: ursolic acid, digoxin, SR1001, and TO901317.

Paragraph 13. The method of any of paragraphs 1-12, wherein the agonist further comprises a pharmaceutically acceptable carrier.

Paragraph 14. The method of any of paragraphs 1-13, wherein the subject is human.

Paragraph 15. The method of any of the paragraphs of 1-14, wherein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer Paragraph 16. The method of any of paragraphs 1-15, wherein the agonist is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, adoptive cell transfer, and parenteral administration.

Paragraph 17. Use of an effective amount of an agonist of an interleukin-9 receptor (IL-9R) for the treatment of cancer.

Paragraph 18. The use of paragraph 17, wherein the agonist of the IL-9 receptor (IL-9) is selected from the group consisting of: a small molecule, a nucleic acid RNA, a nucleic acid DNA, a protein, a peptide, a cell, and an antibody.

Paragraph 19. The use of any of paragraphs 17-18, wherein the agonist comprises an agent that binds the IL-9 receptor.

Paragraph 20. The use of paragraph 19, wherein the agent that binds the IL-9 receptor comprises the cytokine interleukin 9 (IL-9), or fragment thereof.

Paragraph 21. The use of paragraph 20, wherein the cytokine interleukin 9 (IL-9) comprises human recombinant interleukin-9 (rIL-9).

Paragraph 22. The use of any of paragraphs 17-19, wherein the agonist is a monoclonal antibody.

Paragraph 23. The use of any of paragraphs 17-18, wherein the agonist comprises an agent that increases expression of IL-9 in the subject as compared to IL-9 expression in the absence of the agonist.

Paragraph 24. The use of paragraph 23, wherein the agonist comprises a population of cells that express IL-9.

Paragraph 25. The use of paragraph 24, wherein the population of cells comprises Th9 cells.

Paragraph 26. The use of paragraph 23, wherein the agonist comprises an inhibitor of RORγ.

Paragraph 27. The use of paragraph 26, wherein the inhibitor of RORγ comprises siRNA.

Paragraph 28. The use of paragraph 26, wherein the inhibitor of RORγ is selected from the group consisting of: ursolic acid, digoxin, SR1001, and TO901317.

Paragraph 29. The use of any of paragraphs 17-28, wherein the agonist further comprises a pharmaceutically acceptable carrier.

Paragraph 30. The use of any of paragraphs 17-29, wherein the subject is human.

Paragraph 31. The use of any of the paragraphs of 17-30, wherein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer Paragraph 32. The use of any of paragraphs 17-31, wherein the agonist is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, adoptive cell transfer, and parenteral administration.

Paragraph 33, the method or use of any of paragraphs 1-32, wherein the subject is not administered one or more co-stimulatory molecule activating agents.

Paragraph 34, a method for the prognosis of cancer (e.g. melanoma or other cancers) in a subject comprising assaying a tumor for the presence of IL-9 producing T cells, wherein the presence of reduced levels of IL-9 producing T-cells (e.g. Th9 cells) within the tumor as compared to the level of IL-9 producing T-cells (e.g. Th9 cells) in normal skin is indicative of increased metastatic potential and a poor prognosis.

Paragraph 35, the method of paragraph 34 wherein the reduced level of IL-9 producing T-cells indicates a treatment protocol for the subject comprising administrating to the subject in need thereof an agonist of the IL-9 receptor (e.g. IL-9), e.g. an agent that binds and activates the IL-9 receptor, or an agent that increases IL-9 expression in the subject (e.g. administration of IL-9 producing T cells, such as tumor specific TH9 cells that express IL-9, or administration of an inhibitor of RORγ).

Paragraph 36, a method for directing treatment in a subject comprising determining the level of RORγ expression in T cells present within a tumor, wherein an increased expression of RORγ in T cells of the tumor as compared to T cells in normal human blood or skin, indicates that the cancer may be treated with an inhibitor of RORγ.

All references described herein, in the Examples and throughout the Specification, are incorporated herein by reference in their entirety.

EXAMPLES

Robust Tumor Immunity to Melanoma Mediated by Interleukin 9

The Examples described herein describe a novel and previously unappreciated role for IL-9 in tumor immunity and indicate novel therapeutic strategies. Recent studies have indicated that immunologic targeting of melanoma is a promising strategy[1]; however, how best to achieve this goal is incompletely understood. There is general agreement that T cell mediated assault on melanoma is required for an optimal long term result. An important role for CD4+T cells in tumor immunity is emerging from several recent studies[2-5]. In combination with radiation therapy and CTLA-4 blockade, adoptive transfer of naïve tumor specific CD4+T cells has been shown to eradicate large established melanomas[4,5]. Moreover, anti-melanoma effects of CD4+ T cells have been demonstrated in a melanoma lung metastasis model[6].

The role of Th17 cells in tumor immunity is controversial, with apparently contradictory results having been published. IL-17A has been reported to favor development of several cancers by promoting angiogenesis and tumor cell survival[7-9]. In contrast, other investigators have found that IL-17A can inhibit development of hematopoietic cancers by promoting CD8+T cell activation[10-12]. Treatment of immunocompetent tumor-bearing mice with Th17 cells reduced tumor colonies in the lung, and this anti-tumor activity of Th17 cells was mediated through activation of CD8+T cells[13]. In another study[14], antigen specific Th17 cells mediated regression of subcutaneous tumors in a lymphopenic host, and the anti-tumor effect was IFNγ dependent. The apparently contradictory reported effects of IL-17A in tumor immunity may depend on different experimental models and approaches[13,7,9,12], such as the immune status of the host, endogenous or ectopic expression of IL-17, method of tumor induction, and the biological nature of the tumor.

Because of the controversy discussed above, another approach to studying Th17 cells in tumor immunity was pursued, using mice whose T cells were deficient in the transcription factor retinoid-related orphan receptor-gamma (RORγ-/- mice). RORγt, a protein isoform of RORγ, is a lineage specific transcription factor critical for the development of Th17 cells[15,16,17] whose deficiency abrogates the development of IL-17A secreting Th17 cells. Increased expression of RORγ is reported in several inflammatory diseases including multiple sclerosis/experimental autoimmune encephalitis (EAE)[15], while its absence is implicated in attenuation of Ovalbumin induced allergic airway inflammation[18]. The role of RORγ in tumor immunity has never been directly assessed. Using RORγ-/- mice and IL-23R-/- mice, we observed significant growth inhibition of B16F10 melanoma, with evidence for increased anti-melanoma immune responses (tumor lymphocyte infiltration and increased cytokine expression). In parallel, transcriptional profiling experiments revealed the expected severely impaired IL-23R and IL-17A expression in RORγ-/- CD4+T cells differentiated under Th17 polarizing conditions. Unexpected, however, was a dramatic increase in the expression of IL-9 in these CD4+T cells.

The possibility that IL-9 overexpression might be related to the increased melanoma immunity seen in RORγ-/- chimeric mice was therefore tested. Strikingly, depletion of IL-9 by neutralizing mAb in IL-23R-/- and RORγ-/- chimeric mice was associated with enhanced melanoma growth. Mice deficient in IL-9 signaling pathways (IL-9R-/- mice), and normal mice treated with blocking IL-9 antibody had similarly enhanced growth. Administration of Th9 cells strongly inhibited melanoma growth, and this could be blocked by antibodies to IL-9. Treatment with exogenous rIL-9 suppressed melanoma, as well as lung carcinoma growth, in normal hosts as well as in hosts deficient in T and B cells. However, IL-9 did not block tumor growth in mast cell deficient hosts. Finally, IL-9 producing T cells (Th9 cells) were found in healthy human skin and blood, which show a phenotype directly comparable to murine Th9 cells. IL-9 producing T cells are reduced or absent in lesions of human metastatic melanoma. In conclusion, described herein is the identification of previously unreported roles of IL-9 and Th9 cells in melanoma immunity. The initial observation that abrogation of pathways important for Th17 cell development appears to enhance melanoma immunity, may be mediated in large part through the generation of a robust IL-9 mediated anti-melanoma response.

Example 1

Figure 7:
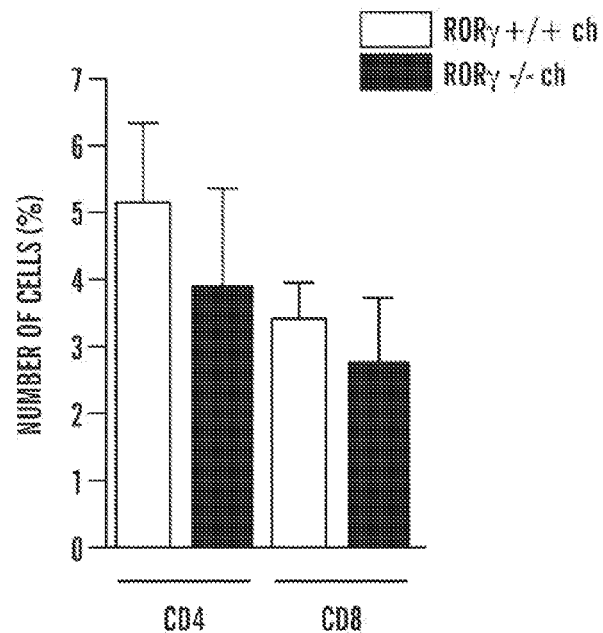
FIG. 7 demonstrates comparable numbers of CD4+ and CD8+T cells in the spleen of RORγ−/− ch and RORγ+/+ch mice. Rag1−/− mice were reconstituted with bone marrow of RORγ+/+ or RORγ−/− mice. After 8 weeks, numbers of CD4+ and CD8+T cells were analyzed by flow cytometry in the spleen of RORγ−/− chimeric mice (RORγ−/− ch) and RORγ+/+ch mice.

Deficiency of RORγ is Associated with Inhibited Melanoma Growth and Increased Tumor Lymphocytic Infiltration To examine the role of RORγ in tumor immunity, a B16F10 murine melanoma model was used. RORγ-/- mice do not develop secondary lymph nodes and have fewer CD4+ and CD8+T cells as compared to RORγ+/+ mice[19]. Therefore, RORγ-/- chimeric (RORγ-/-ch) and RORγ+/+ ch mice were generated by administering bone marrow cells from RORγ-/- or RORγ+/+ mice into sublethally irradiated Rag1-/- C57BL/6 mice[15,17]. After full reconstitution of T cells and restoration of the intact immune system (8-10 weeks), mice were used for tumor growth experiments (FIG. 7).

Figure 1B:
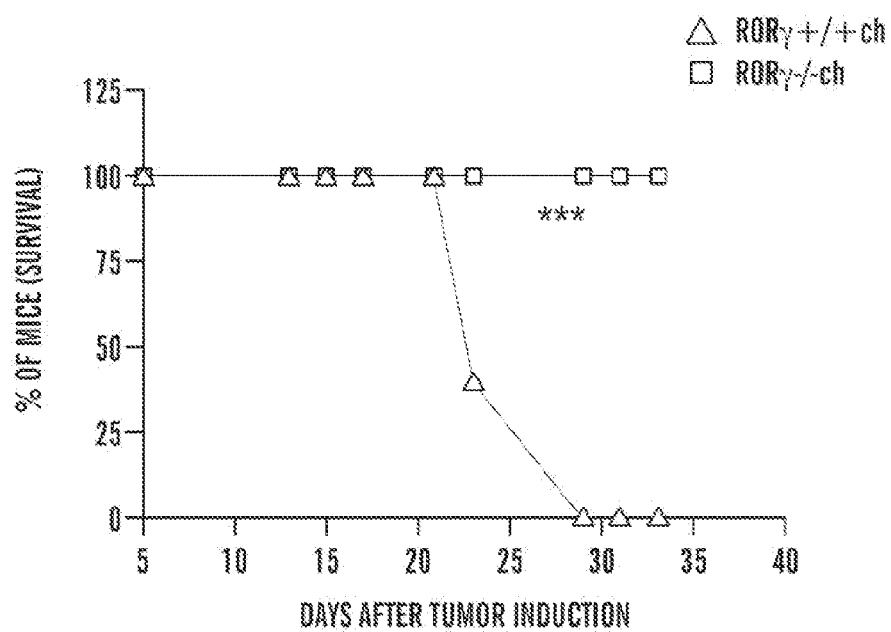
Figure 1C:
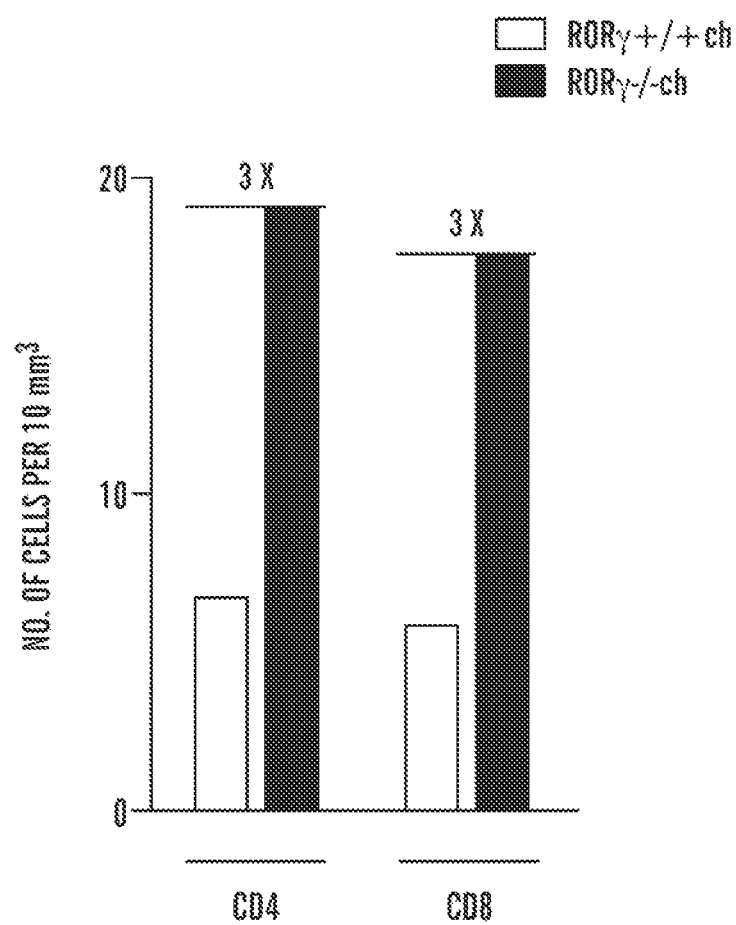
Figure 1D:
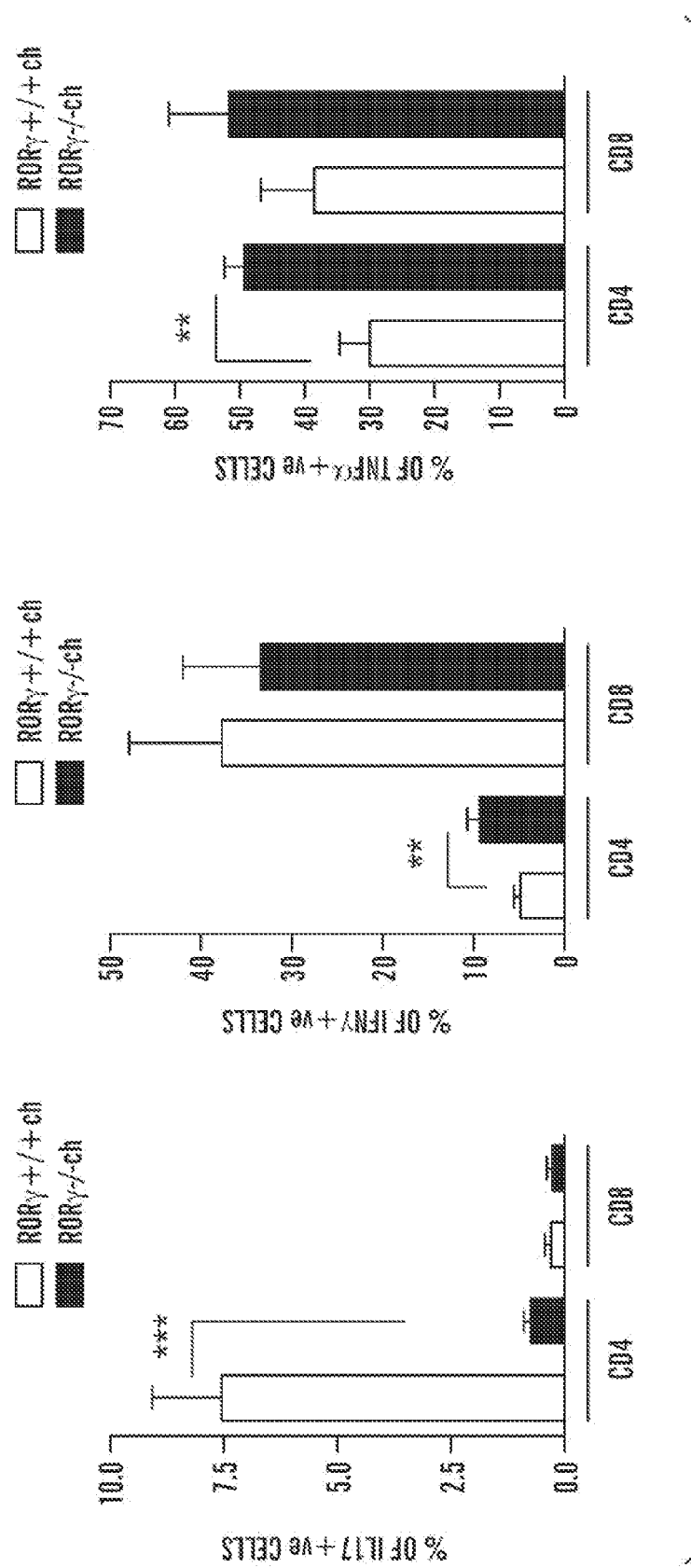

B16 melanoma cells were injected subcutaneously into RORγ+/+ ch and RORγ−/− ch mice, and tumor growth was monitored over time. RORγ−/− ch mice were resistant to melanoma growth, and survival of the RORγ−/− ch mice was significantly increased compared to control mice (FIGS. 1A-1B). The infiltration of lymphocytes in tumors removed from these mice was examined. Melanomas from RORγ−/− ch mice contained 3-fold higher numbers of CD4+T cells and CD8+T cells as compared to RORγ+/+ ch controls (FIG. 1C). T cells from draining lymph nodes of RORγ−/−ch melanoma bearing mice secreted negligible IL-17A, and increased amounts of IFNγ as well as TNFα (FIG. 1D). There was no difference in the number of melanoma-infiltrating CD4+CD25+FoxP3+T cells (T-regulatory cells) in RORγ+/+ch (7.2%±0.4) and RORγ−/−ch (5.9±0.7).

Example 2

Increased IL-9 Expression in RORγ Deficient T Cells

Figure 2:
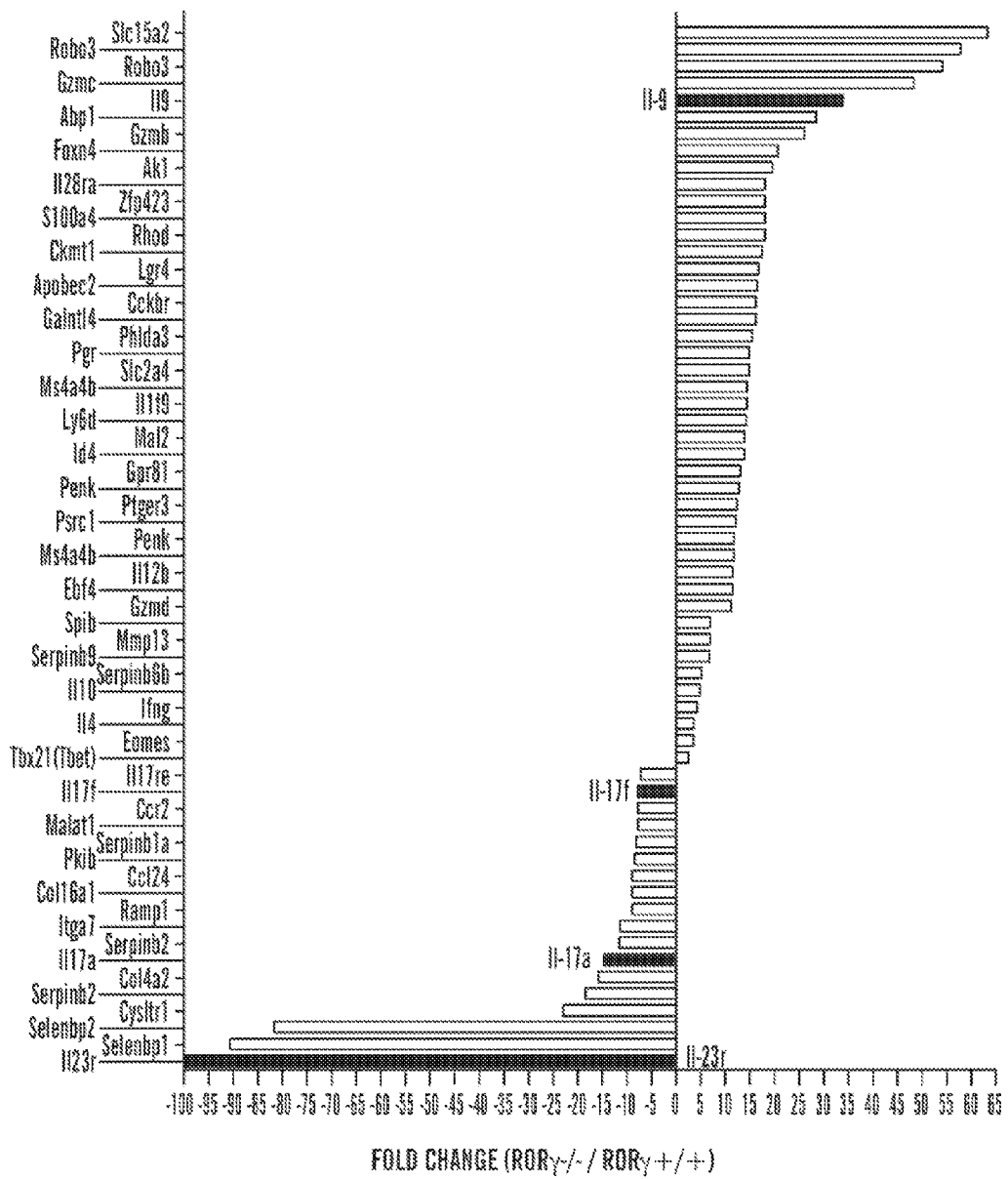
FIG. 2 demonstrates that sorted naive Th cells (CD4+ CD25-CD62Lhigh) from RORγ+/+ and RORγ−/− mice were differentiated under Th17 polarizing conditions. After 4 days, cells were harvested for transcriptional profiling experiments. Gene expression analysis was performed and expression of a set of genes is depicted as fold change (RORγ−/− vs. RORγ+/+). Two additional microarray analyses provided similar results.
Figure 8A:
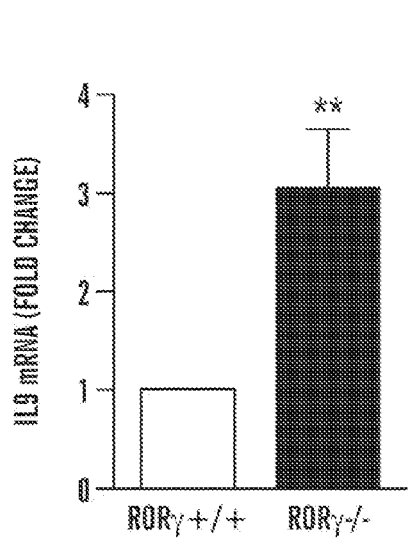
FIGS. 8A-8C depict the comprehensive cytokine profile of RORγ−/− T cells. Sorted CD4+CD25-CD62Lhigh+ cells from spleen of WT and RORγ−/− mice were polarized under Th17 or Th9 conditions. After 4 days of differentiation, cells were harvested for mRNA analysis (FIG. 8A) or intracellular staining of cytokines (FIG. 8B).
Figure 8B:
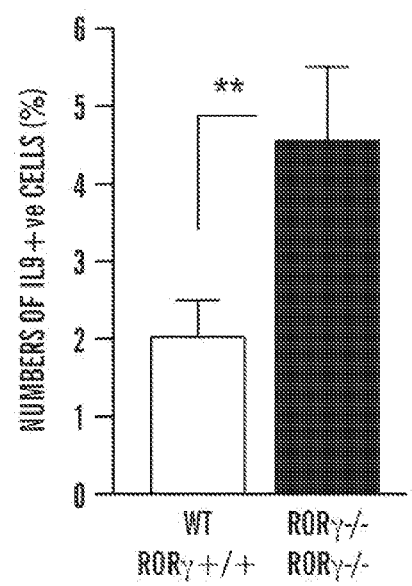
Figure 8C:
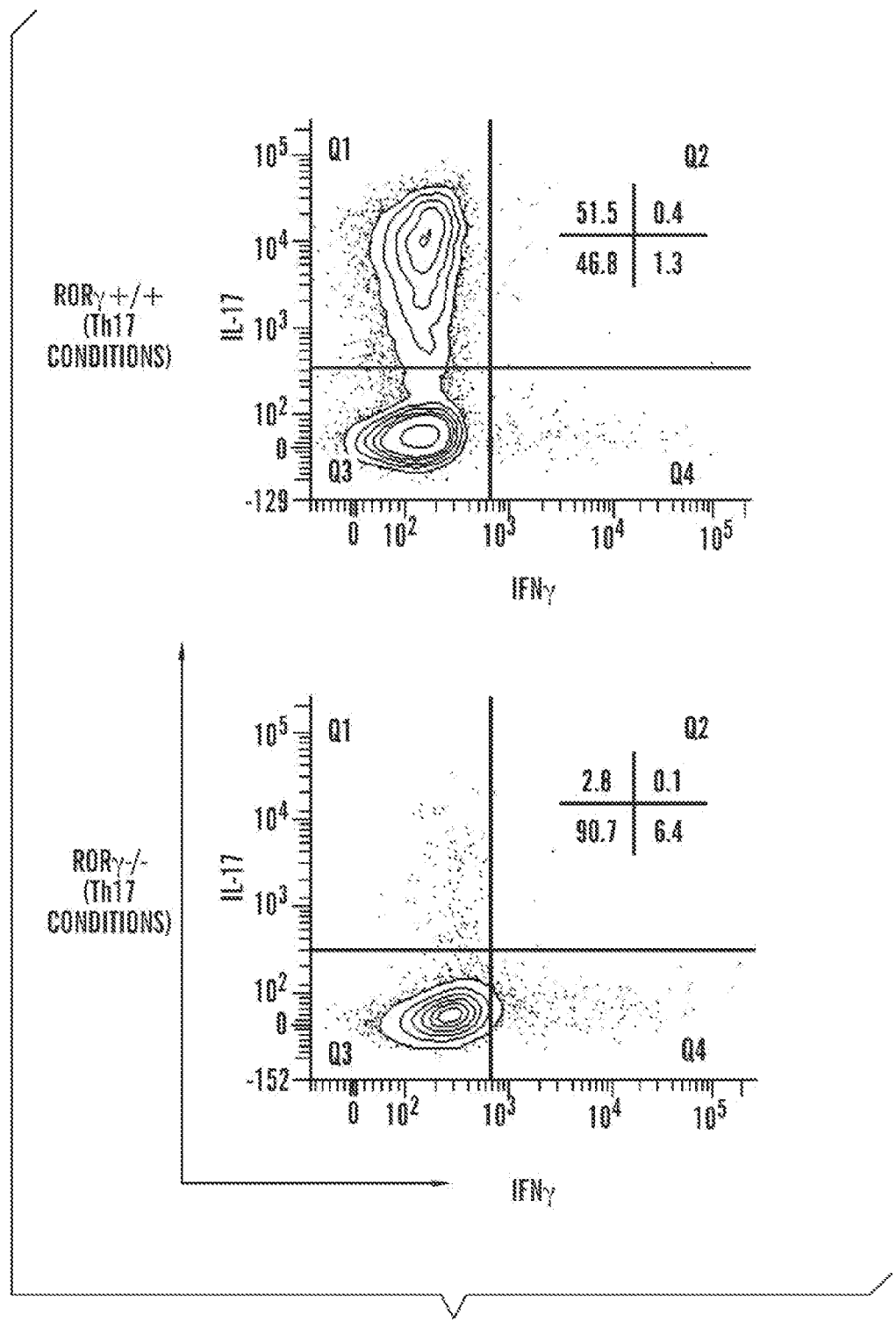

To further explore the mechanism of melanoma growth inhibition in RORγ−/− ch mice, transcriptional profiling analysis was performed using CD4+T cells from RORγ−/− and RORγ+/+ mice differentiated under Th17 polarizing conditions. As expected, expression of IL-17A, IL-17F and IL-23R in RORγ−/− CD4+T cells was much lower compared to RORγ+/+ CD4+T cells (FIG. 2). However, expression of IL-9 in RORγ−/− CD4+T cells was dramatically increased as compared to RORγ+/+CD4+T cells (FIGS. 2 and 8A-8C). Granzyme B and C expression were also significantly enhanced. Increased IL-9 mRNA expression and increased frequency of IL-9 secreting cells by RORγ−/− CD4+T cells was observed (FIGS. 8A-8C). Because of the striking upregulation of IL-9 under these conditions, subsequent experiments were focused on the potential role of IL-9 in tumor immunity.

Figure 9D:
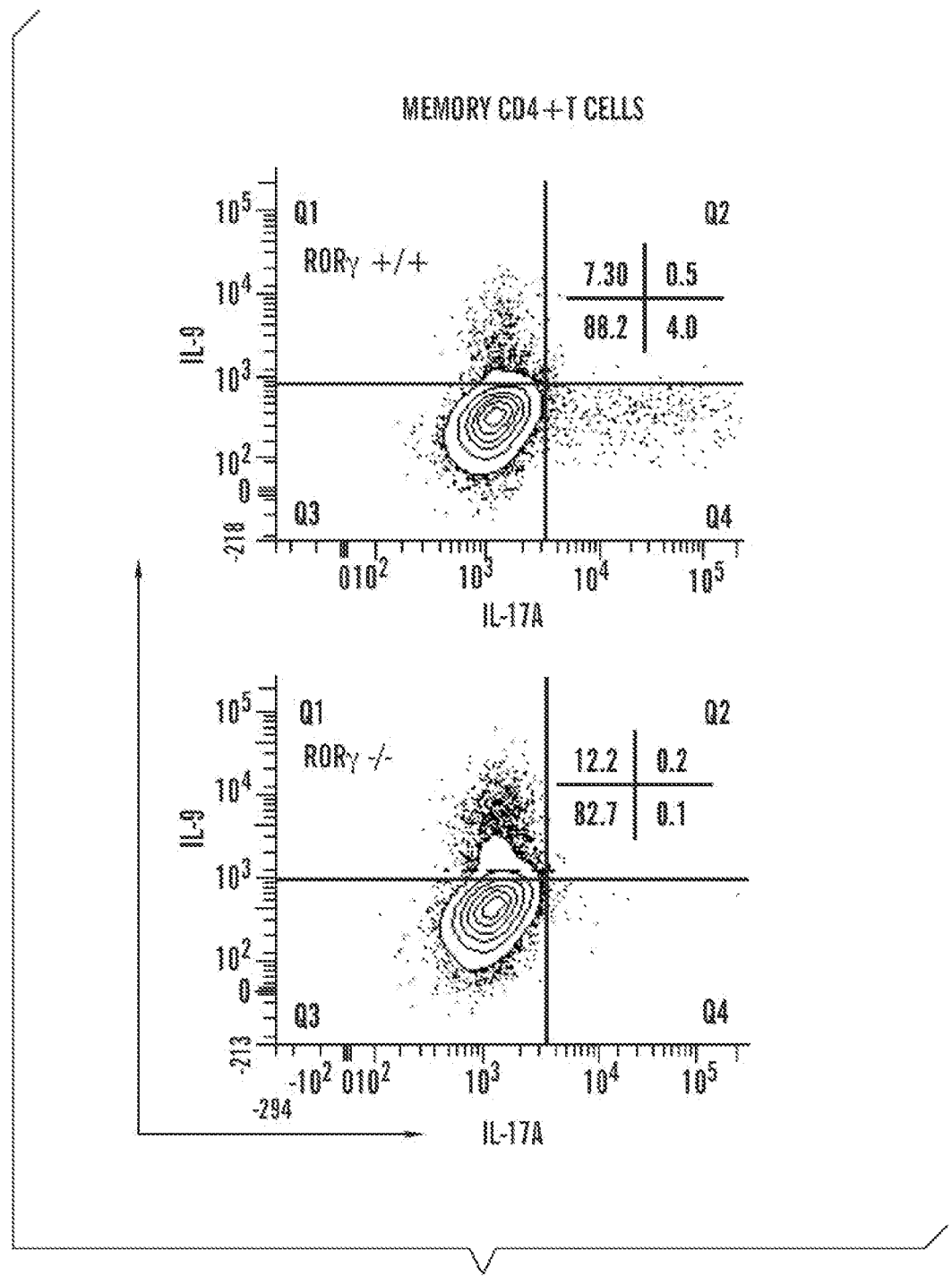
Figure 9E:
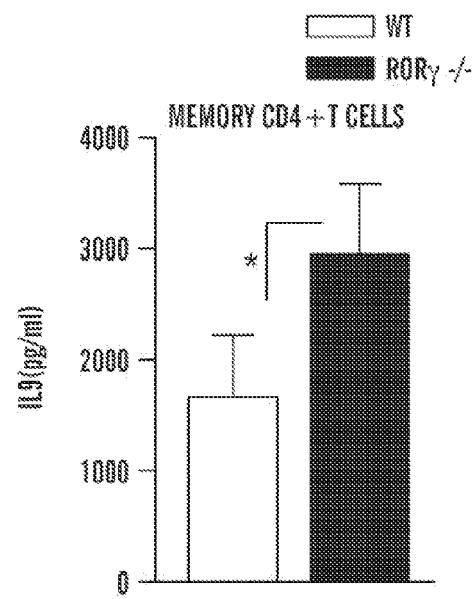
Figure 9F:
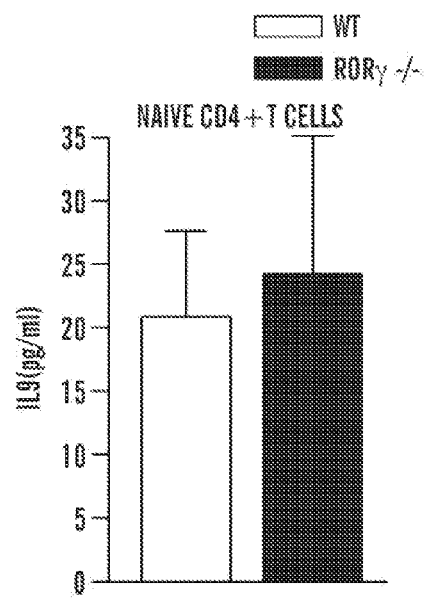
Figure 9G:
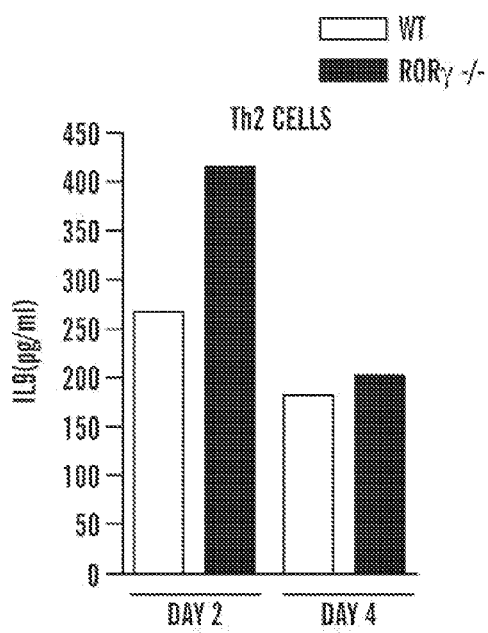
Figure 9H:
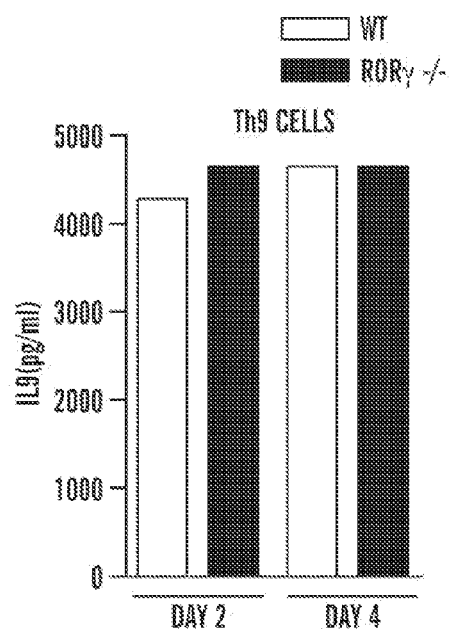

To be certain that the T cells from RORγ−/− ch mice did not have an intrinsic property that predisposed them to IL-9 production; naive and memory CD4+T cells from these mice were examined. CD4+T cells, CD4+CD25-CD62L low (memory T cells) and CD4+CD25-CD62L high (naïve CD4+T cells) from RORγ+/+ and RORγ−/− mice were culture sorted and stimulated with plate bound anti-CD3/CD28 mAbs. There was increased expression of IL-9 in RORγ−/− CD4+T cells (FIGS. 9A-9B) and memory CD4+T cells (FIGS. 9C-9E). However, negligible IL-9 expression was observed in naïve CD4+T cells, and importantly there was no difference in IL-9 expression between RORγ+/+ and RORγ−/− naïve CD4+T cells (FIG. 9F). Th2 and Th9 cells also secrete IL-9[20,21]; there was increased IL-9 expression in RORγ−/− Th2 cells; however, RORγ−/− CD4+ T cells under Th9 condition showed increased IL-9 production compared to RORγ+/+Th9 cells (FIGS. 9G-9H).

Figure 3A:
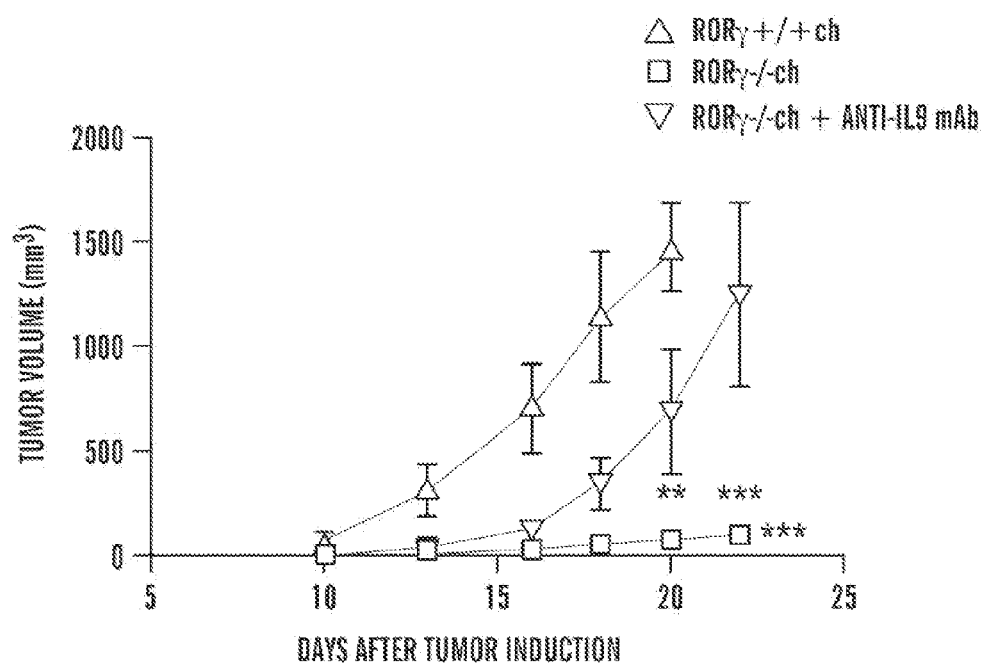
FIGS. 3A-3D depict the effect on melanoma immunity when IL-9 is inhibited.
Figure 3B:
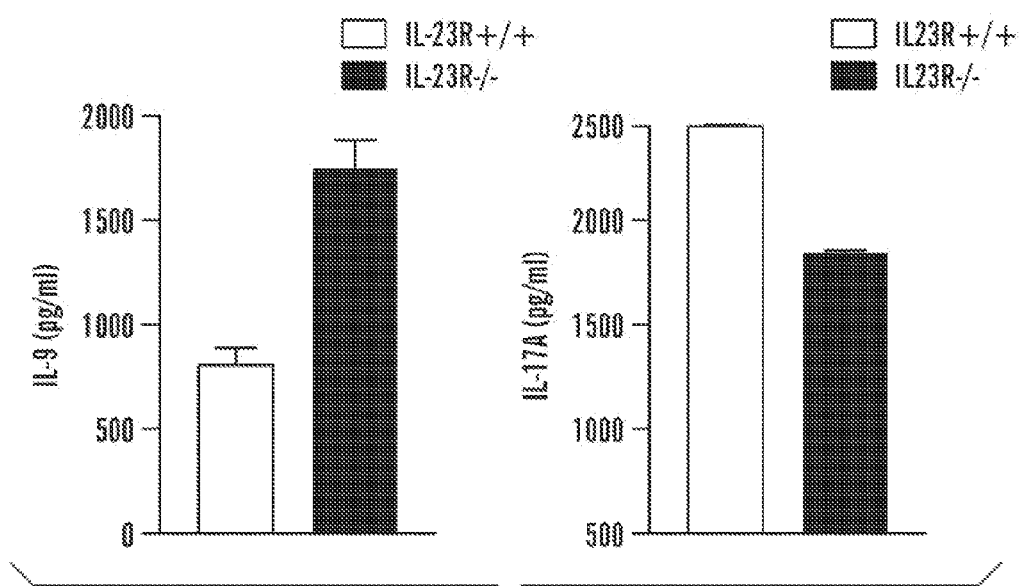
Figure 3C:
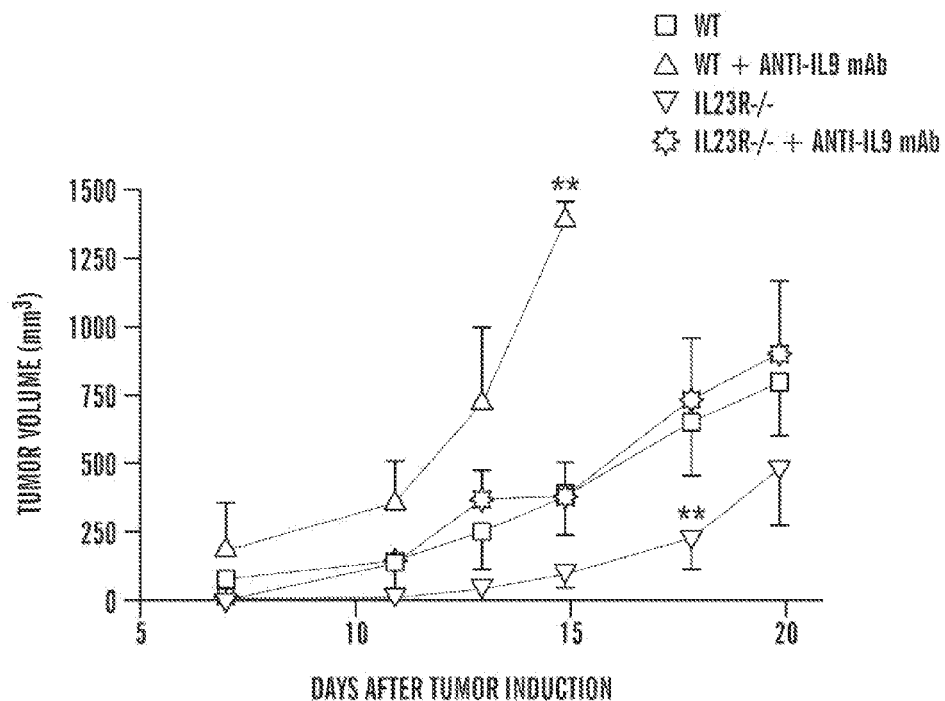

To explore if the enhanced anti-melanoma response in RORγ−/− ch mice could be attributed to IL-9, melanoma cells were injected subcutaneously into RORγ−/− ch mice. Tumor growth in these mice lagged significantly behind that of RORγ+/+ch mice. In an attempt to reverse this, mice were treated with neutralizing mAb to IL-9. As shown in FIG. 3A, the severely impaired melanoma growth in RORγ−/− ch mice was significantly, but not completely, reversed by neutralization of IL-9. These results indicate that this melanoma growth inhibition was partially dependent on IL-9.

Example 3

The Role of IL-9 in Melanoma Immunity in IL-23R−/− Mice

Figure 3D:
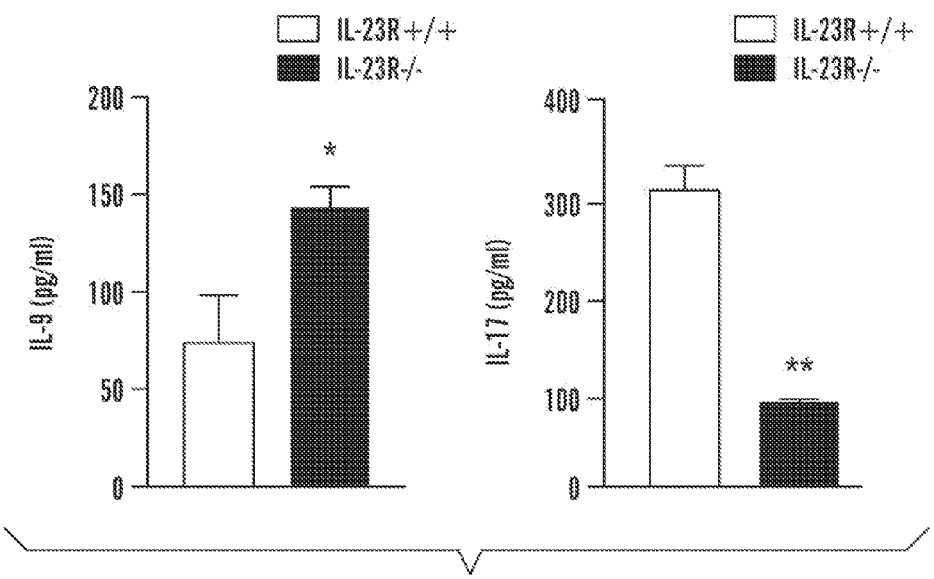

The most strongly downregulated gene in the transcriptional profiling experiments on RORγ−/− CD4 T cells was IL-23R. In addition, expression of IL-23R is necessary for the long-term maintenance of Th17 cells. Melanoma immunity was therefore explored in mice deficient in IL-23R−/− as well. Sorted, naive CD4+T cells were differentiated from IL-23R+/+ and IL-23R−/− mice under Th17 polarizing conditions and demonstrated attenuated development of IL-17A secreting Th17 cells in IL-23R−/− CD4+T cells (FIG. 9B). Interestingly, there was increased expression of IL-9 compared to IL-23R+/+CD4+T cells (FIG. 9B). Next, melanoma cells were injected subcutaneously into IL-23R+/+ and IL-23R−/− mice and additional groups of mice were subsequently treated with anti-IL-9 mAb. Melanoma growth was severely impaired in IL-23R−/− mice. It was next asked, in this completely independent model, what role IL-9 played in this inhibition of tumor growth. Again, neutralization of IL-9 also led to impaired melanoma immunity in IL-23R−/− and IL-23R+/+ (WT) mice (FIG. 9C), suggesting that the production of IL-9 by TIL's observed previously (FIG. 10E) was at least partially effective in tumor growth suppression. Moreover, T cells from tumor draining lymph nodes of IL-23R+/+ (WT) and IL-23R−/− mice secreted IL-9 (FIG. 3D) and there was increased IL-9 secretion by IL-23R−/− T cells compared to IL-23R+/+ (WT).

Example 4

Th9 Cells Inhibit Melanoma Growth

Figure 4A:
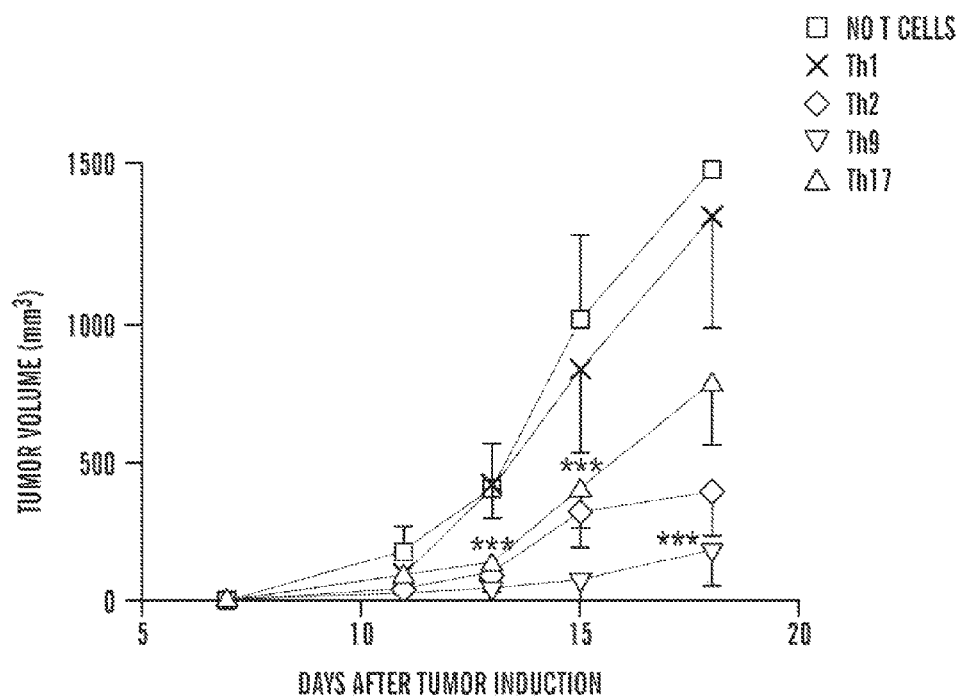
FIGS. 4A-4C depict experiments where differentiated OT2-Th cells from OT2 mice were generated and transferred (iv) into WT mice (WT-C57BL/6.
Figure 11A:
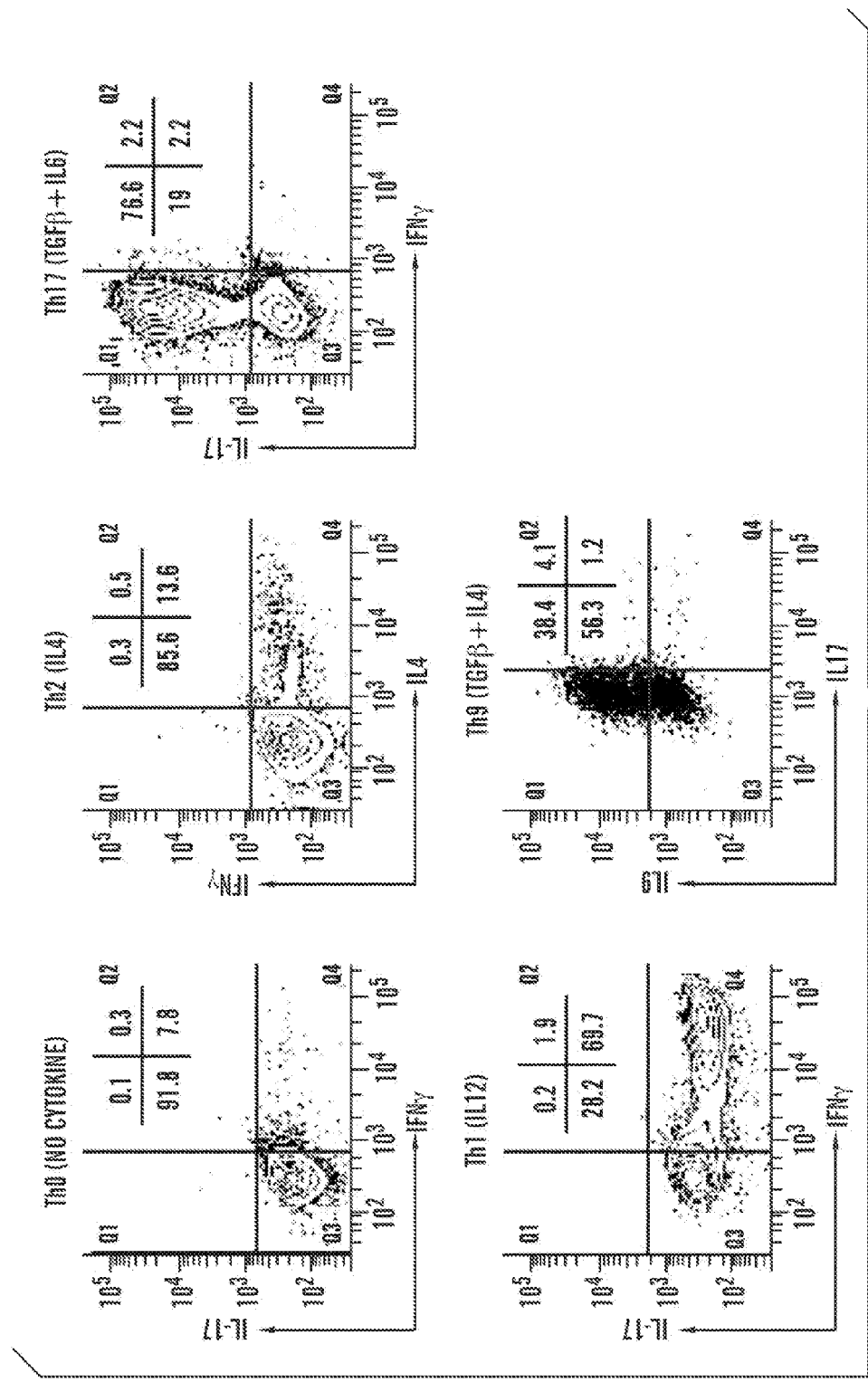
FIGS. 11A-11B depict cytokine expression of differentiated Th cells.

Since IL-9 is mainly produced by CD4+T cells, the role of effector subsets of CD4+T cells in melanoma immunity was examined. Th1, Th2, Th9 and Th17 cells were generated from naive CD4+T cells of OT2 mice. CD4+T cells from OT-2 mice express transgenic TCR that recognizes an Ova-peptide expressed on B16F10-ova melanoma cells. Before adoptive transfer into mice, in vitro cytokine polarized CD4+T cells were analyzed for their cytokine expression. As expected, OT2-Th1 cells produced IFN-γ, OT2-Th2 cells produced IL-4, OT2-Th9 cells produced abundant IL-9, and OT2-Th17 cells produced principally IL-17A (FIG. 11A). Differentiated OT2-Th1, OT2-Th2, OT2-Th9 or OT2-Th17 cells were transferred into syngeneic immunocompetent hosts (WT-C57BL/6). On the same day, B16F10-ova melanoma cells were injected subcutaneously. Mice treated with OT2-Th9 cells showed the most resistance to melanoma growth, and mice treated with OT2-Th17 or OT2-Th2 cells, but not OT2-Th1 cells, showed slower melanoma growth compared to the control group (FIG. 4A).

Figure 4B:
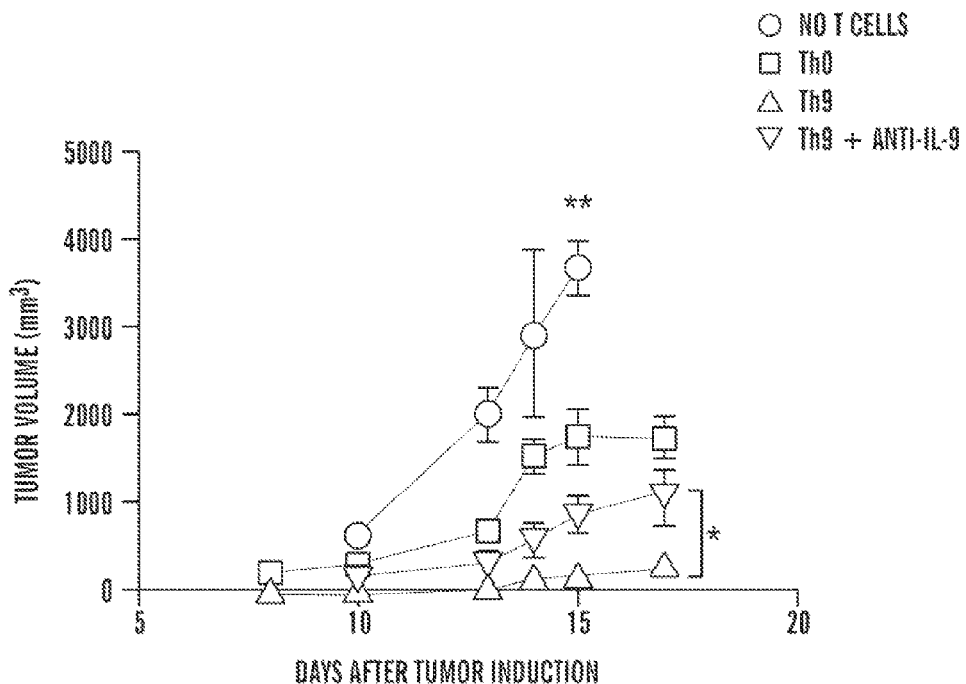
Figure 4C:
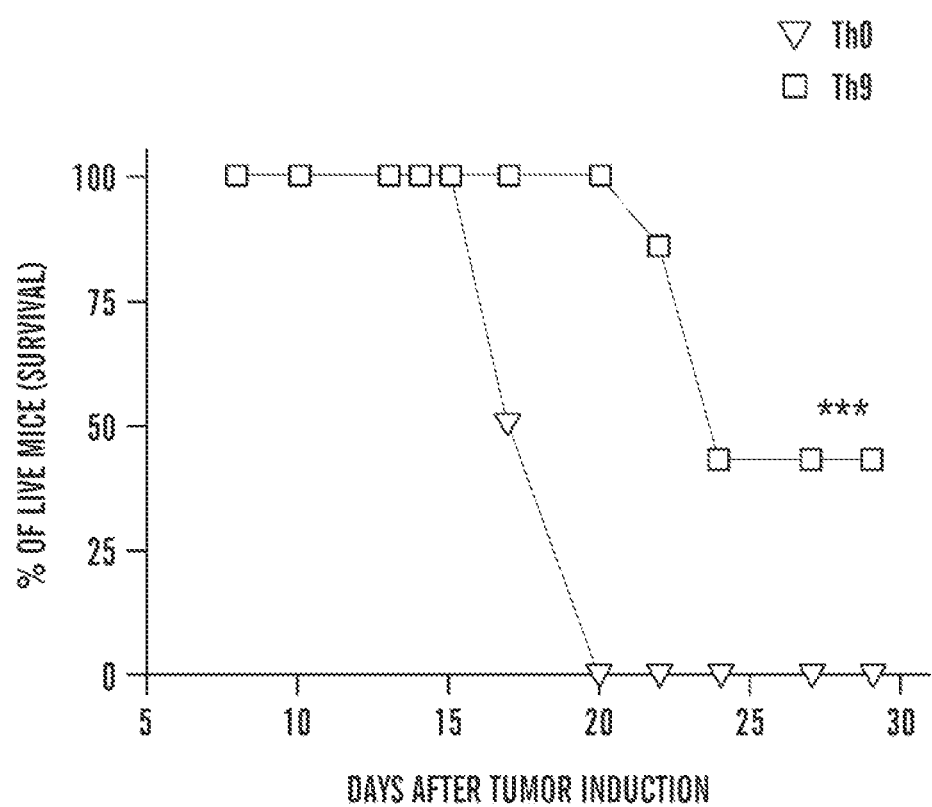

To determine if Th9 cells could inhibit the melanoma development independent of endogenous T cells, OT2-Th0 and OT2-Th9 cells generated from OT2 mice were transferred into immunocompromised hosts (Rag1−/− C57BL/6 mice). Here, OT2-Th9 cells inhibited B16F10-ova induced melanoma growth (FIG. 4B), and survival of OT2-Th9-treated mice was significantly increased compared with control group (FIG. 4C). This data suggest that Th9 cells are capable of inhibiting melanoma development, even in the absence of CD8+T cells. To investigate if IL-9 secreted by OT2-Th9 cells is responsible for the observed anti-melanoma responses, blocking IL-9 was used by neutralizing mAb in OT2-Th9 treated mice (FIG. 4B). IL-9 blockade accelerated melanoma growth in OT2-Th9 treated mice, suggesting at least partial dependence of this effect directly on IL-9.

Figure 11B:
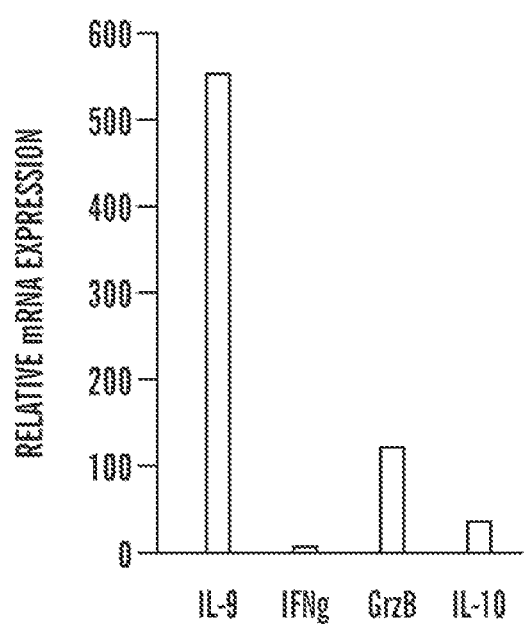
Figure 12A:
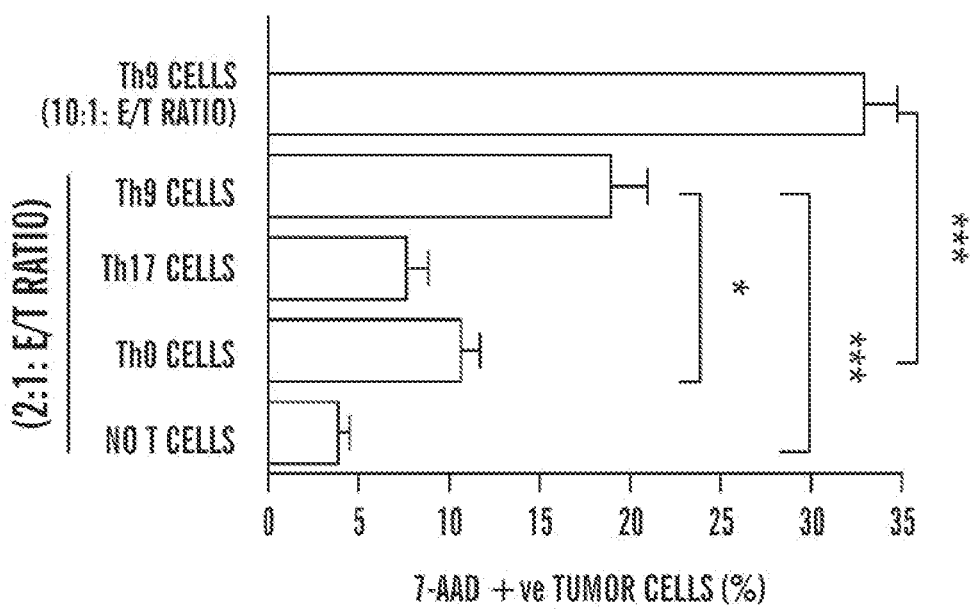
FIGS. 12A-12C depict the results of experiments to determine the ability of various cells to induce apoptosis in melanoma cells.

To determine whether Th9 cells could directly kill melanoma cells, CFSE labeled B16F10-ova cells were co-cultured with OT2-Th9 cells for 24 h. At that point, B16F10-ova cells were recovered and stained with 7-AAD, a sensitive indicator of apoptotic cell death. Strikingly, OT2-Th9 cells alone were capable of inducing apoptosis in melanoma cells, whereas OT2-Th0 and OT2-Th17 cells were much less effective in this regard (FIG. 12A). Next, the mechanism of Th9 cell direct cytotoxicity was assessed. A limited profile of effector molecules in Th9 cells was performed (FIG. 11B). Increased expression of granzyme-B in Th9 cells was observed. Therefore, OT2-Th9 cells were pre-incubated with a granzyme B inhibitor before co-culture with tumor cells to assess the effect on their cytotoxic activity.

Figure 12B:
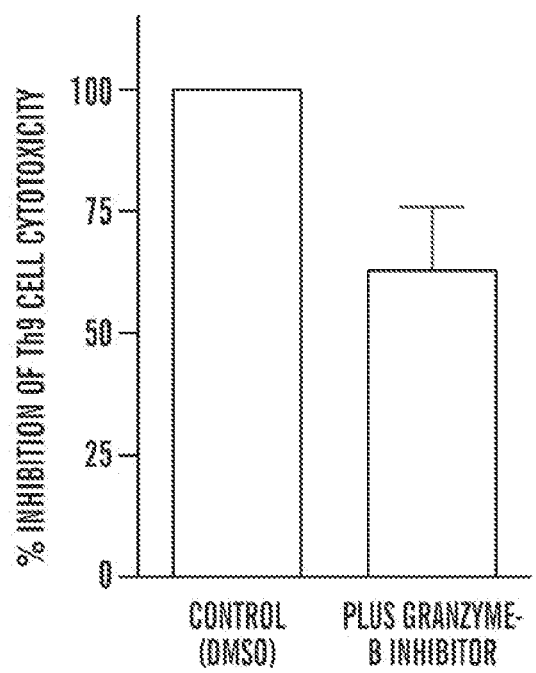
Figure 12C:
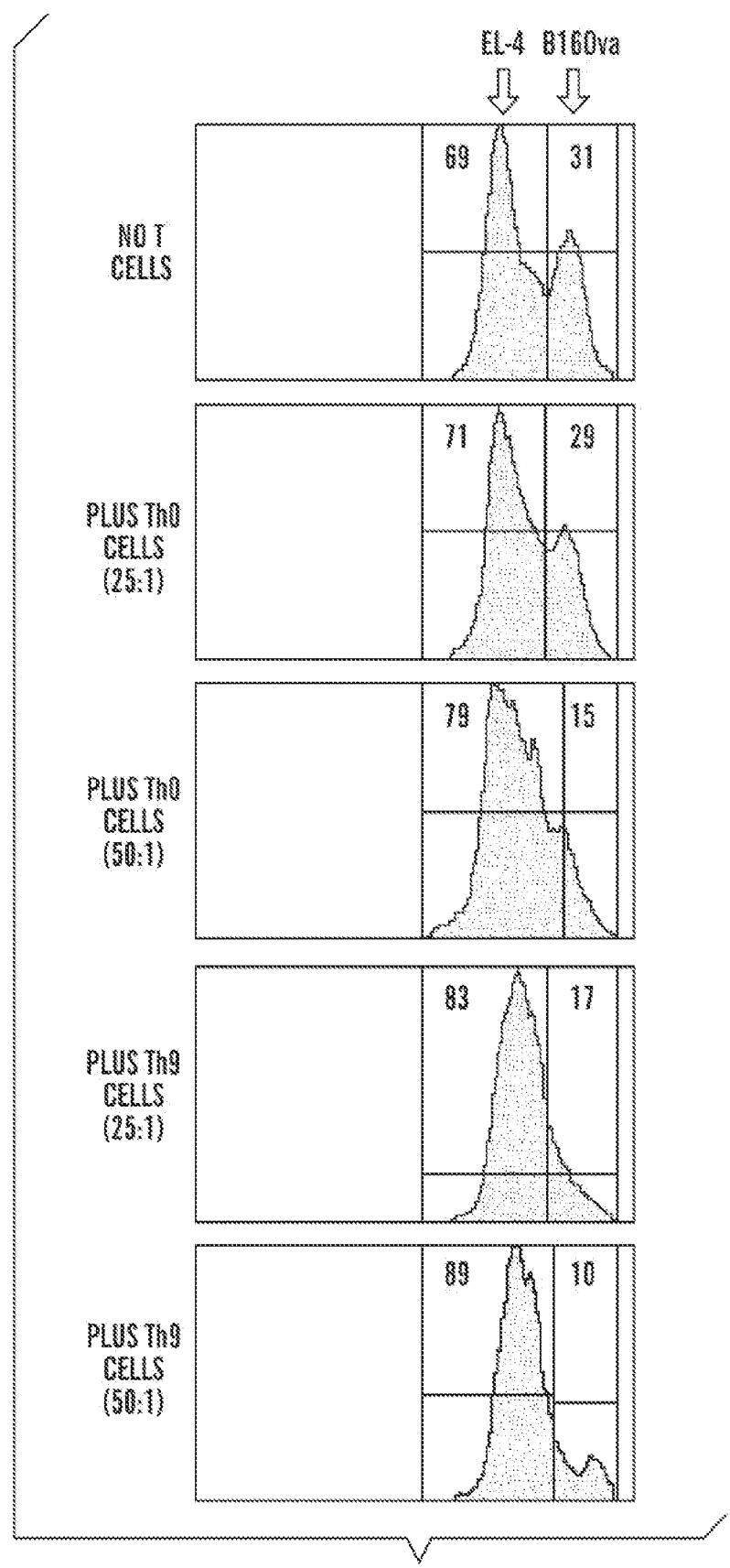

Inhibition of granzyme B significantly attenuated the OT2-Th9 cell cytotoxic activity (FIG. 12B). To further explore the direct cytotoxic effects of Th9 cells, another cytotoxic assay[4] was used. OT2-Th9 cells were incubated with CFSE labeled (5 μM) B16Ova cells and CFSE labeled (0.5 μM) EL-4 cells for 36 h. There were dose dependent effects of Th9 cells on tumor cell lysis (FIG. 12C). More importantly, OT2-Th9 cells killed B16ova cell but not a tumor cell line that did not express Ova, suggesting that Th cell mediated cytotoxic effects are tumor specific (FIG. 12C).

Example 5

Figures 5A, 5B, 5C:
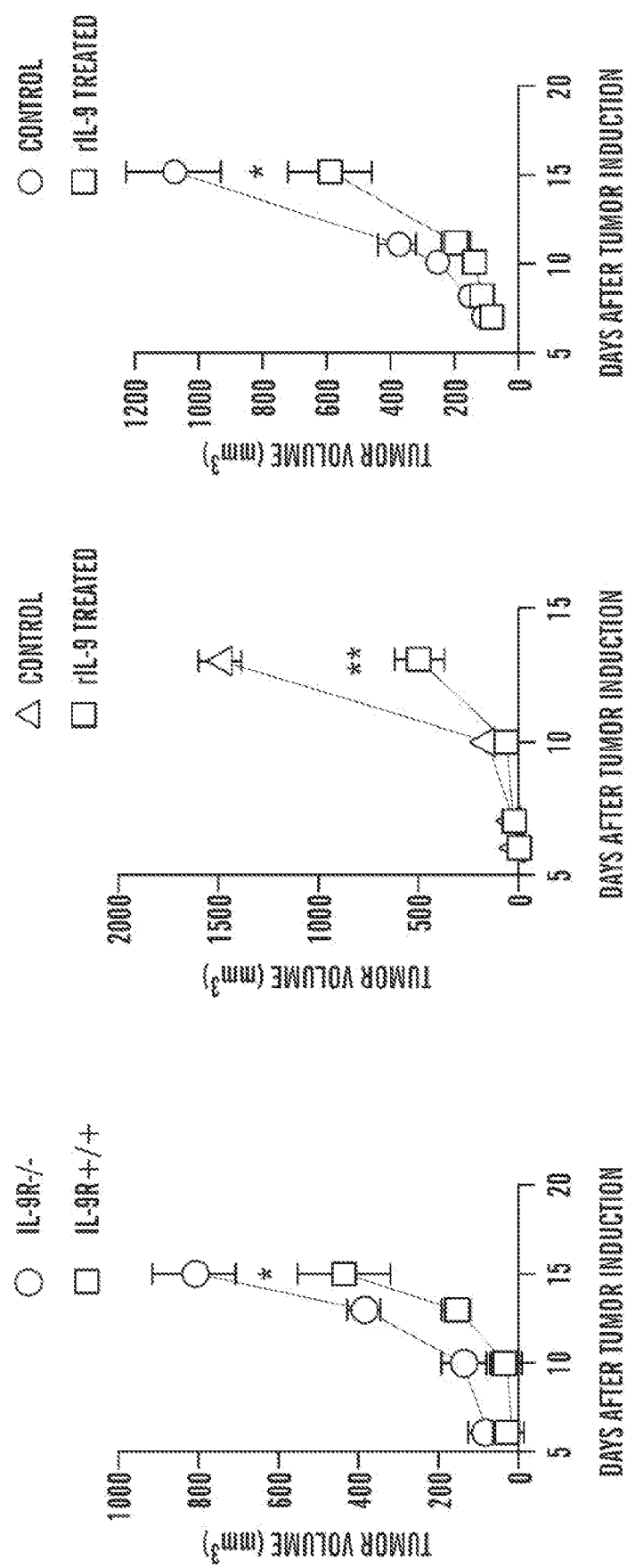
FIGS. 5A-5F depict the results of experiments where various cancer cell types were injected into mice.

Abrogation of IL-9/IL-9R Signaling Promotes Melanoma Development, and Treatment with rIL-9 Inhibits Melanoma Development The results above strongly implicated IL-9 in tumor immunity. To analyze the role of IL-9 in tumor growth more directly, melanoma cells were injected into IL-9R−/− mice, and tumor growth was monitored. Melanoma growth was significantly accelerated in IL-9R−/− mice compared to IL-9R+/− mice (FIG. 5A). It was next asked if administration of rIL-9 could protect mice against melanoma growth and progression. Remarkably, treatment of melanoma bearing mice with recombinant IL-9 (rIL-9) both impaired melanoma growth (FIG. 5B) and increased the survival of mice (data not shown). To examine if rIL-9 could potentiate the anti-melanoma response in mice already vaccinated against melanoma, mice were treated with 1 million irradiated melanoma cells (as vaccine) and 7 days later, melanoma cells were injected. Mice were treated with rIL-9 or with PBS alone. Again, rIL-9 treated mice showed significantly slower melanoma growth (FIG. 4A). To investigate the role of IL-9 in tumors other than melanoma, Lewis lung carcinoma (LLC-1) cells were used. LLC-1 tumor development was significantly suppressed in rIL-9 treated mice compared with a control group (FIG. 5C), consistent with the extensive observations with B16 melanoma tumors described above herein.

Example 6

Mast Cells, but not Adaptive Immune Cells, are Required for the Anti-Tumor Effect of IL-9

Figures 5D, 5E, 5F:
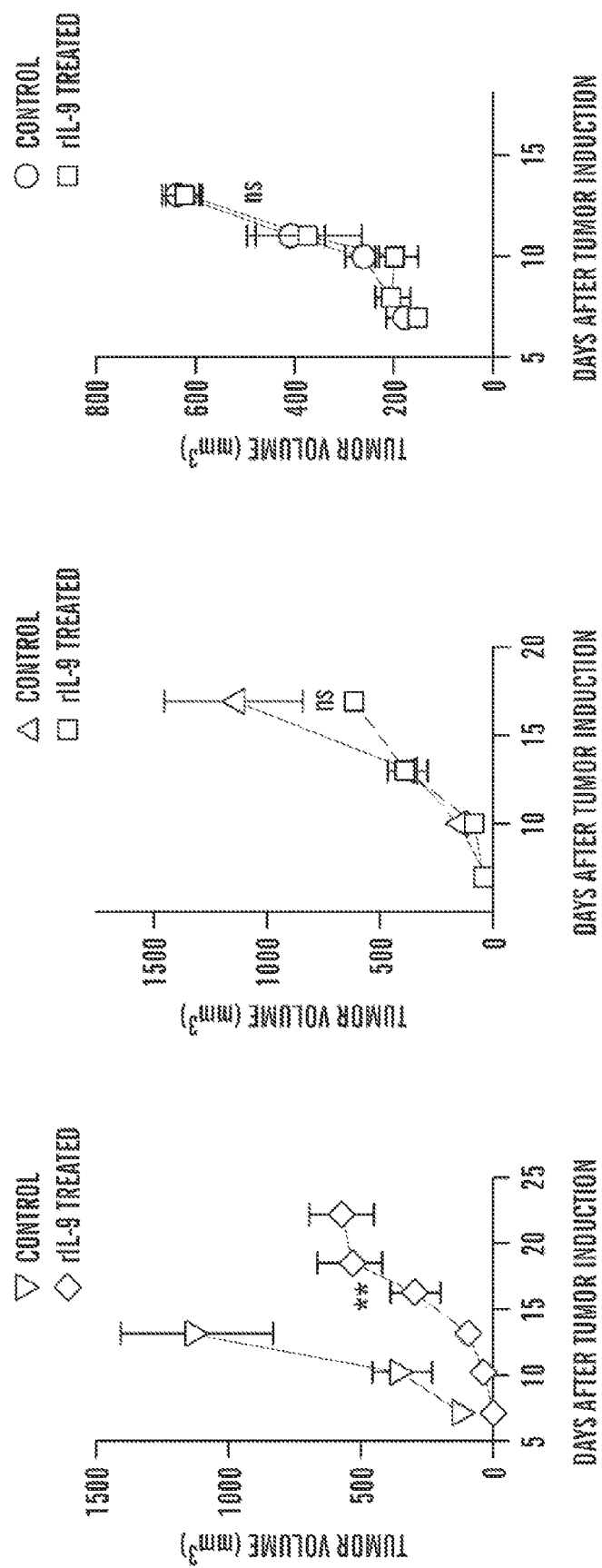

Subsequently, the mechanism of IL-9 mediated tumor immunity, specifically as it relates to T cells, was investigated. Melanoma cells were injected into Rag1−/− C57BL/6 mice, which lack T and B cells. These mice were treated with either rIL-9 or PBS (control). In this setting, rIL-9 treatment still significantly slowed melanoma growth (FIG. 5D), suggesting that the target of the IL-9 effect was not a T cell or B cell. IL-9 is also known to promote mast cell development and function, so mast cell deficient mice (Kit W-sh/HNihrJaeBsmJ) were injected with B16 melanoma and lewis lung carcinoma cells (LLC-1), respectively, treated mice systemically with rIL-9 in the same fashion, and measured tumor growth (melanoma: FIG. 5E, LLC-1: FIG. 5F). Strikingly, under these conditions, there was no significant difference in tumor development in IL-9 treated mast cell deficient mice, as compared to control. These highly reproducible data suggest that tumor growth inhibition mediated by IL-9 depends upon the presence of mast cells, but not on the presence of T cells or B cells. Moreover, the anti-tumor effect of IL-9 was seen on two different tumor cell lines of completely different development cellular origin: LLC-1 and B16 melanoma.

Example 7

Figure 6A:
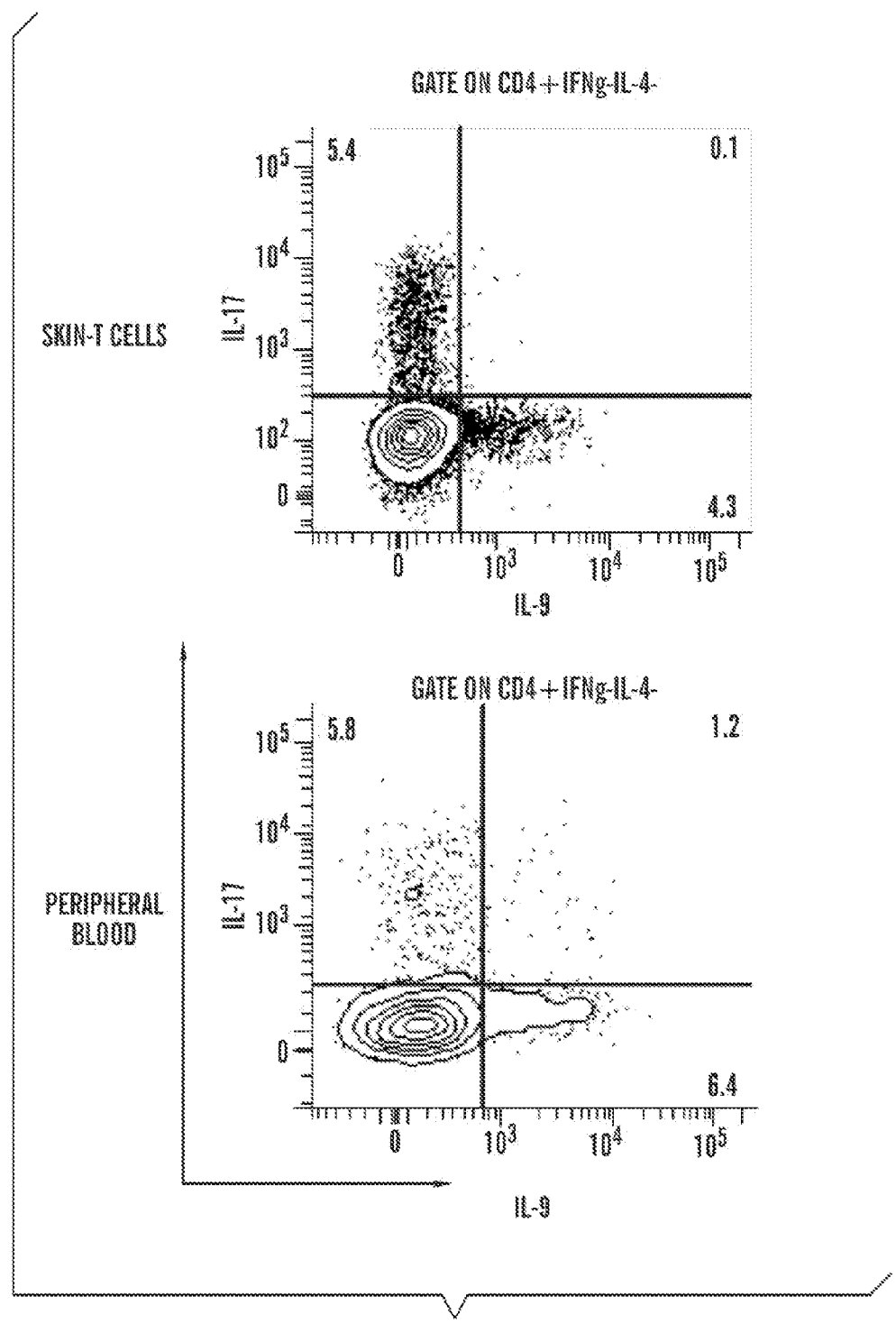
FIGS. 6A-6C depict the results of experiments to detect T cells in human samples.
Figure 6B:
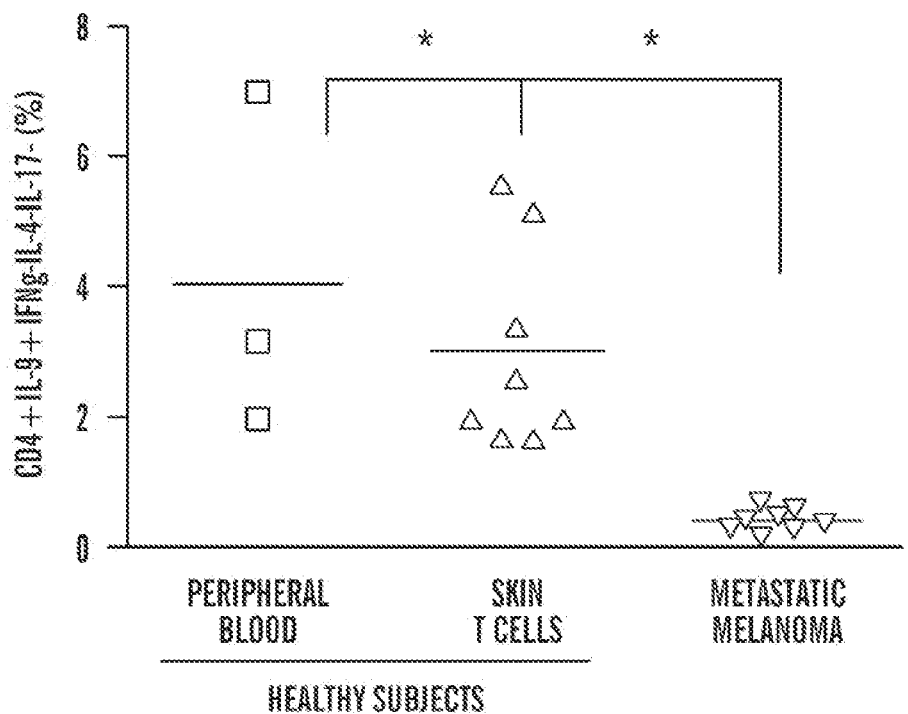
Figure 6C:
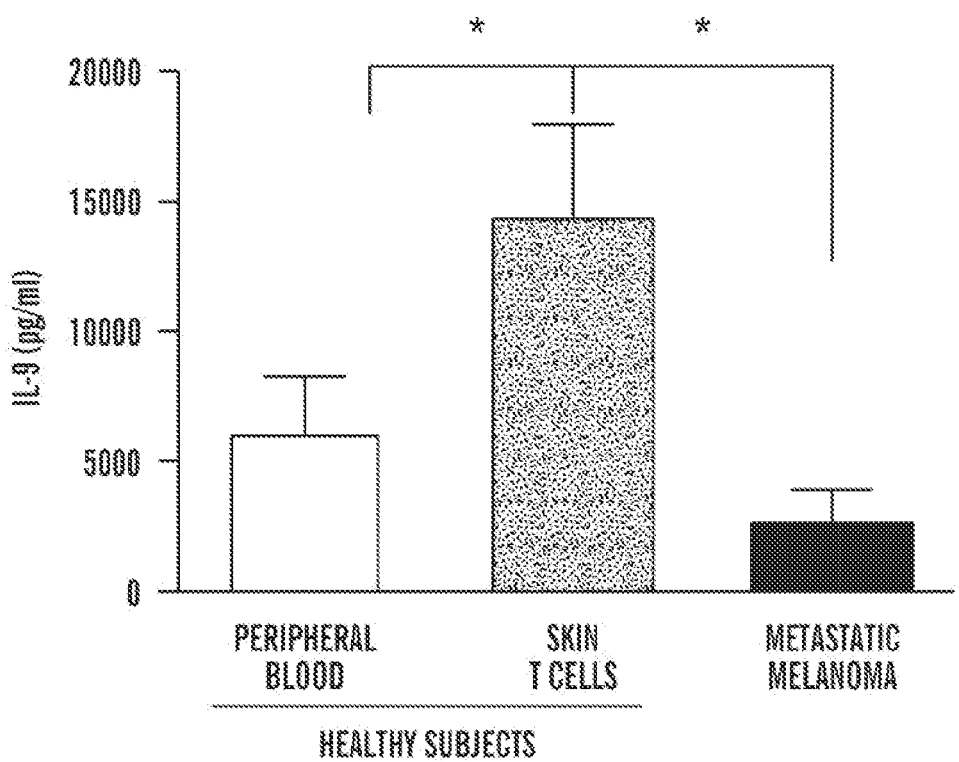

Presence of IL-9 Producing T Cells (Th9 Cells) in Human Skin and Peripheral Blood The existence of human Th9 cells is controversial; for this work to be relevant to melanoma patients, these cells were identified in human tissues. Specifically, it was asked if IL-9 producing Th9 cells can be identified in humans, and if so, do they possess a phenotype comparable to mouse Th9 cells. Mouse Th9 cells are defined as a distinct population of CD4+T cells that produce IL-9 but not IFNγ (Th1), IL-4 (Th2) or IL-17 (Th17). It was possible to demonstrate that human memory T cells isolated from peripheral blood contained a distinct population of IL-9 producing T cells that does not produce IFNγ, IL-4 and IL-17. T cells with an identical phenotype, and in greater abundance, were also found skin-resident T cells isolated from healthy skin (FIGS. 6A-6B). Finally, the presence of IL-9 producing T cells in T cells extracted from patients with Stage IV unresectable metastatic melanoma was examined (metastasis to lung (n=4), skin (n=2), adrenal gland (n=1), bone (n=1)). Detectable IL-9 producing T cells were observed in 6 out of 8 biopsies; however, this IL-9 production was significantly lower in T cells from metastatic melanoma compared with T cells extracted from healthy donors (FIG. 6c).

Described herein are five findings: 1) Mice deficient in pathways related to Th17 development (RORγ−/− and IL-23R−/−) show significant resistance to melanoma growth in a fashion that is largely IL-9 dependent; 2) Th9 cells inhibit tumor growth in an IL-9 dependent fashion; 3) mice deficient in IL-9 signaling, either by germline inactivation of the receptor gene or by antibody blockade, exhibit enhanced melanoma growth; 4) treatment of tumor bearing mice with exogenous rIL-9 inhibits tumor growth in normal mice, and this effect is dependent on the presence of mast cells but not T and B cells; and 5) memory Th9 T cells can be identified in normal human blood and skin, and are present at reduced levels in metastatic melanoma lesions.

At the outset of the study, the goal was to assess the role of Th17 cells in melanoma immunity; thus, RORγ−/− ch mice and IL-23R−/− mice, which can not generate or maintain Th17 cells, respectively, were used. Melanomas implanted in RORγ−/− mice and IL-23R−/− showed impaired growth and increased tumor infiltration by T cells, suggesting an important role for the Th17 pathway in tumor immunity. However, the role of other pathways remained an open question.

To explore the expression of unknown factors with anti-tumor properties, gene expression analysis was performed with CD4+T cells of RORγ−/− and RORγ+/+ controls differentiated under Th17 polarizing conditions. This analysis revealed a striking increase in IL-9 expression in RORγ−/− Th cells. These data indicate that absence of RORγ promotes IL-9 expression. Little is known about the regulation of IL-9. Recent studies have suggested that IL-25 and IL-21 enhance IL-9 expression in mice and humans, respectively[22][23]. The precise mechanism by which the absence of RORγ promotes IL-9 expression in T cells is not known, although analysis of the IL-9 promoter does not reveal an RORγ binding site (data not shown). However, the data presented herein demonstrates severely impaired IL-23R expression on RORγ−/− CD4+T cells. In concert, increased IL-9 expression was observed in IL-23R−/− CD4+T cells. Therefore, attenuated signaling via IL-23R expression in RORγ−/− CD4+T cells might be one of the factors responsible for increased in IL-9 expression. To evaluate if increased IL-9 expression is critical for the observed anti-melanoma responses in RORγ−/− ch mice and IL-23R−/− mice, IL-9 was blocked by treating mice systemically with a neutralizing anti-IL-9 antibody. Depletion of IL-9 in both RORγ−/−ch mice and IL-23R−/− and normal WT mice clearly accelerated melanoma growth.

Since IL-9 is primarily a product of CD4+T cells, the role of IL-9 producing Th cells (Th9 cells) in tumor immunity was explored. Mice treated with Th9 cells showed profound resistance to melanoma development. This is believed to be the first report demonstrating anti-tumor effect of Th9 cells. Previous studies have reported that adoptive transfer of Th9 cells can induce colitis and peripheral neuritis in lymphopoenic host[24], indicating significant immune effector function mediated by these cells. Similar to previous reports[6,13,25], Th2 and Th17 cells, but not Th0 and Th1 cells inhibited melanoma growth in the experiments described herein. However the anti-melanoma properties of Th9 cells were far superior to Th17 cells, in both immunocompetent and immunocompromised hosts.

In vitro, Th9 cells showed modest but measurable direct cytotoxic activity on melanoma cells, a novel and striking observation. Increased expression of Granzyme B and C was also observed in Th9 cells, a possible mechanism of Th9 cell direct cytotoxicity, and a Granzyme B inhibitor was shown to partially block Th9 mediated melanoma cytotoxicity. Therefore, it appears that Th9 cells possess robust anti-melanoma activity mediated in large part by direct release of IL-9. However, in this setting, blockade of IL-9 in Th9 treated mice accelerated tumor growth, suggesting that Th9 cell anti-melanoma activity is significantly IL-9 dependent.

Figure 10B:
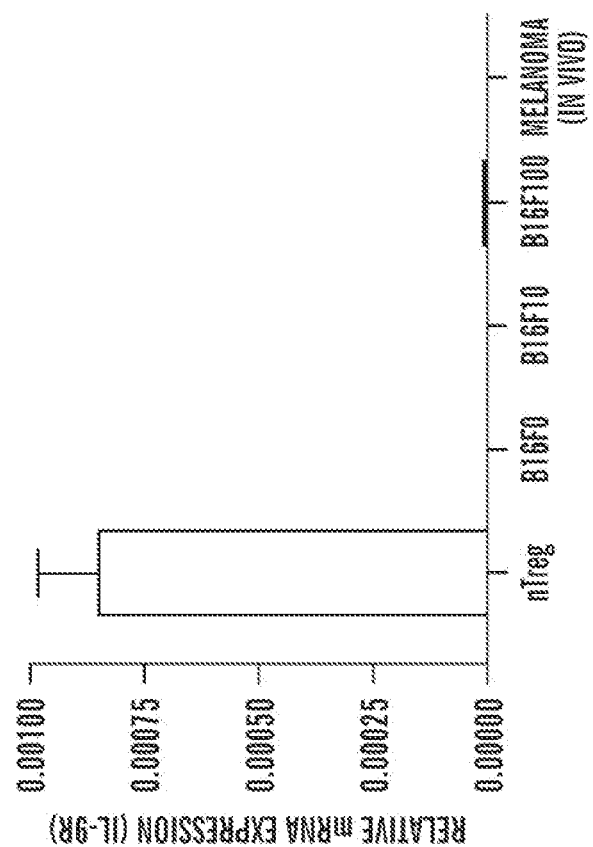
Figure 10A:
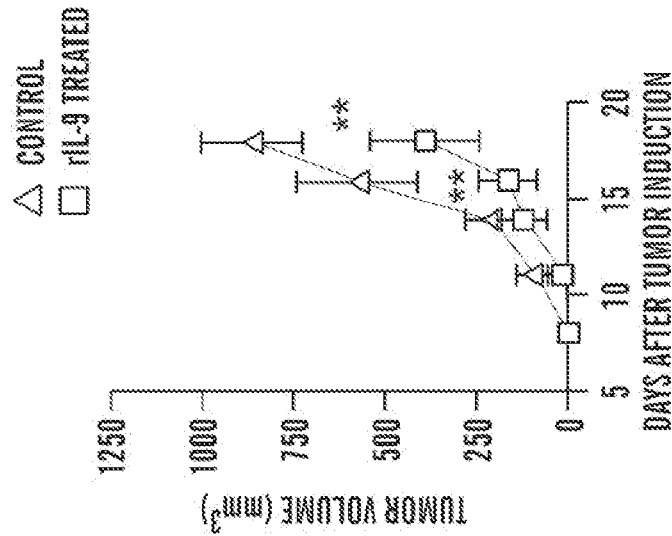
Figure 10E:
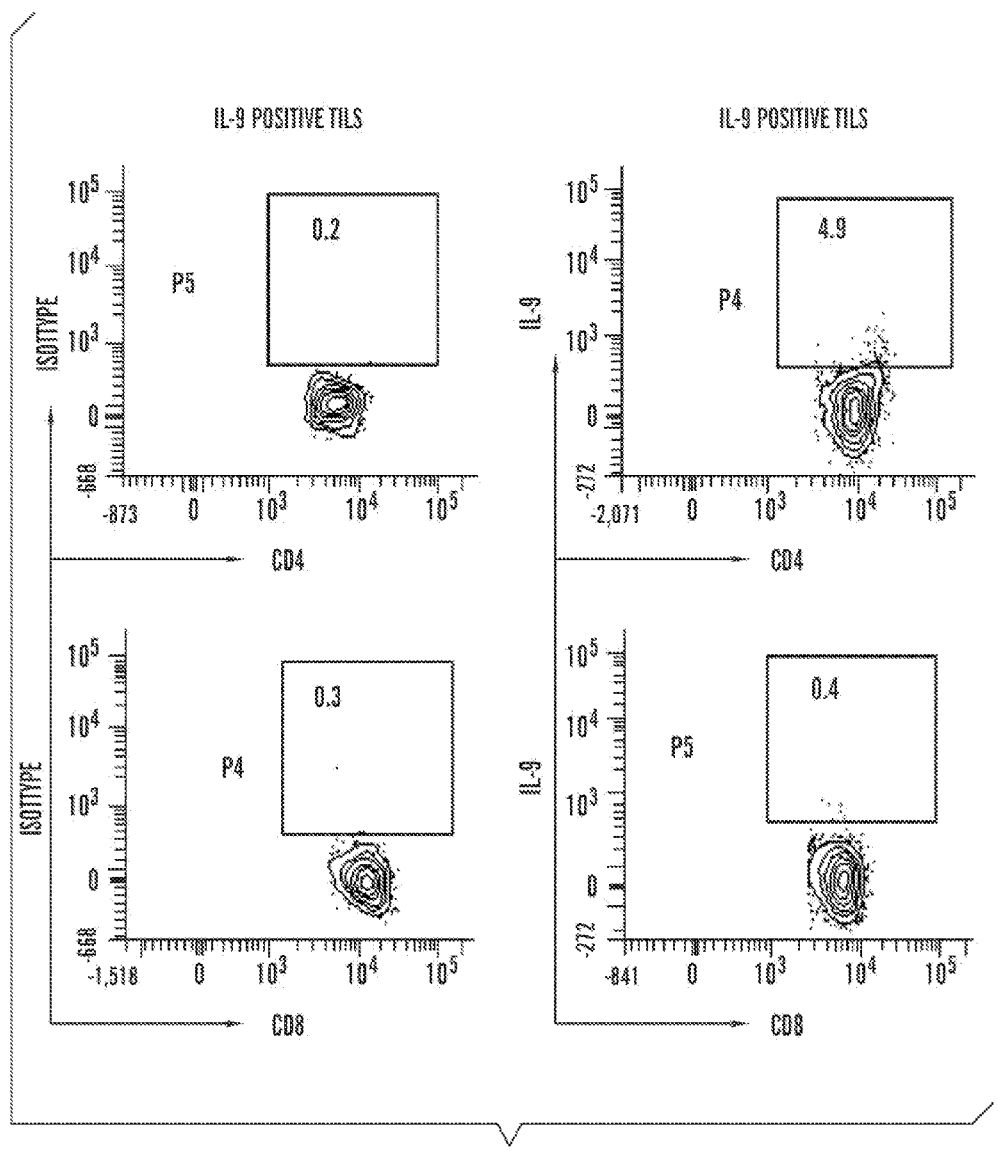

To determine independently whether IL-9 has anti-melanoma activities, melanoma growth was studied in IL-9R−/− mice. Melanoma growth was reproducibly accelerated in IL-9R−/− mice. These data indicate that IL-9 appears to be an independent factor that influences tumor growth. The data also indicate that treatment with exogenous IL-9 reproducibly suppresses the growth of B16 melanoma in the same tumor model. To rule out the possibility that this process was unique to a single tumor type, it was asked whether the growth of a lung carcinoma cell line could be similarly inhibited. Reproducibly, LLC-1 growth was significantly inhibited by IL-9. To rule out the unlikely possibility that this was a direct effect of IL-9 on the tumor cells, IL-9R expression on tumor cells was investigated and the direct effects of IL-9 on tumor cell growth was examined (FIGS. 10B-10D). EL-4 T lymphoma cells were used as a control. Melanoma cells and lung carcinoma show negligible IL-9R expression and IL-9 does not affect the growth of these cells in vitro, suggesting that IL-9 mediated anti-tumor effects on melanoma cells and on lung carcinoma cells are indirect. However, increased IL-9R expression on EL-4 cells was observed (FIG. 4C). It was asked if the growth of this tumor could be inhibited by IL-9, and neither inhibition nor acceleration of EL-4 tumor growth was observed (data not included). This suggests that the presence of IL-9R on EL-4 cells, and previously reported growth and survival promoting properties of IL-9 T cells, may be accountable for negligible anti-tumor effect of IL-9 in this tumor model[26]. Therefore, these data indicate that the anti-tumor effects of IL-9 are indirect, and also indicates that potential tumor targets of rIL-9 therapy should be selected with care: specifically, lymphomas and other cells known to express receptors for this cytokine may not be appropriate candidates for treatment.

To explore the adaptive immune-mediated anti-tumor effects of IL-9, it was asked if the tumor inhibitor effect of IL-9 would be preserved in mice deficient in T and B cells. Strikingly, no difference was found in the degree of tumor inhibition mediated by exogenous IL-9 between normal and Rag-1−/− mice. This suggests that if anything, the effect of IL-9 on the adaptive immune system is not sufficient to mediate the beneficial effects of IL-9 in tumor growth inhibition. Furthermore, it appears that the anti-melanoma properties of IL-9 are neither mediated via direct effect on T or B cell activation nor via direct effects on tumor cells.

Because the effect of exogenous IL-9 appears to be independent of T and B cells, and because the anti-tumor effects of Th9 cells can be largely abrogated by neutralizing antibodies to IL-9, other immune cells that might be targets for IL-9 were sought. IL-9 is a potent activator of mast cells, a cell type that has recently been implicated in anti-tumor activity[27]. Therefore, mast cell deficient mice were used to study the IL-9 mediated anti-tumor effect. Strikingly, rIL-9 treatment was observed to have no inhibitory effect on tumor growth in mast cell deficient hosts, suggesting that mast cells play an important role in the anti-tumor activity mediated by IL-9. Future studies are needed to delineate how IL-9 modulates the mast cell anti-tumor activity (survival, and/or function).

Finally, there has been some controversy about whether Th9 cells were a purely murine phenomenon, and therefore not relevant to human disease. Human skin and blood were examined for the presence of memory T cells that could produce IL-9. IL-9 producing T cells were readily found in populations of human skin resident memory T cells and in the memory T cell population of PBMCs. Importantly, these IL-9 producing human T-cells appear to be authentic analogs of murine Th9 cells, as they do not produce other Th cell lineage cytokines such as IFN-γ (Th1), IL-4 (Th2), and IL-17 (Th17). Production of IL-9 by T cells in tumor draining lymph nodes in the B16 melanoma model was demonstrated, and therefore it was asked whether Th9 cells could be found in human metastatic melanoma samples. In 6 of 8 samples, the presence of memory Th9 TIL's could be detected, but at a much lower abundance than memory Th9 cells in either normal skin or blood. The finding of low levels of Th9 T cells in human metastatic melanoma is interesting. These results suggest that Th9 cells are part of the normal human immune response to melanoma, and thus augmenting their activity, or providing additional IL-9, should be therapeutically advantageous in this setting.

The role of IL-9 in tumor immunity has not been previously explored. Interestingly, however, single nucleotide polymorphisms in IL-9 gene were found to be associated with increased risk of cutaneous malignant melanoma (CMM)[28]. Therefore, IL-9 was suggested as one of the highly significant modifier genes for CMM using pathway permutation analysis. A very recent paper by Smith et al[29] reported that blockade of endogenous IL-9 alone does not enhance the survival of tumor bearing mice; however, in combination with CpG therapy anti-IL-9 increases the survival of Balb-neu T mice. These investigators speculate that blockade of IL-9 signaling inhibits Treg function and thus promotes vaccine induced effector T-cell mediated anti-tumor responses. As described herein, however, blockade of endogenous IL-9 invariably accelerated tumor development in the B16 melanoma model, and the absence of IL-9 signalling (i.e., IL-9R−/− mice) also enhanced melanoma growth. The discrepancy between the results described herein and that of Smith et al is difficult to reconcile; however, there are clear differences between the experimental design described herein and that of Smith et al[29]. First, the tumor models used were distinct. In addition, the experiments described herein did not use vaccine or adjuvant in combination with endogenous IL-9 blockade or with exogenous IL-9 treatment to boost adaptive immune response. In summary, all of the experiments described herein, using a large number of different variables, were consistent with a distinct anti-tumor effect of IL-9. The data presented herein also show that this anti-tumor effect was largely mediated by mast cells, which have not been reported to be targets of Treg inhibition.

In conclusion, described herein is an unexpected role of IL-9 and Th9 cells in anti-tumor immune responses. Strategies that favor generation of IL-9 mediated immune responses, while blocking IL-17 mediated responses, may have an important clinical role in the treatment of melanoma. Other γc chain cytokines, such as IL-2, IL-15, and IL-21[30-32], have been used in the treatment of human melanoma, and the data presented herein indicate that IL-9 and Th9 cells have an important role in treatment of this challenging malignancy.

Methods

Mice.

WT C57BL/6, Rag1−/− C57BL/6 and IFNγ−/− mice were obtained from Jackson Laboratories. IL-9R−/−, IL23R−/− and RORγ−/− and their control mice (RORγ+/+, IL9R−/+) were provided by Jean-Christophe Renauld[33] (Ludwig Institute, Belgium), V K Kuchroo[34] (BWH) and A M Jetten[18] (NIH), respectively. Mice were housed in conventional, pathogen-free facilities at the animal facility of Harvard Medical School.

In Vitro T Cell Differentiation.

CD4+CD25-CD62Lhigh cells from RORγ−/− mice or RORγ+/+ controls were sorted by CD4+CD62L+ isolation kit II from Miltenyi Biotech (USA) according to manufacturer's protocol. Purity of CD4+CD25-CD62Lhigh was >95%.

Sorted CD4+CD25-CD62Lhigh cells were differentiated into Th1 (IL-12:10 ng/ml), Th2 (IL-4: 10 ng/ml), Th9 (TGF-β plus IL-4: 1 ng/ml and 10 ng/ml), and Th17 (TGF-β plus IL-6: 1 ng/ml and 10 ng/ml) in presence with plate bound anti-CD3 (1 μg/ml) and irradiated splenocytes (1:5 ratio). After 48 h cells were fed with IL-2 (10 ng/ml) containing fresh media and split into two parts, if needed. On day 5, cells were harvested and processed for cytokine analysis at RNA or protein level by real-time RT-PCR, flow cytometry and ELISA.

For adoptive transfer experiments, CD4+Th cells differentiation was carried out using above mentioned protocol with few modifications. Plate bound anti-CD3 (2 μg/ml) and anti-CD28 (1 μg/ml) was used in place of irradiated splenocytes. In addition to above mention polarization condition, anti-IFNγ mAb (10 μg/ml) was added into Th9 cultures and anti-IFN-γ mAb (10 μg/ml) plus anti-IL-4 mAb (10 μg/ml) was added into Th17 cultures.

Tumor (Melanoma, Lewis Lung Carcinoma and Thymic Lymphoma) Induction, In Vivo T Cell Transfer and IL-9 Neutralization.

Melanoma cell lines (B16F10 cells or B16F10-ova cells), T cell lymphoma (EL-4 or ovalbumin expressing EL-4 (EG-7)) and Lewis lung carcinoma (LLC1) were grown in RPMI1640 supplemented with 10% FBS, and penicillin/streptomycin. B16F10 cells (2-4×10$^5$ cells/150 μl/mouse), EL-4 (2×10$^5$ cells/150 μA/mouse), or LLC1 (5×10$^5$ cells/150 μA/mouse) were injected subcutaneously into the right or left flank of the mice and tumor development was monitored over time. Tumor volume was calculated by following formula: (major circumference×minor circumference$^2$)/2. Mice were sacrificed when there was external necrosis or/and tumor volume reached no greater than 2 cm in any direction.

To investigate the role of effector subsets of Th cells on melanoma and thymic lymphoma growth, 2-million differentiated cells (Th1, Th2, Th9 and Th17) from CD45.1+CD45.2-OT2 TCR transgenic mice were injected (iv) into WT-C57BL6 mice or Rag1−/− (C57BL6 background)) mice and, on the same day tumor cells (B16F10-ova cells: 3×10$^5$ cells/150 μl/mouse) were injected subcutaneously. Tumor growth was monitored over time.

IL-9 activity in vivo was neutralized by injecting (i.p.) 100 μg anti-IL-9 mAb (clone: MM9C1, a generous gift by Jacques van Snick (Ludwig Institute, Belgium)) for 4 times on day 0, day 3, day 6 and day 10. Melanoma cells were injected on day 0 and melanoma growth was monitored over time.

rIL-9 (5 μg/100 μA PBS/mouse from Cell Sciences, USA) was injected (ip) from day 0 and every third day till the termination of the experiment. In lewis lung carcinoma (LLC-1) model, rIL-9 (50 ng/100 μl PBS/mouse from RnD systems) was used on every alternate day till the termination of experiment. Unlike Cell Science rIL-9 (source: *E. coli*), rIL-9 from RnD systems is glycosylated and therefore has stronger biological activity compared to Cell Sciences. Thus, 100 times less rIL-9 was used in LLC-1 tumor model experiments compared to melanoma model experiments. In addition, melanoma bearing mice were treated with rIL-9 from RnD systems which produced similar results as were observed with rIL-9 from Cell Sciences (data not shown).

Cytotoxicity Assay.

For the cytotoxicity assay, CFSE labeled B16F10-ova cells (5×10$^5$ cells/500 μl) were cultured with differentiated Th cells (OT2-Th0, OT2-Th9 and OT2-Th17) in several different ratios. After 24 h of co-culture, cells (gate on CFSE labeled B16F10-ova cells) were analyzed for 7-AAD staining by flow cytometry. In addition, another cytotoxicity assay was used as described before[4].

Growth Curve Assay.

Effect of rIL-9 on growth of B16F10 cells were studied by growth curve assay. B16F10 cells were seeded with rIL-9. After each incubation period cells were fixed (10% acetic acid in 10% ethanol). Cells were subsequently stained with 0.4% crystal violet in 10% ethanol for 30 min. Subsequently, 200 µl 10% acetic acid was added. After 30 min, 100 µL solution was transferred into 96-well plate and OD was measured at 595-wavelength.

Measurement of Cytokines by Intracellular Cytokine Staining, CBA, ELISA and Quantitative RT-PCR.

Intracellular cytokines by Lymph node (LNs) cells, splenocytes, TILs or in vitro differentiated Th cells were quantified after restimulation with PMA plus ionomycin and GolgiStop™ ss described previously[35].

Cytokines were quantified in cell free culture supernatants by cytometric bead array (CBA by BD Biosciences) or by ELISA (eBioscience) according to the manufacturer's instructions.

RNA was extracted with High pure RNA isolation kit (Roche), cDNA was made by First strand cDNA synthesis kit (BioRad) and quantitative RT-PCR was done using multiplex kit (BioRad) on iCycler™ real time PCR detection system (BioRad) according to the manufacturer's instructions. IL-9R PCR was carried out by using IL-9R specific TaqMan™ (Thermofisher) probes and AB Biosystem PCR machine.

Cell Purification, Sorting, Intracellular Cytokine Staining and Cytokine Quantification in Supernatants (Human Study).

PBMCs were isolated from buffy coats of healthy donors by density centrifugation. Memory CD4+T cells were purified from freshly isolated PBMCs by negative selection using a Memory CD4+ T cells Isolation Kit (Miltenyi Biotech, Germany) and stimulated with anti-CD3/CD2/CD28 beads (Milyenyi) in presence of TGFb (3 ng/ml).

Normal human skin samples were obtained as discarded material after cosmetic surgery according to Institutional Review Board of Partners Human Research Committee. Total skin T cells from healthy donors and T cells of melanoma metastasis were isolated from explant cultures grown with IL-2 and IL-15 as previously[36] described.

Activated memory T cells from PBMCs, and skin T cells and T cells of melanoma metastasis isolated by the explant culture technique were stimulated for 5 h in the presence of PMA/ionomycin (Sigma-Aldrich) plus Brefeldin A. After incubation, CD4+T cells were stained for IFNγ (anti-IFNγ: B27), IL-4 (anti-IL-4: MP4-25D2), IL-9 (antiIL-9: MH9A4) and IL-17 (anti-IL-17: eBio64DEC17,) using standard intracellular staining and analyzed by flow cytometry[35].

Memory T cells from blood, skin and melanoma metastasis were stimulated at $10^6$ cells/ml with beads coated with αCD3/αCD2/αCD28 (bead:T cell ratio: 1:2 from Miltenyi Biotech) in the presence of IL-2 (50 IU/ml) and TGF-β (3 ng/ml) for 2 days. IL-9 in culture supernatants was measured by Luminex bead-based multiplex assays using a custom-made Luminex bead assay as described previously[37].

Statistical Analysis.

Student t-test (two tailed) was performed for the data analysis using GraphPad Prism software program. A paired t-test was used in FIGS. 8H and 8J. The p value <0.005, 0.025 and 0.05 are represented as *,  and * respectively.

All the references cited below and cited throughout the specification, are herein incorporated by reference in their entirety.

REFERENCES OF THE EXAMPLES

1. Hodi, F. S., et al. Improved survival with ipilimumab in patients with metastatic melanoma. *N Engl J Med* 363, 711-723 (2010).
2. Mumberg, D., et al. CD4(+) T cells eliminate MHC class II-negative cancer cells in vivo by indirect effects of IFN-gamma. *Proc Natl Acad Sci USA* 96, 8633-8638 (1999).
3. Perez-Diez, A., et al. CD4 cells can be more efficient at tumor rejection than CD8 cells. *Blood* 109, 5346-5354 (2007).
4. Quezada, S. A., et al. Tumor-reactive CD4(+) T cells develop cytotoxic activity and eradicate large established melanoma after transfer into lymphopenic hosts. *J Exp Med* 207, 637-650 (2010).
5. Xie, Y., et al. Naive tumor-specific CD4(+) T cells differentiated in vivo eradicate established melanoma. *J Exp Med* 207, 651-667 (2010).
6. Mattes, J., et al. Immunotherapy of cytotoxic T cell-resistant tumors by T helper 2 cells: an eotaxin and STAT6-dependent process. *J Exp Med* 197, 387-393 (2003).
7. Numasaki, M., et al. Interleukin-17 promotes angiogenesis and tumor growth. *Blood* 101, 2620-2627 (2003).
8. Numasaki, M., et al. IL-17 enhances the net angiogenic activity and in vivo growth of human non-small cell lung cancer in SCID mice through promoting CXCR-2-dependent angiogenesis. *J Immunol* 175, 6177-6189 (2005).
9. Wang, L., et al. IL-17 can promote tumor growth through an IL-6-Stat3 signaling pathway. *J Exp Med* 206, 1457-1464 (2009).
10. Benchetrit, F., et al. Interleukin-17 inhibits tumor cell growth by means of a T-cell-dependent mechanism. *Blood* 99, 2114-2121 (2002).
11. Kryczek, I., et al. Phenotype, distribution, generation, and functional and clinical relevance of Th17 cells in the human tumor environments. *Blood* 114, 1141-1149 (2009).
12. Kryczek, I., Wei, S., Szeliga, W., Vatan, L. & Zou, W. Endogenous IL-17 contributes to reduced tumor growth and metastasis. *Blood* 114, 357-359 (2009).
13. Martin-Orozco, N., et al. T helper 17 cells promote cytotoxic T cell activation in tumor immunity. *Immunity* 31, 787-798 (2009).
14. Muranski, P., et al. Tumor-specific Th17-polarized cells eradicate large established melanoma. *Blood* 112, 362-373 (2008).
15. Ivanov, I I, Zhou, L. & Littman, D. R. Transcriptional regulation of Th17 cell differentiation. *Semin Immunol* 19, 409-417 (2007).
16. Jetten, A. M. & Joo, J. H. Retinoid-related Orphan Receptors (RORs): Roles in Cellular Differentiation and Development. *Adv Dev Biol* 16, 313-355 (2006).
17. Yang, X. O., et al. T helper 17 lineage differentiation is programmed by orphan nuclear receptors ROR alpha and ROR gamma. *Immunity* 28, 29-39 (2008).
18. Tilley, S. L., et al. Retinoid-related orphan receptor gamma controls immunoglobulin production and Th1/Th2 cytokine balance in the adaptive immune response to allergen. *J Immunol* 178, 3208-3218 (2007).
19. Kurebayashi, S., et al. Retinoid-related orphan receptor gamma (RORgamma) is essential for lymphoid organogenesis and controls apoptosis during thymopoiesis. *Proc Natl Acad Sci USA* 97, 10132-10137 (2000).
20. Elyaman, W., et al. IL-9 induces differentiation of TH17 cells and enhances function of FoxP3+ natural regulatory T cells. *Proc Natl Acad Sci USA* 106, 12885-12890 (2009).
21. Schmitt, E., et al. IL-9 production of naive CD4+ T cells depends on IL-2, is synergistically enhanced by a com- 21. bination of TGF-beta and IL-4, and is inhibited by IFN-gamma. *J Immunol* 153, 3989-3996 (1994).
22. Angkasekwinai, P., Chang, S. H., Thapa, M., Watarai, H. & Dong, C. Regulation of IL-9 expression by IL-25 signaling. *Nat Immunol* 11, 250-256 (2010).
23. Wong, M. T., et al. Regulation of human Th9 differentiation by type I interferons and IL-21. *Immunol Cell Biol* 88, 624-631 (2010).
24. Dardalhon, V., et al. IL-4 inhibits TGF-beta-induced Foxp3+ T cells and, together with TGF-beta, generates IL-9+ IL-10+ Foxp3(-) effector T cells. *Nat Immunol* 9, 1347-1355 (2008).
25. Hung, K., et al. The central role of CD4(+) T cells in the antitumor immune response. *J Exp Med* 188, 2357-2368 (1998).
26. Knoops, L. & Renauld, J. C. IL-9 and its receptor: from signal transduction to tumorigenesis. *Growth Factors* 22, 207-215 (2004).
27. Oldford, S. A., et al. A critical role for mast cells and mast cell-derived IL-6 in TLR2-mediated inhibition of tumor growth. *J Immunol* 185, 7067-7076 (2010).
28. Yang, X. R., et al. Identification of modifier genes for cutaneous malignant melanoma in melanoma-prone families with and without CDKN2A mutations. *Int J Cancer* 125, 2912-2917 (2009).
29. Smith, S. E., Hoelzinger, D. B., Dominguez, A. L., Van Snick, J. & Lustgarten, J. Signals through 4-1BB inhibit T regulatory cells by blocking IL-9 production enhancing antitumor responses. *Cancer Immunol Immunother* 60, 1775-1787 (2011).
30. Atkins, M. B., Kunkel, L., Sznol, M. & Rosenberg, S. A. High-dose recombinant interleukin-2 therapy in patients with metastatic melanoma: long-term survival update. *Cancer J Sci Am* 6 Suppl 1, S11-14 (2000).
31. Dougan, M. & Dranoff, G. Immune therapy for cancer. *Annu Rev Immunol* 27, 83-117 (2009).
32. Ma, H. L., et al. IL-21 activates both innate and adaptive immunity to generate potent antitumor responses that require perforin but are independent of IFN-gamma. *J Immunol* 171, 608-615 (2003).
33. Steenwinckel, V., et al. IL-13 mediates in vivo IL-9 activities on lung epithelial cells but not on hematopoietic cells. *J Immunol* 178, 3244-3251 (2007).
34. Awasthi, A., et al. Cutting edge: IL-23 receptor gfp reporter mice reveal distinct populations of IL-17-producing cells. *J Immunol* 182, 5904-5908 (2009).
35. Purwar, R., et al. Resident memory T cells (T(RM)) are abundant in human lung: diversity, function, and antigen specificity. *PLoS One* 6, e16245 (2011).
36. Clark, R. A., et al. A novel method for the isolation of skin resident T cells from normal and diseased human skin. *J Invest Dermatol* 126, 1059-1070 (2006).
37. O'Leary, F. M., et al. Injury-induced GR-1+ macrophage expansion and activation occurs independently of CD4 T-cell influence. *Shock* 36, 162-169 (2011).

SEQUENCES

Human IL-9 mRNA sequence NCBI Ref Seq: NM_000590

SEQ ID NO: 1

```
  1 ccgctgtcaa gatgcttctg gccatggtcc ttacctctgc cctgctcctg tgctccgtgg
 61 caggccaggg gtgtccaacc ttggcgggga tcctggacat caacttcctc atcaacaaga
121 tgcaggaaga tccagcttcc aagtgccact gcagtgctaa tgtgaccagt tgtctctgtt
181 tgggcattcc ctctgacaac tgcaccagac catgcttcag tgagagactg tctcagatga
241 ccaataccac catgcaaaca agatacccac tgattttcag tcgggtgaaa aaatcagttg
301 aagtactaaa gaacaacaag tgtccatatt tttcctgtga acagccatgc aaccaaacca
361 cggcaggcaa cgcgctgaca tttctgaaga gtcttctgga aattttccag aaagaaaaga
421 tgagagggat gagaggcaag atatgaagat gaaatattat ttatcctatt tattaaattt
481 aaaaagcttt ctctttaagt tgctacaatt taaaaatcaa gtaagctact ctaaatcagt
541 atcagttgtg attatttgtt taacattgta tgtctttatt ttgaaataaa t
```

Human IL-9 amino acid sequence NCBI Ref No: NP_000581

SEQ ID NO: 2

```
  1 mllamvltsa lllcsvagqg cptlagildi nflinkmqed paskchcsan vtsclclgip
 61 sdnctrpcfs erlsqmtntt mqtryplifs rvkksvevlk nnkcpyfsce qpcnqttagn
121 altflkslle ifqkekmrgm rgki
```

Human IL-9Ra mRNA sequence NCBI Ref No: NM_002186

SEQ ID NO: 3

```
    1 agcagctctg taatgcgctt gtggtttcag atgtgggcgg cctgtgtgaa cctgtcgtgc
   61 aaagctcacg tcaccaactg ctgcagttat ctcctgaatc aggctgaggg tctttgctgt
  121 gcacccagag atagttgggt gacaaatcac ctccaggttg gggatgcctc agacttgtga
  181 tgggactggg cagatgcatc tgggaaggct ggaccttgga gagtgaggcc ctgaggcgag
  241 acatgggcac ctggctcctg gcctgcatct gcatctgcac ctgtgtctgc ttgggagtct
  301 ctgtcacagg ggaaggacaa gggccaaggt ctagaacctt cacctgcctc accaacaaca
  361 ttctcaggat cgattgccac tggtctgccc cagagctggg acagggctcc agccccctggc
  421 tcctcttcac cagcaaccag gctcctggcg gcacacataa gtgcatcttg cggggcagtg
  481 agtgcaccgt cgtgctgcca cctgaggcag tgctcgtgcc atctgacaat tcaccatca
  541 ctttccacca ctgcatgtct gggagggagc aggtcagcct ggtggacccg gagtacctgc
  601 cccggagaca cgttaagctg gacccgccct ctgacttgca gagcaacatc agttctggcc
  661 actgcatcct gacctggagc atcagtcctg ccttggagcc aatgaccaca cttctcagct
  721 atgagctggc cttcaagaag caggaagagg cctgggagca ggcccagcac agggatcaca
  781 ttgtcggggt gacctggctt atacttgaag cctttgagct ggaccctggc tttatccatg
  841 aggccaggct gcgtgtccag atggccacac tggaggatga tgtggtagag gaggagcgtt
  901 atacaggcca gtggagtgag tggagccagc ctgtgtgctt ccaggctccc cagagacaag
  961 gccctctgat cccacccctgg gggtggccag gcaaccaccct tgttgctgtg tccatctttc
 1021 tcctgctgac tggcccgacc tacctcctgt tcaagctgtc gcccaggdtg aagagaatct
 1081 tctaccagaa cgtgccctct ccagcgatgt tcttccagcc cctctacagt gtacacaatg
 1141 ggaacttcca gacttggatg ggggcccacg gggccggtgt gctgttgagc caggactgtg
 1201 ctggcacccc acagggagcc ttggagccct gcgtccagga ggccactgca ctgctcactt
 1261 gtggcccagc gcgtccttgg aaatctgtgg ccctggagga ggaacaggag ggccctggga
```

-continued

| | SEQUENCES |
|---|---|

```
1321 ccaggctccc ggggaacctg agctcagagg atgtgctgcc agcagggtgt acggagtgga
1381 gggtacagac gcttgcctat ctgccacagg aggactgggc ccccacgtcc ctgactaggc
1441 cggctccccc agactcagag ggcagcagga gcagcagcag cagcagcagc agcaacaaca
1501 acaactactg tgccttgggc tgctatgggg gatggcacct ctcagccctc ccaggaaaca
1561 cacagagctc tgggcccatc ccagccctgg cctgtgcct ttcttgtgac catcagggcc
1621 tggagaccca gcaaggagtt gcctgggtgc tggctggtca ctgccagagg cctgggctgc
1681 atgaggacct ccagggcatg ttgctccctt ctgtcctcag caaggctcgg tcctggacat
1741 tctaggtccc tgactcgcca gatgcatcat gtccattttg ggaaaatgga ctgaagtttc
1801 tggagccctt gtctgagact gaacctcctg agaaggggcc cctagcagcg tcagaggtc
1861 ctgtctggat ggaggctgga ggctcccccc tcaaccctc tgctcagtgc ctgtggggag
1921 cagcctctac cctcagcatc ctggccacaa gttcttcctt ccattgtccc ttttctttat
1981 ccctgacctc tctgagaagt ggggtgtggt ctctcagctg ttctgccctc atacccttaa
2041 agggccagcc tgggcccagt ggacacaggt aaggccaccat gaccacctgg tgtgacctct
2101 ctgtgcctta ctgaggcacc tttctagaga ttaaagggg cttgatggct gttaaaaaaa
2161 aaaaaaaaa a
```

Human IL-9Ra amino acid sequence NCBI Ref No: NP_002177

SEQ ID NO: 4

```
  1 mglgrciweg wtlesealrr dmgtwllaci cictcvclgv svtgegqgpr srtftcltnn
 61 ilridchwsa pelgqgsspw llftsnqapg gthkcilrgs ectvvlppea vlvpsdnfti
121 tfhhcmsgre qvslvdpeyl prrhvkldpp sdlqsnissg hciltwsisp alepmttlls
181 yelafkkqee aweqaqhrdh ivgvtwlile afeldpgfih earlrvqmat leddvveeer
241 ytgqwsewsq pvcfqapqrq gplippwgwp gntivaysif llltgptyll fklsprvkri
301 fyqnvpspam ffqplysvhn gnfqtwmgah gagvllsqdc agtpqgalep cvqeatallt
361 cgparpwksv aleeqegpg trlpgnlsse dvlpagctew rvqtlaylpq edwaptsltr
421 pappdsegsr ssssssssnn nnycalgcyg gwhlsalpgn tqssgpipal acglscdhqg
481 letqqgvawv laghcqrpgl hedlqgmllp svlskarswt f
```

Human IL2RG mRNA sequence NCBI Ref No: NM_000206

SEQ ID NO: 5

```
   1 agaggaaacg tgtgggtggg gaggggtagt gggtgaggga cccaggttcc tgacacagac
  61 agactacacc cagggaatga agagcaagcg ccatgttgaa gccatcatta ccattccat
 121 ccctcttatt cctgcagctg cccctgctgg gagtgggggct gaacacgaca attctgacgt
 181 ccaatgggaa tgaagacacc acagctgatt tcttcctgac cactatgccc actgactccc
 241 tcagtgtttc cactctgccc ctcccagagg ttcagtgttt tgtgttcaat gtcgagtaca
 301 tgaattgcac ttggaacagc agctctgagc ccagcctac caacctcact ctgcattatt
 361 ggtacaagaa ctcggataat gataaatcc agaagtgcag ccactatctc ttctctgaag
 421 aaatcacttc tggctgtcag ttgcaaaaaa aggagatcca cctctaccaa acatttgttg
 481 ttcagctcca ggacccacgg gaacccagga caggccac acagatgcta aaactgcaga
 541 atctggtgat ccccctgggct ccagagaacc taacacttca caaactgagt gaatcccagc
 601 tagaactgaa ctgaacaac agattcttga accactgttt ggagcacttg gtgcagtacc
 661 ggactgactg gaccacagc tggactgaac aatcagtgga ttatagacat aagttctcct
 721 tgcctagtgt ggatgggcag aaacgctaca cgtttcgtgt tcggagccgc tttaacccac
 781 tctgtggaag tgctcagcat tggagtgaat ggagccaccc aatccactgg ggagcaata
 841 cttcaaaaga gaatccttc ctgtttgcat tggaagccgt ggttatctct gttggctcca
 901 tgggattgat tatcagcctt ctctgtgtgt atttctggct ggaacggacg atgccccgaa
 961 ttcccaccct gaagaaccta ggatcttg ttactgaata ccacgggaac ttttcggcct
1021 ggagtggtgt gtctaaggga ctggctgaga gtctgcagcc agactacagt gaacgactct
1081 gcctcgtcag tgagattccc ccaaaaggag gggcccttgg ggaggggcctccc
1141 catgcaacca gcatagcccc tactgggccc cccatgttta cccctaaag cctgaaacct
1201 gaaccccaat cctctgacag aagaacccca ggtcctgta gccctaagtg gtactaactt
1261 tccttcattc aacccacctg cgtctcatac tcacctcacc ccactgtggc tgatttggaa
1321 ttttgtgccc ccatgtaagc acccctcat ttggcattcc cacctgaa attaccctt
1381 tgccccgaac atgttttct ctccctcag tctggccctt ccttcgca ggattcttcc
1441 tccctccctc ttcccctccc tcctctttc catctaccct ccgattgtc ctgaaccgat
1501 gagaaataaa gttctgttg ataatcatca aaaaaaaaaa aaaaaaaaaa aaaaaaaaaa
```

Human IL2RG amino acid sequence NCBI Ref No: NP_000197

SEQ ID NO: 6

```
  1 mlkpslpfts llflqlpllg vglnttiltp ngnedttadf flttmptdsl systlplpev
 61 qcfvfnveym nctwnsssep qptnlfthyw yknsdndkvq kcshylfsee itsgcqlqkk
121 eihlyqtfvv qlqdpreprr qatqmlklqn lvipwapenl fthklsesql elnwnnrfln
181 hclehlvqyr tdwdhswteq svdyrhkfsl psvdgqkryt frvrsrfnpl cgsaqhwsew
241 shpihwgsnt skenpflfal eavvisvgsm gliisllcvy fwlertmpri ptlknledlv
301 teyhgnfsaw sgvskglaes lqpdyserlc lvseippkgg algegpgasp cnqhspywap
361 pcytlkpet
```

Human TH2AF1 cDNA sequence NCBI Ref No: NM_017625

SEQ ID NO: 7

```
  1 aggagcgttt ttggagaaag ctgcactctg ttgagctcca gggcgcagtg gagggaggga
 61 gtgaaggagc tctctgtacc caaggaaagt gcagctgaga ctcagacaag attacaatga
121 accaactcag cttcctgctg tttctcatag cgaccaccag aggatggagt acagatgagg
181 ctaatactta cttcaaggaa tggacctgtt cttcgtctcc atctctgccc agaagctgca
241 aggaaatcaa agacgaatgt cctagtcat ttgatggcct gtattttctc cgcactgaga
301 atggtgttat ctaccagacc ttctgtgaca tgacctctgg gggtggcggc tgggccctgg
361 tggcagcgt gcacgagaat gacatgcgtg gaagtgcac ggtgggcgat cgctggtcca
421 gtcagcaggg cagcaaagca gtctacccag agggggacgg caactgggcc aactacaaca
```

-continued

| SEQUENCES |
|---|

```
 481 cctttggatc tgcagaggcg gccacgagcg atgactacaa gaaccctggc tactacgaca
 541 tccaggccaa ggacctgggc atctggcacg tgcccaataa gtcccccatg cagcactgga
 601 gaaacagctc cctgctgagg taccgcacgg acactggctt cctccagaca ctgggacata
 661 atctgtttgg catctaccag aaatatccag tgaaatatgg agaaggaaag tgttggactg
 721 acaacggccc ggtgatccct gtggtctatg attttggcga cgcccagaaa acagcatctt
 781 attactcacc ctatggccag cgggaattca ctgcgggatt tgttcagttc agggtattta
 841 ataacgagag agcagccaac gccttgtgtg ctggaatgag ggtcaccgga tgtaacactg
 901 agcaccactg cattggtgga ggaggatact tccagagcag cagtccccag cagtgtggag
 961 attttttctg ttttgattgg agtggatatg gaactcatgt tggttacagc agcagccgtg
1021 agataactga ggcagctgtg cttctattct atcgttgaga gttttgtggg agggaaccca
1081 gacctctcct cccaaccatg agatcccaag gatggagaac aacttaccca gtagctagaa
1141 tgttaatggc agaagagaaa acaataaaatc atattgactc aaaaaaaaaa aaaaaaaaaa
1201 aaaaaaaa
```

Human TH2AF1 amino acid sequence NCBI Ref No: NP_060095

SEQ ID NO: 8
```
   1 mnqlsfllfl iattrgwstd eantyfkewt cssspslprs ckeikdecps afdglyflrt
  61 engviyqtfc dmtsggggwt lvasvhendm rgkctvgdrw ssqqgskavy pegdgnwany
 121 ntfgsaeaat sddyknpgyy diqakdlgiw hvpnkspmqh wrnssllryr tdtgflqtlg
 181 hnlfgiyqky pvkygegkcw tdngpvipvv ydfgdaqkta syyspygqre ftagfvqfry
 241 fnneraanal cagmrvtgcn tehhcigggg yfpeaspqqc gdfsgfdwsg ygthvgyssss
 301 reiteaavll fyr
```

Human CLCA2 cDNA sequence NCBI Ref No: NM_006536

SEQ ID NO: 9
```
   1 tcccagatgg atccacccca gacttttcaa agaagacacc tccttcatct tgtgttctaa
  61 aaccttgcaa gttcaggaag aaaccatctg catccatatt gaaaacctga cacaatgtat
 121 gcagcaggct cagtgtgagt gaactggagg ctttctctaca acatgaccca aaggagcatt
 181 gcaggtccta tttgcaacct gaagtttgtg actctcctgg ttgccttaag ttcagaactc
 241 ccattcctgg gagctggagt acagcttcaa gacaatgggt ataatggatt gtcattgca
 301 attaatcctc aggtacctga gaatcagaac ctcatctcaa acattaagga aatgataact
 361 gaagcttcat tttacctatt taatgctacc aagagaagag tattttcag aaatataaag
 421 atttaatac ctgccacatg gaaagctaat aataacagca aaataaaaca agaatcatat
 481 gaaaaggcaa atgtcatagt gactgactgg tatgggcac atggagatga tccatacacc
 541 ctacaataca gagggtgtgg aaaagaggga aaatacattc atttcacacc taatttccta
 601 ctgaatgata acttaacagc tggctacgga tcacgaggcc gagtgtttgt ccatgaatgg
 661 gcccacctcc gttggggtgt gttcgatgag tataacaatg acaaaccttt ctacatcaaat
 721 gggcaaaatc aaattaaagt gacaaggtgt tcatctgaca tcacaggcat ttttgtgtgt
 781 gaaaaaggtc cttgccccca agaaaactgt attattagta gcttttttaa agaaggatgc
 841 acctttatct acaatagcac ccaaaatgca actgcatcaa taatgttcat gcaaagttta
 901 tcttctgtgg ttgaattttg taatgcaagt acccacaacc aagaagcacc aaacctacag
 961 aaccagatgt gcagcctcag aagtgcatgg gatgtaatca cagactctgc tgactttcac
1021 cacagctttc ccatgaatgg gactgagctt ccacctcctc ccacattctc gcttgtacag
1081 gctggtgaca agtggtctg tttagtgctg gatgtgtcca gcaagatggc agaggctgac
1141 agactccttc aactacaaca agccgcagaa ttttatttga tgcagattgt tgaaattcat
1201 accttcgtgg gcattgccag tttcgacagc aaaggagaga tcagagccca gctacaccaa
1261 attaacagca atgatgatcg aaagttgctg gtttcatatc tgcccaccac tgtatcagct
1321 aaaacagaca tcagcatttg ttcagggctt aagaaaggat tgaggtggt tgaaaaactg
1381 aatggaaaag cttatggctc tgtgatgata ttagtgacca gcggagatga taagcttctt
1441 ggcaattgct tacccactgt gctcagcagt ggttcaacaa ttcactccat tgccctgggt
1501 tcatctgcag ccccaaatct ggaggaatta tcacgtctta caggaggttt aaagttcttt
1561 gttccagata tatcaaactc caatagcatg attgatgctt tcagtagaat ttcctctgga
1621 actgaagaca ttttcagca acatattcag cttgaaagta caggtgaaaa tgtcaaacct
1681 caccatcaat tgaaaaacac agtgactgtg gataatactg tgggcaacga cactctatgtttt
1741 ctagttacgt ggcaggccag tggtcctcct gagattatat tatttgatcc tgatggacga
1801 aaatactaca caaataattt tatcaccaat ctaactttc ggacagctag tctttggatt
1861 ccaggaacag ctaagcctgg gcactggact tacaccctga caataccca tcattctctg
1921 caagccctga agtgacagt gacctctcgc gcctccaact cagctgtgcc cccagccact
1981 gtggaagcct ttgtgaaaag agacagcctc catttttcctc atcctgtgat gatttatgcc
2041 aatgtgaaac agggattta tcccattctt aatgccactg tcactgccac agttgagcca
2101 gagactggag atcctgttac gctgagactc cttgatgatg gagcaggtgc tgatgttata
2161 aaaaatgatg gaatttactc gaggtatttt ttctcctttg ctgcaaatg tagatatagc
2221 ttgaaagtgc atgtcaatca ctctcccagc ataagcaccc cagcccactc tattccaggg
2281 agtcatgcta tgtatgtacc aggttacaca gcaaacggta atattcagat gaatgctcca
2341 aggaaatcag taggcagaaa tgaggaggag cgaaagtggg gctttagccg agtcagctca
2401 ggaggctcct tttcagtgct gggagttcca gctggcccc acctgatgt gtttccacca
2461 tgcaaaatta ttgacctgga agctgtaaaa gtagaagagg aattgaccct atcttggaca
2521 gcacctggag aagactttga tcagggccag gctacaagct atgaaatnag aatgagtaaa
2581 agtctacaga atatccaaga tgactttaac aatgctattt tagtaaatac atcaaagcga
2641 aatcctcagc aagctggcat cagggagata tttacgttct caccccaaat tccacgaat
2701 ggacctgaac atcagccaaa tggagaaaca catgaaagcc acagaattta tgttgcaata
2761 cgagcaatgg ataggaactc cttacagtct gctgtatcta acattgccca ggcgcctctg
2821 tttattcccc ccaattctga tcctgtacct gccagagatt atcttatatt gaaaggagtt
2881 tttaacagcaa tgggtttgat aggaatcatt gccttatta tagttgtgac acatcatact
2941 ttaagcagga aaagagagc agacaagaaa gagaatggaa caaaattatt ataaataaat
3001 atccaaagtg tcttccttct tagatataag acccatggcc ttcgactaca aaaacatact
3061 aacaaagtca aattaacatc aaaactgtat taaaatgcat tgagttttg tacaatacag
```

-continued

| SEQUENCES |
|---|

```
3121 ataagatttt tacatggtag atcaacaaat tcttttgggg ggtagattag aaaacccttta
3181 cactttggct atgaacaaat aataaaaatt attcttaaa gtaatgtctt taaaggcaaa
3241 gggaagggta aagtcggacc agtgtcaagg aaagtttgtt ttattgaggt ggaaaaatag
3301 ccccaagcag agaaaaggag ggtaggtctg cattataact gtctgtgtga agcaatcatt
3361 tagttacttt gattaatttt tcttttctcc ttatctgtgc agaacaggtt gcttgtttac
3421 aactgaagat catgctatat tttatatatg aagcccctaa tgcaaagctc tttacctctt
3481 gctattttgt tatatatatt acagatgaaa tctcactgct aatgctcaga gatcttttt
3541 cactgtaaga ggtaacctt aacaatatgg gtattacctt tgtctcttca taccggtttt
3601 atgacaaagg tctattgaat ttatttgttt gtaagtttct actcccatca aagcagcttt
3661 ctaagttatt gccttggtta ttatggatga tagttatagc ccttataatg ccttaactaa
3721 ggaagaaaag atgttattct gagtttgttt taatacatat atgaacatat agtttgtattc
3781 aattaaacca aagaagaggt cagcagggag atactaacct ttggaaatga ttagctggct
3841 ctgtttttg gttaaataag agtctttaat cctttctcca tcaagagtta cttaccaagg
3901 gcaggggaag ggggatatag aggtcacaag gaaataaaaa tcatctttca tctttaatttt
3961 tactccttcc tcttattttt ttaaaagatt atcgaacaat aaaatcattt gcctttttaa
4021 ttaaaaaaaa aaaaaaaaaa aaa
```

Human CLCA2 amino acid sequence NCBI Ref No: NP_006527
SEQ ID NO: 10

```
  1 mtqrsiagpi cnlkfvtllv alsselpflg agvqlqdngy nglliainpq vpenqnlisn
 61 ikemiteasf ylfnatkrry ffrnikilip atwkannnsk ikqesyekan vivtdwygah
121 gddpytlqyr gcgkegkyih ftpnflldn ltagygsrgr vfvhewahlr wgvfdeynnd
181 kpfyingqnq ikvtrcssdi tgifvcekgp cpqenciisk lfkegctfiy nstqnatasi
241 mfmqslssvv efcnasthnq eapnlqnqmc slrsawdvit dsadfhhsfp mngtelpppp
301 tfslvqagdk vvclvldvss kmaeadrllq lqqaaefylm qiveihtfvg iasfdskgei
361 raqlhqinsn ddrkllvsyl pttvsaktdi sicsglkkgf evveklngka ygsvmilvts
421 gddkllgncl ptvlssgsti hsialgssaa pnleelsrlt gglldfvpdi snsnsmidaf
481 srissgtgdi fqqhiqlest genvkphhql kntvtvdntv gndtmflvtw qasgppeiil
541 fdpdgrkyyt nnfitnltfr taslwipgta kpghwtytln nthhslqalk vtvtsrasns
601 avppatveaf verdslhfph pymiyanvkq gfypilnatv tatvepetgd pvtlrllddg
661 agadvikndg iysryffsfa angryslkvh vnhspsistp ahsipgsham yvpgytangn
721 iqmnaprksv grneeerkwg fsrvssggsf svlgvpagph pdvfppckii dleavkveee
781 ltlswtapge dfdqgqatsy eirmskslqn iqddfnnail vntskrnpqq agireiftfs
841 pqistngpeh qpngethesh riyvairamd rnslqsavsn iaqaplfipp nsdpvpardy
901 lilkgvltam gligiiclii vvthhtlsrk kradkkengt kll
```

Human RORγ cDNA sequence NCBI Ref No: NM_001001523
SEQ ID NO: 11

```
   1 agagagctag gtgcagagct tcaggctgag gcgctgctga gagggcctcg cccgcctct
  61 gccgccagct gcaccccact cctggaccac cccctgctga aaggacagg gagccaaggc
 121 cggcagagcc aagctcagt catgagaaca caaattgaag tgatcccttg caaaatctgt
 181 ggggacaagt cgtctgggat ccactacggg gttatacct gtgaggggtg caagggcttc
 241 ttccgccgga gccagcgctg taacgcggcc tactcctgca cccgtcagca gaactgcccc
 301 atcgaccgca ccagccgaaa ccgatgccag cactgccgcc tgcagaaatg cctggctctg
 361 ggcatgtccc gagatgctgt caagttcggc cgcatgtcca agaagcagag ggacagcctg
 421 catgcagaag tgcagaaaca gctgcagcag cggcaacagc agcaacagga accagtggtc
 481 aagacccctc cagcagggc caaggagca gataccctca cctacacctt ggggctccca
 541 gacgggcagc tgccctggg ctcctcgcct gacctgcctg aggcttctgc ctgtcccct
 601 ggcctcctga aagcctcagg ctctgggcc tcatattcca acaacttggc caggcagggg
 661 ctcaatggg cctcatgcca ccttgaatac agccctgagc ggggcaaggc tgagggcaga
 721 gagagcttct atagcacagg cagccagctg accctgacc gatgtggact tcgttttgag
 781 gaacacaggc atcctgggct tggggaactg gacagggcc agacagcta cggcagcccc
 841 agtttccgca gcacaccgga gcaccctat gcctccctga cagagataga gcacctggtg
 901 cagagcgtct gcaagtccta caggggaaca tgccagtgc ggctggagga cctgctgcgg
 961 cagcgctcca acatcttctc ccgggaggaa gtgactggct accagaggaa gtccatgtgg
1021 gagatgtggg aacggtgtgc ccaccacctc accgaggcca ttcagtacgt ggtggagttc
1081 gccaagagggc tctcaggctt tatggagctc tgccagaatg accagattgt gcttctcaaa
1141 gcaggagcga tggaagtggt gctggttagg atgtgccggg cctacaatgc tgacaaccgc
1201 acggtctttt tgaaggcaa atacggtggc atggagctgt ccgagcctt gggctgcagc
1261 gagctcatca gctccatctt tgacttctcc cactccctaa gtgccttgca cttttccgag
1321 gatgagattg ccctctacac agcccttgtt ctcatcaatg cccatcggcc agggctccaa
1381 gagaaaagga agtagaaca agctcagtac aatctggagc tggccttca tcatcatctc
1441 tgcaagactc atcgccaaag catcctggca aagctgccca ccaaggggaa gcttcggagc
1501 ctgtgtagcc agcatgtgga aagctgcag atcttccagc acctccaccc catcgtggtc
1561 caagccgctt ccctccact ctacaaggag ctcttcagca ctgaaaccga gtcacctgtg
1621 gggctgtcca agtgactgg aagagggact ccttgcctct ccctatggcc tgctggccca
1681 cctccctgga ccccgttcca ccctcaccct ttcctttcc catgaaccct ggagggtggt
1741 ccccaccagc tctttggaag tgagcagatg ctgcggctgg cttctgtca gcaggccggc
1801 ctggcagtgg gacaatcgcc agagggtggg gctggcagaa caccatctcc agcctcagct
1861 ttgacctgtc tcatttccca tattccttca cacccagctt ctgaaggca tggggtggc
1921 gggatttaag gacttctggg ggaccaagac atcctcaaga aaacaggggc atccagggct
1981 ccctgatga atagaatgca attcattcag aagctcagga gctaagaata agcctttgaa
2041 atacctcatt gcatttccct ttgggcttcg cgttggggag atggatcaag ctcagagact
2101 ggcagtgaga gcccagaagg acctgtataa atgaatctg gagctttaca tttctgcct
2161 ctgccttcct cccagctcag caaggaagta tttgggcacc ctaccctta cctgggtct
2221 aaccaaaaat ggatgggatg aggatgagag gctggagata attgttttat gggatttggg
2281 tgtgggacta gggtacaatg aaggccaaga gcatctcaga catagagtta aaactcaaac
```

| SEQUENCES |
|---|
| 2341 ctcttatgtg cactttaaag atagacttta gggctggca caaatctgat cagagacaca |
| 2401 tatccataca caggtgaaac acatacagac tcaacagcaa tcatgcagtt ccagagacac |
| 2461 atgaacctga cacaatctct cttatccttg aggccacagc ttggaggagc ctagaggcct |
| 2521 caggggaaag tcccaatcct gagggaccct cccaaacatt tccatggtgc tccagtccac |
| 2581 tgatcttggg tctggggtga tccaaatacc accccagctc cagctgtctt ctaccactag |
| 2641 aagacccaag agaagcagaa gtcgctcgca ctggtcagtc ggaaggcaag atcagatcct |
| 2701 ggaggacttt cctggcctgc cgccagccc tgctcttgtt gtggagaagg aagcagatgt |
| 2761 gatcacatca cccgtcatt gggcaccgct gactccagca tggaggacac cagggagcag |
| 2821 ggcctgggcc tgtttcccca gctgtgatct tgcccagaac ctctcttggc ttcataaaca |
| 2881 gctgtgaacc ctcccctgag ggattaacag caatgatggg cagtcgtgga gttggggggg |
| 2941 ttggggtgg gattgtgtcc tctaagggga cgggttcatc tgagtaaaca taaaccccaa |
| 3001 cttgtgccat tctttataaa atgattttaa aggcaaaaaa aaaaaaaaaa aaaa |

Human RORγ amino acid sequence NCBI Ref No: NP_001001523
SEQ ID NO: 12

|   |   |   |   |   |   |
|---|---|---|---|---|---|
| 1 | mrtqievipc | kicgdkssgi | hygvitcegc | kgffrrsqrc | naaysctrqq ncpidrtsrn |
| 61 | rcqhcrlqkc | lalgmsrdav | kfgrmskkqr | dslhaevqkq | lqqrqqqqqe pvvktppaga |
| 121 | qgadtltytl | glpdgqlplg | sspdlpeasa | cppgllkasg | sgpsysnnla kaglngasch |
| 181 | leyspergka | egresfystg | sqltpdrcgl | rfeehrhpgl | gelgqgpdsy gspsfrstpe |
| 241 | apyaslteie | hlvqsvcksy | retcqlrled | llrqrsnifs | reevtgyqrk smwemwerca |
| 301 | hhlteaiqyv | vefakrlsgf | melcqndqiv | llkagamevv | lvrmcrayna dnrtvffegk |
| 361 | yggmelfral | gcselissif | dfshslsalh | fsedeialyt | alvlinahrp glqekrkveq |
| 421 | lqynlelafh | hhlckthrqs | ilaklppkgk | lrslcsqhve | rlqifqhlhp ivvqaafppl |
| 481 | ykelfstete | spvglsk |  |  |  |

Human RORγt cDNA sequence NCBI Ref No: NM_005060
SEQ ID NO: 13

| 1 | gccaggtgct | cccgccttcc | accctccgcc | ctcctccctc | ccctgggccc tgctccctgc |
|---|---|---|---|---|---|
| 61 | cctcctgggc | agccagggca | gccaggacgg | caccaaggga | gctgccccat ggacagggcc |
| 121 | ccacagagac | agcaccgagc | ctcacgggag | ctgctggctg | caaagaagac ccacacctca |
| 181 | caaattgaag | tgatcccttg | caaaatctgt | ggggacaagt | cgtctgggat ccactacggg |
| 241 | gttatcacct | gtgaggggtg | caagggcttc | ttccgccgga | gccagcgctg taacgcggcc |
| 301 | tactcctgca | cccgtcagca | gaactgccc | atcgaccgca | ccagccgaaa ccgatgccag |
| 361 | cactgccgcc | tgcagaaatg | cctggcgctg | ggcatgtccc | gagatgctgt caagttcggc |
| 421 | cgcatgtcca | agaagcagag | ggacagcctg | catgcagaag | tgcagaaaca gctgcagcag |
| 481 | cggcaacagc | agcaacagga | accagtggtc | aagacccctc | cagcagggc caaggagca |
| 541 | gataccctca | cctacacctt | gggctccca | gacgggcagc | tgcccctggg ctcctcgcct |
| 601 | gacctgcctg | aggcttctgc | ctgtcccct | ggcctcctga | agcctcagg ctctgggccc |
| 661 | tcatattcca | caacttggc | caaggcaggg | ctcaatgggg | cctcatgcca ccttgaatac |
| 721 | agccctgagc | ggggcaaggc | tgagggcaga | gagagcttct | atagcacagg cagccagctg |
| 781 | acccctgacc | gatgtggact | tcgtttgag | gaacacaggc | atcctgggct tggggagctg |
| 841 | ggacagggcc | cagacagcta | cggcagcccc | agtttccgca | gcaccgga ggcaccctat |
| 901 | gcctccctga | cagagataga | gcaccggtg | cagagcgtct | gcaagtccta cagggagaca |
| 961 | tgccagctgc | ggctggagga | cctgctgcgg | cagcgctcca | acatcttctc ccgggaggaa |
| 1021 | gtgactggct | accagaggaa | gtccatgtgg | gagatgtggg | aacggtgtgc ccaccacctc |
| 1081 | accgaggcca | ttcagtacgt | ggtggagttc | gccaagagc | tctcaggctt tatggagctc |
| 1141 | tgccagaatg | accagattgt | gcttctcaaa | gcaggagcaa | tggaagtggt gctggttagg |
| 1201 | atgtgccggg | cctacaatgc | tgacaaccgc | acggtctttt | ttgaaggcaa atacggtggc |
| 1261 | atggagctgt | tccgagcctt | gggctgcagc | gagctcatca | gcttccatct tgacttctcc |
| 1321 | cactccctaa | gtgccttgca | ctttcccgag | gatgagattg | ccctacac agcccttgtt |
| 1381 | ctcatcaatg | cccatcggcc | agggctccaa | gagaaaagga | aagtagaaca gctgcagtac |
| 1441 | aatctggagc | tggccttca | tcatcatctc | tgcaagactc | atcgcaaag catcctggca |
| 1501 | aagctgccac | ccaaggggaa | gcttcggagc | ctgtgtagcc | agcatgtgga aaggctgcag |
| 1561 | atcttccagc | acctccaccc | catcgtggtc | caagccgctt | tccctccact ctacaaggag |
| 1621 | ctcttcagca | ctgaaaccga | gtcacctgtg | gggctgtcca | agtgacctgg aagaggact |
| 1681 | ccttgcctct | ccctatggcc | tgctggccca | cctccctgga | cccgttcca ccctcaccct |
| 1741 | tttcctttcc | catgaaccct | ggagggtggt | cccaccagc tctttggaag tgagcagatg |
| 1801 | ctgcggctgg | cttctgtca | gcaggccggc | ctggcagtgg | gacaatcgcc agaggtgg |
| 1861 | gctggcagaa | caccatctcc | agcctcagct | ttgacctgtc | tcatttccca tattccttca |
| 1921 | cacccagctt | ctgaaggca | tggggtggct | gggatttaag | gacttctggg ggaccaagac |
| 1981 | atcctcaaga | aaacaggggc | atccaggct | ccctggatga | atagaatgca attcattcag |
| 2041 | aagctcagaa | gctaagaata | agcctttgaa | ataacctcatt | gcatttccct ttgggcttcg |
| 2101 | gcttggggag | atggatcaag | ctcagagact | ggcagtgaga | gcccagaagg acctgtataa |
| 2161 | aatgaatctg | gagctttaca | ttttctgcct | ctgcttcct | cccagctcag caaggaagta |
| 2221 | tttgggcacc | ctaccttta | cctggggtct | aaccaaaaat | ggatgggatg aggatgagag |
| 2281 | gctggagata | attgttttat | ggggatttggg | tgtgggacta | gggtacaatg aaggccaaga |
| 2341 | gcatctcaga | cataagttta | aaactcaaac | ctcttatgtg | cactttaaag atagacttta |
| 2401 | ggggctggca | caaatctgat | cagagacaca | tatccataca | caggtgaaac acatacagac |
| 2461 | tcaacagcaa | tcatgcagtt | ccagagacac | atgaacctga | cacaatctct cttatccttg |
| 2521 | aggccacagc | ttggaggagc | ctagaggcct | caggggaaag | tcccaatcct gagggaccct |
| 2581 | cccaaacatt | tccatggtgc | tccagtccac | tgatcttggg | tctggggtga tccaaatacc |
| 2641 | accccagctc | cagctgtctt | ctaccactag | aagacccaag | agaagcagaa gtcgctcgca |
| 2701 | ctggtcagtc | ggaaggcaag | atcagatcct | ggaggacttt | cctggcctgc cgccagccc |
| 2761 | tgctcttgtt | gtggagaagg | aagcagatgt | gatcacatca | cccgtcatt gggcaccgct |
| 2821 | gactccagca | tggaggacac | cagggagcag | ggcctgggcc | tgtttcccca gctgtgatct |
| 2881 | tgcccagaac | ctctcttggc | ttcataaaca | gctgtgaacc | ctcccctgag ggattaacag |
| 2941 | caatgatggg | cagtcgtgga | gttgggggg | ttggggtgg | gattgtgtcc tctaagggga |

SEQUENCES

```
3001 cgggttcatc tgagtaaaca taaaccccaa cttgtgccat tctttataaa atgattttaa
3061 aggcaaaaaa aaaaaaaaaa aaaa
```

Human RORγt amino acid sequence NCBI Ref No: NM_005051
SEQ ID NO: 14

```
  1 mdrapqrqhr asrellaakk thtsqievip ckicgdkssg ihygvitceg ckgffrrsqr
 61 cnaaysctrq qncpidrtsr nrcqhcrlqk clalgmsrda vkfgrmskkq rdslhaevqk
121 qlqqrqqqqq epvvktppag aqgadtltyt lglpdgqlpl gsspdlpeas acppgllkas
181 gsgpsysnnl akaglngasc hleyspergk aegresfyst gsqltpdrcg lrfeehrhpg
241 lgelgqgpds ygspsfrstp eapyasltei ehlvqsvcks yretcqlrle dllrqrsnif
301 sreevtgyqr ksmwemwerc ahhlteaiqy vvefakrlsg fmelcqndqi vllkagamev
361 vlvrmcrayn adnrtvffeg kyggmelfra lgcselissi fdfshslsal hfsedeialy
421 talvlinahr pglqekrkve qlqynlelaf hhhlckthrq silaklppkg klrslcsqhv
481 erlqifqhlh pivvqaafpp lykelfstet espvglsk
```

KP-20 amino acid seqence
SEQ ID NO: 15

FSRVKKSVEVLKNNKAPYFS

KP-89 amino acid sequence
SEQ ID NO: 16

SRRASVGFSRVKKSVEVLKNNKAPYFS

TAX amino acid sequence
SEQ ID NO 17

```
  1 hfpgfgqsll fgypvyvfgd cvqgdwcpis gglcsarlhr hallatcpeh qitwdpidgr
 61 vigsalqfli prlpsfptqr tsktlkvltp pithttpnip psflqamrky spfrngymep
121 tlgqhlptls fpdpglrpqn lytlwggsvv cmylyqlspp itwpllphvi fchpgqlgaf
181 ltnvpykrie ellykisltt galiilpedc lpttlfqpar apvtltawqn gllpfhstlt
241 tpgliwtftd gtpmisgpcp kdgqpslvlq sssfifhkfq tkayhpsfll shgliqyssf
301 hslhllfeey tnipisllfn ekeaddndhe pqispgglep psekhfrete v
```

---

The invention claimed is:

1. A method for treating melanoma in a subject comprising administering to a subject in need thereof a therapeutically effective amount of an agonist of an interleukin-9 receptor (IL-9R), wherein the agonist of IL9-R comprises a population of Th9 cells or an IL-9 polypeptide, wherein the IL-9 polypeptide is selected from the group consisting of: SEQ ID NO: 2, amino acids 19-144 of SEQ ID NO: 2, SEQ ID NO: 15 and SEQ ID NO: 16.

2. The method of claim 1, wherein the agonist further comprises a pharmaceutically acceptable carrier.

3. The method of claim 1, wherein the subject is human.

4. The method of claim 1, wherein the agonist is administered by a route selected from the group consisting of: intratumor, adoptive cell transfer, and parenteral administration.

* * * * *

UNITED STATES PATENT AND TRADEMARK OFFICE
CERTIFICATE OF CORRECTION

PATENT NO. : 9,629,910 B2
APPLICATION NO. : 14/004438
DATED : April 25, 2017
INVENTOR(S) : Kupper et al.

It is certified that error appears in the above-identified patent and that said Letters Patent is hereby corrected as shown below:

In Column 1 please insert the following section header and paragraph at Line 14:
--STATEMENT REGARDING FEDERALLY-SPONSORED RESEARCH
This invention was made with Government support under Grant Numbers AI041707 awarded by the National Institutes of Health. The Government has certain rights in this invention.--

Signed and Sealed this
Tenth Day of July, 2018

Andrei Iancu
*Director of the United States Patent and Trademark Office*

SEQUENCE LISTING

<160> NUMBER OF SEQ ID NOS: 17

<210> SEQ ID NO 1
<211> LENGTH: 591
<212> TYPE: DNA
<213> ORGANISM: Homo sapiens

<400> SEQUENCE: 1

```
ccgctgtcaa gatgcttctg gccatggtcc ttacctctgc cctgctcctg tgctccgtgg      60
caggccaggg gtgtccaacc ttggcgggga tcctggacat caacttcctc atcaacaaga     120
tgcaggaaga tccagcttcc aagtgccact gcagtgctaa tgtgaccagt tgtctctgtt     180
tgggcattcc ctctgacaac tgcaccagac catgcttcag tgagagactg tctcagatga     240
ccaataccac catgcaaaca agatacccac tgattttcag tcgggtgaaa aaatcagttg     300
aagtactaaa gaacaacaag tgtccatatt tttcctgtga acagccatgc aaccaaacca     360
cggcaggcaa cgcgctgaca tttctgaaga gtcttctgga aattttccag aaagaaaaga     420
tgagagggat gagaggcaag atatgaagat gaaatattat ttatcctatt tattaaattt     480
aaaaagcttt ctctttaagt tgctacaatt taaaaatcaa gtaagctact ctaaatcagt     540
atcagttgtg attatttgtt taacattgta tgtctttatt ttgaaataaa t              591
```

<210> SEQ ID NO 2
<211> LENGTH: 144
<212> TYPE: PRT
<213> ORGANISM: Homo sapiens

<400> SEQUENCE: 2

```
Met Leu Leu Ala Met Val Leu Thr Ser Ala Leu Leu Leu Cys Ser Val
1               5                   10                  15
```

Ala Gly Gln Gly Cys Pro Thr Leu Ala Gly Ile Leu Asp Ile Asn Phe
        20                  25                  30

Leu Ile Asn Lys Met Gln Glu Asp Pro Ala Ser Lys Cys His Cys Ser
    35                  40                  45

Ala Asn Val Thr Ser Cys Leu Cys Leu Gly Ile Pro Ser Asp Asn Cys
50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
            85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

<210> SEQ ID NO 3
<211> LENGTH: 2171
<212> TYPE: DNA
<213> ORGANISM: Homo sapiens

<400> SEQUENCE: 3

```
agcagctctg taatgcgctt gtggtttcag atgtgggcgg cctgtgtgaa cctgtcgtgc      60
aaagctcacg tcaccaactg ctgcagttat ctcctgaatc aggctgaggg tctttgctgt     120
gcacccagag atagttgggt gacaaatcac ctccaggttg ggatgcctc agacttgtga      180
tgggactggg cagatgcatc tgggaaggct ggaccttgga gagtgaggcc ctgaggcgag     240
acatgggcac ctggctcctg gcctgcatct gcatctgcac ctgtgtctgc ttgggagtct     300
ctgtcacagg ggaaggacaa gggccaaggt ctagaacctt cacctgcctc accaacaaca     360
ttctcaggat cgattgccac tggtctgccc cagagctggg acaggctcc agcccctggc      420
tcctcttcac cagcaaccag gctcctggcg cacacataa gtgcatcttg cggggcagtg      480
agtgcaccgt cgtgctgcca cctgaggcag tgctcgtgcc atctgacaat ttcaccatca     540
ctttccacca ctgcatgtct gggagggagc aggtcagcct ggtggacccg agtacctgc      600
cccggagaca cgttaagctg acccgccct ctgacttgca agcaacatc agttctggcc       660
actgcatcct gacctggagc atcagtcctg ccttggagcc aatgaccaca cttctcagct     720
atgagctggc cttcaagaag caggaagagg cctgggagca ggcccagcac agggatcaca     780
tgtcggggt gacctggctt atacttgaag cctttgagct ggaccctggc tttatccatg      840
aggccaggct gcgtgtccag atggccacac tggaggatga tgtggtagag gaggagcgtt     900
atacaggcca gtggagtgag tggagccagc ctgtgtgctt ccaggctccc cagagacaag     960
gccctctgat cccacccttgg ggtggccag gcaacaccct tgttgctgtg tccatctttc    1020
tcctgctgac tggcccgacc tacctcctgt tcaagctgtc gcccagggtg aagagaatct    1080
tctaccagaa cgtgccctct ccagcgatgt tcttccagcc cctctacagt gtacacaatg    1140
ggaacttcca gacttggatg ggggcccacg gggccggtgt gctgttgagc caggactgtg    1200
ctggcacccc acaggagcc ttggagccct gcgtccagga ggccactgca ctgctcactt     1260
gtggcccagc gcgtccttgg aaatctgtgg ccctggagga ggaacaggag ggccctggga    1320
ccaggctccc ggggaacctg agctcagagg atgtgctgcc agcagggtgt acggagtgga    1380
```

-continued

```
gggtacagac gcttgcctat ctgccacagg aggactgggc ccccacgtcc ctgactaggc    1440
cggctccccc agactcagag ggcagcagga gcagcagcag cagcagcagc agcaacaaca    1500
acaactactg tgccttgggc tgctatgggg gatggcacct ctcagccctc ccaggaaaca    1560
cacagagctc tgggcccatc ccagccctgg cctgtggcct ttcttgtgac catcagggcc    1620
tggagaccca gcaaggagtt gcctgggtgc tggctggtca ctgccagagg cctgggctgc    1680
atgaggacct ccagggcatg ttgctcccct ctgtcctcag caaggctcgg tcctggacat    1740
tctaggtccc tgactcgcca gatgcatcat gtccattttg ggaaaatgga ctgaagtttc    1800
tggagccctt gtctgagact gaacctcctg agaaggggcc cctagcagcg gtcagaggtc    1860
ctgtctggat ggaggctgga ggctcccccc tcaacccctc tgctcagtgc ctgtggggag    1920
cagcctctac cctcagcatc ctggccacaa gttcttcctt ccattgtccc ttttctttat    1980
ccctgacctc tctgagaagt ggggtgtggt ctctcagctg ttctgccctc atacccttaa    2040
agggccagcc tgggcccagt ggacacaggt aaggcaccat gaccacctgg tgtgacctct    2100
ctgtgcctta ctgaggcacc tttctagaga ttaaaagggg cttgatggct gttaaaaaaa    2160
aaaaaaaaaa a                                                        2171
```

<210> SEQ ID NO 4
<211> LENGTH: 521
<212> TYPE: PRT
<213> ORGANISM: Homo sapiens

<400> SEQUENCE: 4

```
Met Gly Leu Gly Arg Cys Ile Trp Glu Gly Trp Thr Leu Glu Ser Glu
1               5                   10                  15

Ala Leu Arg Arg Asp Met Gly Thr Trp Leu Leu Ala Cys Ile Cys Ile
                20                  25                  30

Cys Thr Cys Val Cys Leu Gly Val Ser Val Thr Gly Glu Gly Gln Gly
            35                  40                  45

Pro Arg Ser Arg Thr Phe Thr Cys Leu Thr Asn Asn Ile Leu Arg Ile
        50                  55                  60

Asp Cys His Trp Ser Ala Pro Glu Leu Gly Gln Gly Ser Ser Pro Trp
65                  70                  75                  80

Leu Leu Phe Thr Ser Asn Gln Ala Pro Gly Gly Thr His Lys Cys Ile
                85                  90                  95

Leu Arg Gly Ser Glu Cys Thr Val Val Leu Pro Pro Glu Ala Val Leu
            100                 105                 110

Val Pro Ser Asp Asn Phe Thr Ile Thr Phe His His Cys Met Ser Gly
        115                 120                 125

Arg Glu Gln Val Ser Leu Val Asp Pro Glu Tyr Leu Pro Arg Arg His
    130                 135                 140

Val Lys Leu Asp Pro Pro Ser Asp Leu Gln Ser Asn Ile Ser Ser Gly
145                 150                 155                 160

His Cys Ile Leu Thr Trp Ser Ile Ser Pro Ala Leu Glu Pro Met Thr
                165                 170                 175

Thr Leu Leu Ser Tyr Glu Leu Ala Phe Lys Lys Gln Glu Glu Ala Trp
            180                 185                 190

Glu Gln Ala Gln His Arg Asp His Ile Val Gly Val Thr Trp Leu Ile
        195                 200                 205

Leu Glu Ala Phe Glu Leu Asp Pro Gly Phe Ile His Glu Ala Arg Leu
    210                 215                 220

Arg Val Gln Met Ala Thr Leu Glu Asp Asp Val Val Glu Glu Glu Arg
```

```
                225                 230                 235                 240
        Tyr Thr Gly Gln Trp Ser Glu Trp Ser Gln Pro Val Cys Phe Gln Ala
                        245                 250                 255

Pro Gln Arg Gln Gly Pro Leu Ile Pro Pro Trp Gly Trp Pro Gly Asn
                        260                 265                 270

Thr Leu Val Ala Val Ser Ile Phe Leu Leu Thr Gly Pro Thr Tyr
                        275                 280             285

Leu Leu Phe Lys Leu Ser Pro Arg Val Lys Arg Ile Phe Tyr Gln Asn
                        290                 295                 300

Val Pro Ser Pro Ala Met Phe Phe Gln Pro Leu Tyr Ser Val His Asn
        305                 310                 315                 320

Gly Asn Phe Gln Thr Trp Met Gly Ala His Gly Ala Gly Val Leu Leu
                        325                 330                 335

Ser Gln Asp Cys Ala Gly Thr Pro Gln Gly Ala Leu Glu Pro Cys Val
                        340                 345                 350

Gln Glu Ala Thr Ala Leu Leu Thr Cys Gly Pro Ala Arg Pro Trp Lys
                        355                 360                 365

Ser Val Ala Leu Glu Glu Glu Gln Glu Gly Pro Gly Thr Arg Leu Pro
                        370                 375                 380

Gly Asn Leu Ser Ser Glu Asp Val Leu Pro Ala Gly Cys Thr Glu Trp
        385                 390                 395                 400

Arg Val Gln Thr Leu Ala Tyr Leu Pro Gln Glu Asp Trp Ala Pro Thr
                        405                 410                 415

Ser Leu Thr Arg Pro Ala Pro Pro Asp Ser Glu Gly Ser Arg Ser Ser
                        420                 425                 430

Ser Ser Ser Ser Ser Ser Asn Asn Asn Asn Tyr Cys Ala Leu Gly Cys
                        435                 440                 445

Tyr Gly Gly Trp His Leu Ser Ala Leu Pro Gly Asn Thr Gln Ser Ser
                        450                 455                 460

Gly Pro Ile Pro Ala Leu Ala Cys Gly Leu Ser Cys Asp His Gln Gly
        465                 470                 475                 480

Leu Glu Thr Gln Gln Gly Val Ala Trp Val Leu Ala Gly His Cys Gln
                        485                 490                 495

Arg Pro Gly Leu His Glu Asp Leu Gln Gly Met Leu Leu Pro Ser Val
                        500                 505                 510

Leu Ser Lys Ala Arg Ser Trp Thr Phe
                        515                 520

<210> SEQ ID NO 5
<211> LENGTH: 1560
<212> TYPE: DNA
<213> ORGANISM: Homo sapiens

<400> SEQUENCE: 5
agaggaaacg tgtgggtggg gagggggtagt gggtgaggga cccaggttcc tgacacagac      60
agactacacc cagggaatga agagcaagcg ccatgttgaa gccatcatta ccattcacat     120
ccctcttatt cctgcagctg cccctgctgg gagtgggggct gaacacgaca attctgacgc     180
ccaatgggaa tgaagacacc acagctgatt tcttcctgac cactatgccc actgactccc     240
tcagtgtttc cactctgccc ctcccagagg ttcagtgttt tgtgttcaat gtcgagtaca     300
tgaattgcac ttggaacagc agctctgagc cccagcctac caacctcact ctgcattatt     360
ggtacaagaa ctcggataat gataaagtcc agaagtgcag ccactatcta ttctctgaag     420
aaatcacttc tggctgtcag ttgcaaaaaa aggagatcca cctctaccaa acatttgttg     480
```

```
ttcagctcca ggacccacgg gaacccagga acaggccac acagatgcta aaactgcaga    540
atctggtgat cccctgggct ccagagaacc taacacttca aaactgagt gaatcccagc    600
tagaactgaa ctggaacaac agattcttga accactgttt ggagcacttg gtgcagtacc    660
ggactgactg gaccacagc tggactgaac atcagtgga ttatagacat aagttctcct    720
tgcctagtgt ggatgggcag aaacgctaca cgtttcgtgt tcggagccgc tttaacccac    780
tctgtggaag tgctcagcat tggagtgaat ggagccaccc aatccactgg gggagcaata    840
cttcaaaaga gaatcctttc ctgtttgcat tggaagccgt ggttatctct gttggctcca    900
tgggattgat tatcagcctt ctctgtgtgt atttctggct ggaacggacg atgccccgaa    960
ttcccaccct gaagaaccta gaggatcttg ttactgaata ccacgggaac ttttcggcct   1020
ggagtggtgt gtctaaggga ctggctgaga gtctgcagcc agactacagt gaacgactct   1080
gcctcgtcag tgagattccc ccaaaaggag gggcccttgg ggaggggcct ggggcctccc   1140
catgcaacca gcatagcccc tactgggccc cccatgtta cacccctaaag cctgaaacct   1200
gaaccccaat cctctgacag aagaacccca gggtcctgta gccctaagtg gtactaactt   1260
tccttcattc aacccacctg cgtctcatac tcacctcacc ccactgtggc tgatttggaa   1320
ttttgtgccc ccatgtaagc accccttcat ttggcattcc ccacttgaga attacccttt   1380
tgccccgaac atgttttct tctccctcag tctggccctt cctttcgca ggattcttcc   1440
tccctccctc tttccctccc ttcctctttc catctaccct ccgattgttc ctgaaccgat   1500
gagaaataaa gtttctgttg ataatcatca aaaaaaaaa aaaaaaaaa aaaaaaaaa   1560
```

<210> SEQ ID NO 6
<211> LENGTH: 369
<212> TYPE: PRT
<213> ORGANISM: Homo sapiens

<400> SEQUENCE: 6

```
Met Leu Lys Pro Ser Leu Pro Phe Thr Ser Leu Leu Phe Leu Gln Leu
1               5                  10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
```

```
                  180                 185                 190
Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
            210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
            290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
            355                 360                 365

Thr

<210> SEQ ID NO 7
<211> LENGTH: 1209
<212> TYPE: DNA
<213> ORGANISM: Homo sapiens

<400> SEQUENCE: 7
aggagcgttt ttggagaaag ctgcactctg ttgagctcca gggcgcagtg gagggaggga    60
gtgaaggagc tctctgtacc caaggaaagt gcagctgaga ctcagacaag attacaatga   120
accaactcag cttcctgctg tttctcatag cgaccaccag aggatggagt acagatgagg   180
ctaatactta cttcaaggaa tggacctgtt cttcgtctcc atctctgccc agaagctgca   240
aggaaatcaa agacgaatgt cctagtgcat ttgatggcct gtattttctc cgcactgaga   300
atggtgttat ctaccagacc ttctgtgaca tgacctctgg gggtggcggc tggacccttg   360
tggccagcgt gcacgagaat gacatgcgtg ggaagtgcac ggtgggcgat cgctggtcca   420
gtcagcaggg cagcaaagca gtctacccag aggggacgg caactgggcc aactacaaca   480
cctttggatc tgcagaggcg gccacgagcg atgactacaa gaaccctggc tactacgaca   540
tccaggccaa ggacctgggc atctggcacg tgcccaataa gtcccccatg cagcactgga   600
gaaacagctc cctgctgagg taccgcacgg acactggctt cctccagaca ctggacata    660
atctgtttgg catctaccag aaatatccag tgaaatatgg agaaggaaag tgttggactg   720
acaacggccc ggtgatccct gtggtctatg attttggcga cgcccagaaa acagcatctt   780
attactcacc ctatgccag cgggaattca ctgcgggatt tgttcagttc agggtattta   840
ataacgagag agcagccaac gccttgtgtg ctggaatgag ggtcaccgga tgtaacactg   900
agcaccactg cattggtgga ggaggatact ttcagaggc cagtcccag cagtgtggag   960
atttttctgg ttttgattgg agtggatatg gaactcatgt tggttacagc agcagccgtg  1020
```

```
agataactga ggcagctgtg cttctattct atcgttgaga gttttgtggg agggaaccca    1080
gacctctcct cccaaccatg agatcccaag gatggagaac aacttaccca gtagctagaa    1140
tgttaatggc agaagagaaa acaataaatc atattgactc aaaaaaaaaa aaaaaaaaaa    1200
aaaaaaaaa                                                             1209
```

<210> SEQ ID NO 8
<211> LENGTH: 313
<212> TYPE: PRT
<213> ORGANISM: Homo sapiens

<400> SEQUENCE: 8

```
Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Arg Glu Ile Thr
    290                 295                 300

Glu Ala Ala Val Leu Leu Phe Tyr Arg
305                 310
```

<210> SEQ ID NO 9
<211> LENGTH: 4043

<212> TYPE: DNA
<213> ORGANISM: Homo sapiens

<400> SEQUENCE: 9

```
tcccagatgg atccacccca gacttttcaa agaagacacc tccttcatct tgtgttctaa      60
aaccttgcaa gttcaggaag aaaccatctg catccatatt gaaaacctga cacaatgtat     120
gcagcaggct cagtgtgagt gaactggagg cttctctaca acatgaccca aggagcatt     180
gcaggtccta tttgcaacct gaagtttgtg actctcctgg ttgccttaag ttcagaactc     240
ccattcctgg gagctggagt acagcttcaa gacaatgggt ataatggatt gctcattgca     300
attaatcctc aggtacctga gaatcagaac ctcatctcaa acattaagga aatgataact     360
gaagcttcat tttacctatt taatgctacc aagagaagag tattttttcag aaatataaag     420
attttaatac ctgccacatg gaaagctaat aataacagca aaataaaaca gaatcatat     480
gaaaaggcaa atgtcatagt gactgactgg tatggggcac atggagatga tccatacacc     540
ctacaataca gagggtgtgg aaaagaggga aaatacattc atttcacacc taatttccta     600
ctgaatgata acttaacagc tggctacgga tcacgaggcc gagtgtttgt ccatgaatgg     660
gcccacctcc gttggggtgt gttcgatgag tataacaatg acaaaccttt ctacataaat     720
gggcaaaatc aaattaaagt gacaaggtgt tcatctgaca tcacaggcat ttttgtgtgt     780
gaaaaaggtc cttgcccccca agaaaactgt attattagta agcttttttaa agaaggatgc     840
accttttatct acaatagcac ccaaaatgca actgcatcaa taatgttcat gcaaagttta     900
tcttctgtgg ttgaatttttg taatgcaagt acccacaacc aagaagcacc aaacctacag     960
aaccagatgt gcagcctcag aagtgcatgg gatgtaatca cagactctgc tgactttcac    1020
cacagctttc ccatgaatgg gactgagctt ccacctcctc ccacattctc gcttgtacag    1080
gctggtgaca agtggtctg tttagtgctg gatgtgtcca gcaagatggc agaggctgac    1140
agactccttc aactcaaaca gccgcagaa ttttatttga tgcagattgt tgaaattcat    1200
accttcgtgg gcattgccag tttcgacagc aaaggagaga tcagagccca gctacaccaa    1260
attaacagca atgatgatcg aaagttgctg gtttcatatc tgcccaccac tgtatcagct    1320
aaaacagaca tcagcatttg ttcagggctt aagaaaggat ttgaggtggt tgaaaaactg    1380
aatggaaaag cttatggctc tgtgatgata ttagtgacca gcggagatga taagcttctt    1440
ggcaattgct tacccactgt gctcagcagt ggttcaacaa ttcactccat tgccctgggt    1500
tcatctgcag ccccaaatct ggaggaatta tcacgtctta caggaggttt aaagttcttt    1560
gttccagata tatcaaactc caatagcatg attgatgctt tcagtagaat ttcctctgga    1620
actggagaca ttttccagca acatattcag cttgaaagta caggtgaaaa tgtcaaacct    1680
caccatcaat tgaaaaacac agtgactgtg gataatactg tgggcaacga cactatgttt    1740
ctagttacgt ggcaggccag tggtcctcct gagattatat tatttgatcc tgatggacga    1800
aaatactaca caaataattt tatcaccaat ctaactttc ggacagctag tctttggatt    1860
ccaggaacag ctaagcctgg gcactggact tacaccctga caatacccca tcattctctg    1920
caagccctga agtgacagt gacctctcgc gcctccaact cagctgtgcc cccagccact    1980
gtggaagcct ttgtggaaag agacagcctc cattttcctc atcctgtgat gatttatgcc    2040
aatgtgaaac agggattta tcccattctt aatgccactg tcactgccac agttgagcca    2100
gagactggag atcctgttac gctgagactc cttgatgatg gagcaggtgc tgatgttata    2160
aaaatgatg gaatttactc gaggtatttt ttctcctttg ctgcaaatgg tagatatagc    2220
```

```
ttgaaagtgc atgtcaatca ctctcccagc ataagcaccc cagcccactc tattccaggg    2280
agtcatgcta tgtatgtacc aggttacaca gcaaacggta atattcagat gaatgctcca    2340
aggaaatcag taggcagaaa tgaggaggag cgaaagtggg gctttagccg agtcagctca    2400
ggaggctcct tttcagtgct gggagttcca gctggccccc accctgatgt gtttccacca    2460
tgcaaaatta ttgacctgga agctgtaaaa gtagaagagg aattgaccct atcttggaca    2520
gcacctggag aagactttga tcagggccag gctacaagct atgaaataag aatgagtaaa    2580
agtctacaga atatccaaga tgactttaac aatgctattt tagtaaatac atcaaagcga    2640
aatcctcagc aagctggcat cagggagata tttacgttct cacccccaaat ttccacgaat    2700
ggacctgaac atcagccaaa tggagaaaca catgaaagcc acagaattta tgttgcaata    2760
cgagcaatgg ataggaactc cttacagtct gctgtatcta acattgccca ggcgcctctg    2820
tttattcccc ccaattctga tcctgtacct gccagagatt atcttatatt gaaaggagtt    2880
taacagcaa tgggtttgat aggaatcatt tgccttatta tagttgtgac acatcatact    2940
ttaagcagga aaaagagagc agacaagaaa gagaatggaa caaaattatt ataaataaat    3000
atccaaagtg tcttccttct tagatataag acccatggcc ttcgactaca aaacatact     3060
aacaaagtca aattaacatc aaaactgtat taaaatgcat tgagttttg tacaatacag      3120
ataagatttt tacatggtag atcaacaaat tcttttttggg ggtagattag aaaaccctta   3180
cactttggct atgaacaaat aataaaaatt attctttaaa gtaatgtctt taaaggcaaa    3240
gggaagggta aagtcggacc agtgtcaagg aaagtttgtt ttattgaggt ggaaaaatag    3300
ccccaagcag agaaaggag ggtaggtctg cattataact gtctgtgtga agcaatcatt      3360
tagttacttt gattaatttt tcttttctcc ttatctgtgc agaacaggtt gcttgtttac     3420
aactgaagat catgctatat tttatatatg aagcccctaa tgcaaagctc tttacctctt    3480
gctatttgt tatatatatt acagatgaaa tctcactgct aatgctcaga gatcttttt      3540
cactgtaaga ggtaaccttt aacaatatgg gtattacctt tgtctcttca taccggttt     3600
atgacaaagg tctattgaat ttatttgttt gtaagtttct actcccatca aagcagcttt    3660
ctaagttatt gccttggtta ttatggatga tagttatagc ccttataatg ccttaactaa    3720
ggaagaaaag atgttattct gagtttgttt taatacatat atgaacatat agttttattc    3780
aattaaacca agaagaggt cagcagggag atactaacct ttggaaatga ttagctggct     3840
ctgtttttg gttaaataag agtctttaat cctttctcca tcaagagtta cttaccaagg      3900
gcagggggaag ggggatatag aggtcacaag gaaataaaaa tcatctttca tctttaattt  3960
tactccttcc tcttattttt ttaaaagatt atcgaacaat aaaatcattt gccttttaa     4020
ttaaaaaaaa aaaaaaaaaa aaa                                              4043
```

<210> SEQ ID NO 10
<211> LENGTH: 943
<212> TYPE: PRT
<213> ORGANISM: Homo sapiens

<400> SEQUENCE: 10

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

```
Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
    275                 280                 285

Phe Pro Met Asn Gly Thr Glu Leu Pro Pro Pro Thr Phe Ser Leu
290                 295                 300

Val Gln Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
    355                 360                 365

Ser Asn Asp Asp Arg Lys Leu Leu Val Ser Tyr Leu Pro Thr Thr Val
370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
    435                 440                 445

Ala Ala Pro Asn Leu Glu Glu Leu Ser Arg Leu Thr Gly Gly Leu Lys
450                 455                 460

Phe Phe Val Pro Asp Ile Ser Asn Ser Asn Ser Met Ile Asp Ala Phe
```

-continued

```
            465                 470                 475                 480
        Ser Arg Ile Ser Ser Gly Thr Gly Asp Ile Phe Gln Gln His Ile Gln
                        485                 490                 495
        Leu Glu Ser Thr Gly Glu Asn Val Lys Pro His His Gln Leu Lys Asn
                        500                 505                 510
        Thr Val Thr Val Asp Asn Thr Val Gly Asn Asp Thr Met Phe Leu Val
                        515                 520                 525
        Thr Trp Gln Ala Ser Gly Pro Pro Glu Ile Ile Leu Phe Asp Pro Asp
                        530                 535                 540
        Gly Arg Lys Tyr Tyr Thr Asn Asn Phe Ile Thr Asn Leu Thr Phe Arg
        545                 550                 555                 560
        Thr Ala Ser Leu Trp Ile Pro Gly Thr Ala Lys Pro Gly His Trp Thr
                        565                 570                 575
        Tyr Thr Leu Asn Asn Thr His His Ser Leu Gln Ala Leu Lys Val Thr
                        580                 585                 590
        Val Thr Ser Arg Ala Ser Asn Ser Ala Val Pro Pro Ala Thr Val Glu
                        595                 600                 605
        Ala Phe Val Glu Arg Asp Ser Leu His Phe Pro His Pro Val Met Ile
                        610                 615                 620
        Tyr Ala Asn Val Lys Gln Gly Phe Tyr Pro Ile Leu Asn Ala Thr Val
        625                 630                 635                 640
        Thr Ala Thr Val Glu Pro Glu Thr Gly Asp Pro Val Thr Leu Arg Leu
                        645                 650                 655
        Leu Asp Asp Gly Ala Gly Ala Asp Val Ile Lys Asn Asp Gly Ile Tyr
                        660                 665                 670
        Ser Arg Tyr Phe Phe Ser Phe Ala Ala Asn Gly Arg Tyr Ser Leu Lys
                        675                 680                 685
        Val His Val Asn His Ser Pro Ser Ile Ser Thr Pro Ala His Ser Ile
                        690                 695                 700
        Pro Gly Ser His Ala Met Tyr Val Pro Gly Tyr Thr Ala Asn Gly Asn
        705                 710                 715                 720
        Ile Gln Met Asn Ala Pro Arg Lys Ser Val Gly Arg Asn Glu Glu Glu
                        725                 730                 735
        Arg Lys Trp Gly Phe Ser Arg Val Ser Ser Gly Gly Ser Phe Ser Val
                        740                 745                 750
        Leu Gly Val Pro Ala Gly Pro His Pro Asp Val Phe Pro Pro Cys Lys
                        755                 760                 765
        Ile Ile Asp Leu Glu Ala Val Lys Val Glu Glu Leu Thr Leu Ser
                        770                 775                 780
        Trp Thr Ala Pro Gly Glu Asp Phe Asp Gln Gly Gln Ala Thr Ser Tyr
        785                 790                 795                 800
        Glu Ile Arg Met Ser Lys Ser Leu Gln Asn Ile Gln Asp Asp Phe Asn
                        805                 810                 815
        Asn Ala Ile Leu Val Asn Thr Ser Lys Arg Asn Pro Gln Gln Ala Gly
                        820                 825                 830
        Ile Arg Glu Ile Phe Thr Phe Ser Pro Gln Ile Ser Thr Asn Gly Pro
                        835                 840                 845
        Glu His Gln Pro Asn Gly Glu Thr His Glu Ser His Arg Ile Tyr Val
                        850                 855                 860
        Ala Ile Arg Ala Met Asp Arg Asn Ser Leu Gln Ser Ala Val Ser Asn
        865                 870                 875                 880
        Ile Ala Gln Ala Pro Leu Phe Ile Pro Pro Asn Ser Asp Pro Val Pro
                        885                 890                 895
```

```
Ala Arg Asp Tyr Leu Ile Leu Lys Gly Val Leu Thr Ala Met Gly Leu
        900                 905                 910

Ile Gly Ile Ile Cys Leu Ile Ile Val Val Thr His His Thr Leu Ser
    915                 920                 925

Arg Lys Lys Arg Ala Asp Lys Lys Glu Asn Gly Thr Lys Leu Leu
    930                 935                 940

<210> SEQ ID NO 11
<211> LENGTH: 3054
<212> TYPE: DNA
<213> ORGANISM: Homo sapiens

<400> SEQUENCE: 11
agagagctag gtgcagagct tcaggctgag gcgctgctga gagggcctcg ccccgcctct     60
gccgccagct gcaccccact cctggaccac cccctgctga gaaggacagg gagccaaggc    120
cggcagagcc aaggctcagt catgagaaca caaattgaag tgatcccttg caaaatctgt    180
ggggacaagt cgtctgggat ccactacggg gttatcacct gtgaggggtg caagggcttc    240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg    360
ggcatgtccc gagatgctgt caagttcggc cgcatgtcca agaagcagag ggacagcctg    420
catgcagaag tgcagaaaca gctgcagcag cggcaacagc agcaacagga ccagtggtc    480 aagaccctc cagcaggggc ccaaggagca gatacctca cctacacctt ggggctccca    540
gacgggcagc tgcccctggg ctcctcgcct gacctgcctg aggcttctgc ctgtcccct    600 ggcctcctga agcctcagg ctctgggccc tcatattcca caacttggc caaggcaggg    660 ctcaatgggg cctcatgcca ccttgaatac agccctgagc ggggcaaggc tgagggcaga    720
gagagcttct atagcacagg cagccagctg accctgacc gatgtggact tcgtttttgag    780 gaacacaggc atcctgggct tggggaactg ggacagggcc cagacagcta cggcagcccc    840
agtttccgca gcacaccgga ggcaccctat gcctccctga cagagataga gcacctggtg    900
cagagcgtct gcaagtccta cagggagaca tgccagctgc ggctgaagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc   1080
gccaagaggc tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt ttgaaggcaa atacggtggc atggagctgt tccgagcctt gggctgcagc   1260
gagctcatca gctccatctt tgacttctcc cactccctaa gtgccttgca cttttccgag   1320
gatgagattg ccctctacac agcccttgtt ctcatcaatg cccatcggcc agggctccaa   1380
gagaaaagga agtgaaaca gctgcagtac aatctggagc tggcctttca tcatcatctc   1440
tgcaagactc atcgccaaag catcctggca aagctgccac ccaaggggaa gcttcggagc   1500
ctgtgtagcc agcatgtgga aaggctgcag atcttccagc acctccaccc catcgtggtc   1560
caagccgctt tccctccact ctacaaggag ctcttcagca ctgaaaccga gtcacctgtg   1620
gggctgtcca agtgacctgg aagagggact ccttgcctct ccctatggcc tgctggccca   1680 cctcccctgga ccccgttcca ccctcacct tttcctttcc catgaaccct ggagggtggt   1740
ccccaccagc tctttggaag tgagcagatg ctgcggctgg ctttctgtca gcaggccggc   1800
ctggcagtgg gacaatcgcc agagggtggg gctggcagaa caccatctcc agcctcagct   1860
```

-continued

```
ttgacctgtc tcatttccca tattccttca cacccagctt ctggaaggca tggggtggct    1920
gggatttaag gacttctggg ggaccaagac atcctcaaga aaacaggggc atccagggct    1980
ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctgggtct     2220
aaccaaaaat ggatgggatg aggatgagag gctggagata attgttttat gggatttggg    2280
tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
caggggaaag tcccaatcct gagggaccct cccaaacatt tccatggtgc tccagtccac    2580
tgatcttggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc ccgccagccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccagaac ctctcttggc ttcataaaca    2880
gctgtgaacc ctcccctgag ggattaacag caatgatggg cagtcgtgga gttgggggg     2940
ttgggggtgg gattgtgtcc tctaagggga cgggttcatc tgagtaaaca taaaccccaa    3000
cttgtgccat tctttataaa atgattttaa aggcaaaaaa aaaaaaaaaa aaaa          3054
```

<210> SEQ ID NO 12
<211> LENGTH: 497
<212> TYPE: PRT
<213> ORGANISM: Homo sapiens

<400> SEQUENCE: 12

```
Met Arg Thr Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
            20                  25                  30

Phe Phe Arg Arg Ser Gln Arg Cys Asn Ala Ala Tyr Ser Cys Thr Arg
        35                  40                  45

Gln Gln Asn Cys Pro Ile Asp Arg Thr Ser Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys Gln Leu Gln Gln Arg Gln Gln Gln Gln Glu Pro Val
            100                 105                 110

Val Lys Thr Pro Pro Ala Gly Ala Gln Gly Ala Asp Thr Leu Thr Tyr
        115                 120                 125

Thr Leu Gly Leu Pro Asp Gly Gln Leu Pro Leu Gly Ser Ser Pro Asp
    130                 135                 140

Leu Pro Glu Ala Ser Ala Cys Pro Pro Gly Leu Leu Lys Ala Ser Gly
145                 150                 155                 160
```

```
Ser Gly Pro Ser Tyr Ser Asn Asn Leu Ala Lys Ala Gly Leu Asn Gly
            165                 170                 175

Ala Ser Cys His Leu Glu Tyr Ser Pro Glu Arg Gly Lys Ala Glu Gly
        180                 185                 190

Arg Glu Ser Phe Tyr Ser Thr Gly Ser Gln Leu Thr Pro Asp Arg Cys
    195                 200                 205

Gly Leu Arg Phe Glu His Arg His Pro Gly Leu Gly Glu Leu Gly
210                 215                 220

Gln Gly Pro Asp Ser Tyr Gly Ser Pro Ser Phe Arg Ser Thr Pro Glu
225                 230                 235                 240

Ala Pro Tyr Ala Ser Leu Thr Glu Ile Glu His Leu Val Gln Ser Val
                245                 250                 255

Cys Lys Ser Tyr Arg Glu Thr Cys Gln Leu Arg Leu Glu Asp Leu Leu
            260                 265                 270

Arg Gln Arg Ser Asn Ile Phe Ser Arg Glu Val Thr Gly Tyr Gln
        275                 280                 285

Arg Lys Ser Met Trp Glu Met Trp Glu Arg Cys Ala His His Leu Thr
    290                 295                 300

Glu Ala Ile Gln Tyr Val Val Glu Phe Ala Lys Arg Leu Ser Gly Phe
305                 310                 315                 320

Met Glu Leu Cys Gln Asn Asp Gln Ile Val Leu Leu Lys Ala Gly Ala
                325                 330                 335

Met Glu Val Val Leu Val Arg Met Cys Arg Ala Tyr Asn Ala Asp Asn
            340                 345                 350

Arg Thr Val Phe Phe Glu Gly Lys Tyr Gly Gly Met Glu Leu Phe Arg
        355                 360                 365

Ala Leu Gly Cys Ser Glu Leu Ile Ser Ser Ile Phe Asp Phe Ser His
    370                 375                 380

Ser Leu Ser Ala Leu His Phe Ser Glu Asp Glu Ile Ala Leu Tyr Thr
385                 390                 395                 400

Ala Leu Val Leu Ile Asn Ala His Arg Pro Gly Leu Gln Glu Lys Arg
                405                 410                 415

Lys Val Glu Gln Leu Gln Tyr Asn Leu Glu Leu Ala Phe His His His
            420                 425                 430

Leu Cys Lys Thr His Arg Gln Ser Ile Leu Ala Lys Leu Pro Pro Lys
        435                 440                 445

Gly Lys Leu Arg Ser Leu Cys Ser Gln His Val Glu Arg Leu Gln Ile
    450                 455                 460

Phe Gln His Leu His Pro Ile Val Val Gln Ala Ala Phe Pro Pro Leu
465                 470                 475                 480

Tyr Lys Glu Leu Phe Ser Thr Glu Thr Glu Ser Pro Val Gly Leu Ser
                485                 490                 495

Lys
```

<210> SEQ ID NO 13
<211> LENGTH: 3084
<212> TYPE: DNA
<213> ORGANISM: Homo sapiens

<400> SEQUENCE: 13
gccaggtgct cccgccttcc accctccgcc ctcctccctc ccctgggccc tgctccctgc    60
cctcctgggc agccagggca gccaggacgg caccaaggga gctgcccat ggacagggcc   120 ccacagagac agcaccgagc ctcacgggag ctgctggctg caaagaagac ccacacctca   180

```
caaattgaag tgatcccttg caaaatctgt ggggacaagt cgtctgggat ccactacggg      240
gttatcacct gtgagggtg caagggcttc ttccgccgga gccagcgctg taacgcggcc       300
tactcctgca cccgtcagca gaactgcccc atcgaccgca ccagccgaaa ccgatgccag      360
cactgccgcc tgcagaaatg cctggcgctg ggcatgtccc gagatgctgt caagttcggc      420
cgcatgtcca agaagcagag ggacagcctg catgcagaag tgcagaaaca gctgcagcag      480
cggcaacagc agcaacagga accagtggtc aagacccctc agcagggggc caaggagca       540 gataccctca cctacacctt ggggctccca gacgggcagc tgcccctggg ctcctcgcct      600
gacctgcctg aggcttctgc ctgtccccct ggcctcctga agcctcagg ctctgggccc       660 tcatattcca caacttggc caaggcaggg ctcaatgggg cctcatgcca ccttgaatac       720
agccctgagc ggggcaaggc tgagggcaga gagagcttct atagcacagg cagccagctg      780 accctgacc gatgtggact tcgttttgag gaacacagg atcctgggct tggggaactg        840
ggacagggcc cagacagcta cggcagcccc agtttccgca gcacaccgga ggcaccctat      900
gcctccctga cagagataga gcacctggtg cagagcgtct gcaagtccta cagggagaca      960
tgccagctgc ggctggagga cctgctgcgg cagcgctcca acatcttctc ccggaggaa      1020 gtgactggct accagaggaa gtccatgtgg gagatgtggg aacggtgtgc ccaccacctc     1080
accgaggcca ttcagtacgt ggtggagttc gccaagaggc tctcaggctt tatggagctc     1140
tgccagaatg accagattgt gcttctcaaa gcaggagcaa tggaagtggt gctggttagg     1200
atgtgccggg cctacaatgc tgacaaccgc acggtctttt ttgaaggcaa atacggtggc     1260
atggagctgt tccgagcctt gggctgcagc gagctcatca gctccatctt tgacttctcc     1320
cactccctaa gtgccttgca ctttccgag gatgagattg ccctctacac agcccttgtt      1380
ctcatcaatg cccatcggcc agggctccaa gagaaaagga agtagaaaca gctgcagtac     1440
aatctggagc tggcctttca tcatcatctc tgcaagactc atcgccaaag catcctggca     1500
aagctgccac ccaaggggaa gcttcggagc ctgtgtagcc agcatgtgga aaggctgcag     1560
atcttccagc acctccaccc catcgtggtc caagccgctt tccctccact ctacaaggag     1620
ctcttcagca ctgaaaccga gtcacctgtg gggctgtcca agtgacctgg agagggact     1680 ccttgcctct ccctatggcc tgctggccca cctccctgga ccccgttcca ccctcaccct     1740
tttcctttcc catgaaccct ggagggtggt ccccaccagc tctttggaag tgagcagatg     1800
ctgcggctgg cttttctgtca gcaggccggc ctggcagtgg gacaatcgcc agagggtggg     1860
gctggcagaa caccatctcc agcctcagct ttgacctgtc tcatttccca tattccttca     1920
cacccagctt ctggaaggca tggggtggct gggatttaag gacttctggg ggaccaagac     1980
atcctcaaga aaacagggc atccaggct ccctggatga atagaatgca attcattcag       2040
aagctcagaa gctaagaata agcctttgaa atacctcatt gcatttccct ttgggcttcg     2100
gcttggggag atggatcaag ctcagagact ggcagtgaga gcccagaagg acctgtataa    2160
aatgaatctg gagctttaca ttttctgcct ctgccttcct cccagctcag caaggaagta    2220
tttgggcacc ctaccctta cctggggtct aaccaaaaat ggatgggatg aggatgagag    2280 gctgagata attgttttat gggatttggg tgtgggacta gggtacaatg aaggccaaga   2340
gcatctcaga catagagtta aaactcaaac ctcttatgtg cactttaaag atagacttta   2400
ggggctggca caaatctgat cagagacaca tatccataca caggtgaaac acatacagac   2460
tcaacagcaa tcatgcagtt ccagagacac atgaacctga cacaatctct cttatccttg   2520
aggccacagc ttggaggagc ctagaggcct caggggaaag tcccaatcct gagggaccct   2580
```

```
cccaaacatt tccatggtgc tccagtccac tgatcttggg tctggggtga tccaaatacc    2640
accccagctc cagctgtctt ctaccactag aagacccaag agaagcagaa gtcgctcgca    2700
ctggtcagtc ggaaggcaag atcagatcct ggaggacttt cctggcctgc ccgccagccc    2760
tgctcttgtt gtggagaagg aagcagatgt gatcacatca ccccgtcatt gggcaccgct    2820
gactccagca tggaggacac cagggagcag ggcctgggcc tgtttcccca gctgtgatct    2880
tgcccagaac ctctcttggc ttcataaaca gctgtgaacc ctcccctgag ggattaacag    2940
caatgatggg cagtcgtgga gttggggggg ttggggtgg gattgtgtcc tctaagggga    3000
cgggttcatc tgagtaaaca taaaccccaa cttgtgccat tctttataaa atgatttaa    3060 aggcaaaaaa aaaaaaaaaa aaaa    3084
```

<210> SEQ ID NO 14
<211> LENGTH: 518
<212> TYPE: PRT
<213> ORGANISM: Homo sapiens

<400> SEQUENCE: 14

```
Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Arg Cys Asn Ala Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
    130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
```

```
                    275                 280                 285

Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                    325                 330                 335

Arg Leu Ser Gly Phe Met Glu Leu Cys Gln Asn Asp Gln Ile Val Leu
                340                 345                 350

Leu Lys Ala Gly Ala Met Glu Val Val Leu Val Arg Met Cys Arg Ala
            355                 360                 365

Tyr Asn Ala Asp Asn Arg Thr Val Phe Phe Glu Gly Lys Tyr Gly Gly
        370                 375                 380

Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
                    405                 410                 415

Ile Ala Leu Tyr Thr Ala Leu Val Leu Ile Asn Ala His Arg Pro Gly
                420                 425                 430

Leu Gln Glu Lys Arg Lys Val Glu Gln Leu Gln Tyr Asn Leu Glu Leu
            435                 440                 445

Ala Phe His His His Leu Cys Lys Thr His Arg Gln Ser Ile Leu Ala
        450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                    485                 490                 495

Ala Phe Pro Pro Leu Tyr Lys Glu Leu Phe Ser Thr Glu Thr Glu Ser
                500                 505                 510

Pro Val Gly Leu Ser Lys
            515

<210> SEQ ID NO 15
<211> LENGTH: 20
<212> TYPE: PRT
<213> ORGANISM: Unknown
<220> FEATURE:
<223> OTHER INFORMATION: Description of Unknown: KP-20 peptide

<400> SEQUENCE: 15

Phe Ser Arg Val Lys Lys Ser Val Glu Val Leu Lys Asn Asn Lys Ala
1               5                   10                  15

Pro Tyr Phe Ser
            20

<210> SEQ ID NO 16
<211> LENGTH: 27
<212> TYPE: PRT
<213> ORGANISM: Unknown
<220> FEATURE:
<223> OTHER INFORMATION: Description of Unknown: KP-89 peptide

<400> SEQUENCE: 16

Ser Arg Arg Ala Ser Val Gly Phe Ser Arg Val Lys Lys Ser Val Glu
1               5                   10                  15

Val Leu Lys Asn Asn Lys Ala Pro Tyr Phe Ser
            20                  25
```

```
<210> SEQ ID NO 17
<211> LENGTH: 351
<212> TYPE: PRT
<213> ORGANISM: Human T-lymphotropic virus 1

<400> SEQUENCE: 17

His Phe Pro Gly Phe Gly Gln Ser Leu Leu Phe Gly Tyr Pro Val Tyr
1               5                   10                  15

Val Phe Gly Asp Cys Val Gln Gly Asp Trp Cys Pro Ile Ser Gly Gly
            20                  25                  30

Leu Cys Ser Ala Arg Leu His Arg His Ala Leu Leu Ala Thr Cys Pro
        35                  40                  45

Glu His Gln Ile Thr Trp Asp Pro Ile Asp Gly Arg Val Ile Gly Ser
    50                  55                  60

Ala Leu Gln Phe Leu Ile Pro Arg Leu Pro Ser Phe Pro Thr Gln Arg
65                  70                  75                  80

Thr Ser Lys Thr Leu Lys Val Leu Thr Pro Pro Ile Thr His Thr Thr
                85                  90                  95

Pro Asn Ile Pro Pro Ser Phe Leu Gln Ala Met Arg Lys Tyr Ser Pro
            100                 105                 110

Phe Arg Asn Gly Tyr Met Glu Pro Thr Leu Gly Gln His Leu Pro Thr
        115                 120                 125

Leu Ser Phe Pro Asp Pro Gly Leu Arg Pro Gln Asn Leu Tyr Thr Leu
    130                 135                 140

Trp Gly Gly Ser Val Val Cys Met Tyr Leu Tyr Gln Leu Ser Pro Pro
145                 150                 155                 160

Ile Thr Trp Pro Leu Leu Pro His Val Ile Phe Cys His Pro Gly Gln
                165                 170                 175

Leu Gly Ala Phe Leu Thr Asn Val Pro Tyr Lys Arg Ile Glu Glu Leu
            180                 185                 190

Leu Tyr Lys Ile Ser Leu Thr Thr Gly Ala Leu Ile Ile Leu Pro Glu
        195                 200                 205

Asp Cys Leu Pro Thr Thr Leu Phe Gln Pro Ala Arg Ala Pro Val Thr
    210                 215                 220

Leu Thr Ala Trp Gln Asn Gly Leu Leu Pro Phe His Ser Thr Leu Thr
225                 230                 235                 240

Thr Pro Gly Leu Ile Trp Thr Phe Thr Asp Gly Thr Pro Met Ile Ser
                245                 250                 255

Gly Pro Cys Pro Lys Asp Gly Gln Pro Ser Leu Val Leu Gln Ser Ser
            260                 265                 270

Ser Phe Ile Phe His Lys Phe Gln Thr Lys Ala Tyr His Pro Ser Phe
        275                 280                 285

Leu Leu Ser His Gly Leu Ile Gln Tyr Ser Ser Phe His Ser Leu His
    290                 295                 300

Leu Leu Phe Glu Glu Tyr Thr Asn Ile Pro Ile Ser Leu Leu Phe Asn
305                 310                 315                 320

Glu Lys Glu Ala Asp Asp Asn Asp His Glu Pro Gln Ile Ser Pro Gly
                325                 330                 335

Gly Leu Glu Pro Pro Ser Glu Lys His Phe Arg Glu Thr Glu Val
            340                 345                 350
```